United States Patent
Lim et al.

(10) Patent No.: US 9,371,270 B2
(45) Date of Patent: Jun. 21, 2016

(54) COMPOUND FOR ORGANIC LIGHT-EMITTING DEVICE AND ORGANIC LIGHT-EMITTING DEVICE INCLUDING THE SAME

(71) Applicant: SAMSUNG DISPLAY CO., LTD., Yongin-si, Gyeonggi-do (KR)

(72) Inventors: Jin-O Lim, Yongin-si (KR); Seok-Hwan Hwang, Yongin-si (KR); Young-Kook Kim, Yongin-si (KR); Hye-Jin Jung, Yongin-si (KR); Sang-Hyun Han, Yongin-si (KR); Soo-Yon Kim, Yongin-si (KR); Eun-Jae Jeong, Yongin-si (KR); Jun-Ha Park, Yongin-si (KR); Eun-Young Lee, Yongin-si (KR); Il-Soo Oh, Yongin-si (KR); Jong-Hyuk Lee, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 714 days.

(21) Appl. No.: 13/675,973

(22) Filed: Nov. 13, 2012

(65) Prior Publication Data
US 2013/0328021 A1  Dec. 12, 2013

(30) Foreign Application Priority Data
Jun. 12, 2012 (KR) .................. 10-2012-0062860

(51) Int. Cl.
| | | |
|---|---|---|
| H01L 51/54 | (2006.01) |
| C09K 11/06 | (2006.01) |
| C07C 211/54 | (2006.01) |
| C07D 403/12 | (2006.01) |
| C07D 333/76 | (2006.01) |
| C07D 307/91 | (2006.01) |
| C07D 213/38 | (2006.01) |
| C07D 213/74 | (2006.01) |
| H01L 51/00 | (2006.01) |
| C07C 255/58 | (2006.01) |
| C07D 401/12 | (2006.01) |
| C07C 211/56 | (2006.01) |
| C07C 211/58 | (2006.01) |
| C07C 211/61 | (2006.01) |
| C07D 405/12 | (2006.01) |
| C07D 239/70 | (2006.01) |
| C07D 209/86 | (2006.01) |
| H01L 51/50 | (2006.01) |

(52) U.S. Cl.
CPC ............ *C07C 211/54* (2013.01); *C07C 211/56* (2013.01); *C07C 211/58* (2013.01); *C07C 211/61* (2013.01); *C07C 255/58* (2013.01); *C07D 209/86* (2013.01); *C07D 213/38* (2013.01); *C07D 213/74* (2013.01); *C07D 239/70* (2013.01); *C07D 307/91* (2013.01); *C07D 333/76* (2013.01); *C07D 401/12* (2013.01); *C07D 403/12* (2013.01); *C07D 405/12* (2013.01); *H01L 51/006* (2013.01); *H01L 51/0052* (2013.01); *H01L 51/0059* (2013.01); *H01L 51/0061* (2013.01); *C07C 2103/18* (2013.01); *C07C 2103/40* (2013.01); *C07C 2103/94* (2013.01); *H01L 51/0054* (2013.01); *H01L 51/5056* (2013.01); *H01L 51/5088* (2013.01)

(58) Field of Classification Search
None
See application file for complete search history.

(56) References Cited

U.S. PATENT DOCUMENTS

| | | | |
|---|---|---|---|
| 4,356,429 | A | 10/1982 | Tang |
| 4,885,211 | A | 12/1989 | Tang et al. |
| 5,151,629 | A | 9/1992 | VanSlyke |
| 5,635,308 | A | 6/1997 | Inoue et al. |
| 5,972,247 | A | 10/1999 | Shi et al. |
| 6,465,115 | B2 | 10/2002 | Shi et al. |
| 6,596,415 | B2 | 7/2003 | Shi et al. |
| 7,833,635 | B2 | 11/2010 | Park et al. |
| 7,854,999 | B2 | 12/2010 | Park et al. |

(Continued)

FOREIGN PATENT DOCUMENTS

| | | |
|---|---|---|
| JP | 05-234681 | 9/1993 |
| JP | 8-12600 | 1/1996 |

(Continued)

OTHER PUBLICATIONS

U.S. Office action dated Apr. 6, 2011, for cross reference U.S. Appl. No. 12/076,776, (8 pages).

(Continued)

*Primary Examiner* — Andrew K Bohaty
(74) *Attorney, Agent, or Firm* — Lewis Roca Rothgerber Christie LLP

(57) ABSTRACT

Embodiments of the present disclosure are directed to a compound represented by Formula 1, and to organic light-emitting diodes including the compound. In some embodiments, an organic light-emitting diode includes a first electrode, a second electrode, and an organic layer between the first electrode and the second electrode and including the compound represented by Formula 1

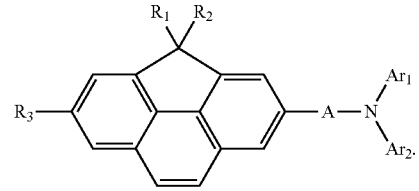

Formula 1

19 Claims, 1 Drawing Sheet

(56) References Cited

U.S. PATENT DOCUMENTS

| | | | |
|---|---|---|---|
| 7,875,367 | B2 | 1/2011 | Park et al. |
| 2001/0024738 | A1 | 9/2001 | Hawker et al. |
| 2004/0207318 | A1* | 10/2004 | Lee et al. ............... 313/506 |
| 2005/0106418 | A1 | 5/2005 | Kim et al. |
| 2005/0139823 | A1* | 6/2005 | Hirakata et al. ............ 257/40 |
| 2005/0158583 | A1 | 7/2005 | Kim et al. |
| 2007/0290610 | A1* | 12/2007 | Park et al. ............... 313/504 |
| 2009/0092853 | A1* | 4/2009 | Park et al. ............... 428/690 |
| 2009/0200928 | A1* | 8/2009 | Hwang et al. ............ 313/504 |
| 2009/0284140 | A1* | 11/2009 | Osaka et al. ............. 313/504 |

FOREIGN PATENT DOCUMENTS

| | | |
|---|---|---|
| JP | 11-003782 | 1/1999 |
| JP | 11-135261 | 5/1999 |
| JP | 2000-3782 | 1/2000 |
| KR | 10-2007-0119470 | 12/2007 |
| KR | 10-2008-0030260 | 4/2008 |
| KR | 10-2008-0036483 | 4/2008 |
| KR | 10-2008-0039057 | 5/2008 |
| KR | 10-2008-0079095 A | 8/2008 |
| KR | 10-2010-0026373 | 3/2010 |

OTHER PUBLICATIONS

U.S. Office action dated Oct. 28, 2011, for cross reference U.S. Appl. No. 12/076,776, (9 pages).

U.S. Office action dated Jun. 29, 2012, for cross reference U.S. Appl. No. 12/076,776, (14 pages).

Kuwabara, et al., *Thermally Stable Multilayered Organic Electrolunimescent Devices Using Novel Starburst Molecules, 4,4',4'-Tri(N-carbazolyl)triphenylamine (TCTA) and 4,4', 4'-Tris (3-methylphenylphenyl-amino)triphenylamine (m-MTDATA), as Hole-Transport Materials*, Advanced Materials, Sep. 1994, vol. 6, No. 9, pp. 677-679.

Patent Abstracts of Japan, and English machine translation of Japanese Publication 11-135261 dated May 21, 1999, listed above, (37 pages).

* cited by examiner

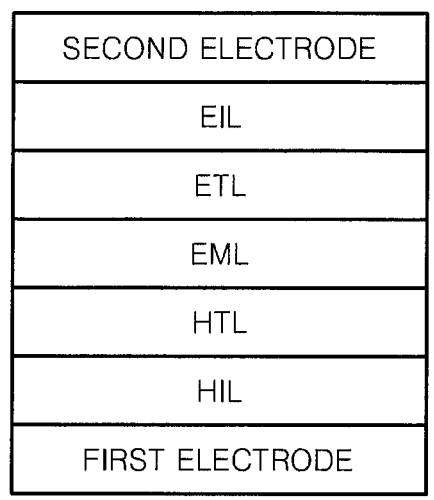

COMPOUND FOR ORGANIC LIGHT-EMITTING DEVICE AND ORGANIC LIGHT-EMITTING DEVICE INCLUDING THE SAME

CROSS-REFERENCE TO RELATED APPLICATION

This application claims priority to and the benefit of Korean Patent Application No. 10-2012-0062860, filed on Jun. 12, 2012 in the Korean Intellectual Property Office, the entire content of which is incorporated herein by reference.

BACKGROUND

1. Technical Field

One or more embodiments of the present invention relate to a compound for an organic light-emitting device and an organic light-emitting device including the compound.

2. Description of the Related Art

Organic light-emitting diodes (OLEDs) are self-emitting devices having advantages such as wide viewing angles, good contrast, quick response speeds, high brightness, and good driving voltage. OLEDs can provide multicolored images. In general, an OLED has a structure including a substrate on which is stacked (in sequential order) an anode, a hole transport layer (HTL), an emission layer (EML), an electron transport layer (ETL), and a cathode. In this regard, the HTL, the EML, and the ETL are organic thin films formed of organic compounds.

An operating principle of an OLED having the above-described structure is as follows. When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

One of the most important factors for determining the luminous efficiency of an OLED is the inclusion of a material having hole injection ability or a material having hole transport ability. However, OLEDs including such materials known in the art do not exhibit satisfactory efficiency, driving voltage and lifetime.

SUMMARY

Embodiments of the present invention provide novel compounds for an organic light-emitting diode which have good electrical properties, high charge transporting abilities, and high glass transition temperatures. The compounds are capable of preventing crystallization, and may be used as hole injection materials or hole transport materials suitable for use in fluorescent and phosphorescent devices of all colors, such as red, green, blue, white, and the like. The hole injection materials or hole transport materials have higher luminous efficiency and longer lifetime than conventional hole injection materials or conventional hole transport materials.

Embodiments of the present invention also provide an organic light-emitting diode including the compound described above and having high efficiency, low voltage, high brightness, and long lifetime.

According to an aspect of the present invention, a compound having hole injection ability and/or hole transport ability is represented by Formula 1 below:

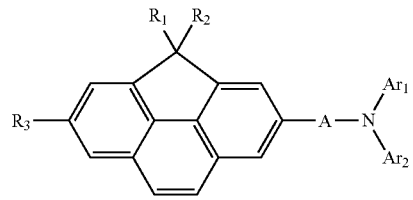

Formula 1

In Formula 1, $R_1$ and $R_2$ are each independently a halogen group, a cyano group, a substituted or unsubstituted $C_1$-$C_{60}$ alkyl group, a substituted or unsubstituted $C_6$-$C_{60}$ aryl group, a substituted or unsubstituted $C_3$-$C_{60}$ heteroaryl group, or a substituted or unsubstituted $C_6$-$C_{60}$ condensed polycyclic group.

$R_3$ is hydrogen, deuterium, a halogen group, a cyano group, a substituted or unsubstituted $C_6$-$C_{60}$ aryl group, a substituted or unsubstituted $C_3$-$C_{60}$ heteroaryl group, or a substituted or unsubstituted $C_6$-$C_{60}$ condensed polycyclic group.

A is a linking group such as a substituted or unsubstituted $C_6$-$C_{10}$ arylene group, a substituted or unsubstituted $C_2$-$C_{11}$ heteroarylene group, or a linking group in which at least two of the arylene groups and/or the heteroarylene groups are linked.

$Ar_1$ and $Ar_2$ are each independently a substituted or unsubstituted $C_6$-$C_{60}$ aryl group, a substituted or unsubstituted $C_3$-$C_{60}$ heteroaryl group, or a substituted or unsubstituted $C_6$-$C_{60}$ condensed polycyclic group.

According to another aspect of the present invention, an organic light-emitting diode includes a first electrode; a second electrode; and an organic layer between the first electrode and the second electrode. The organic layer includes the compound described above.

According to another aspect of the present invention, a flat panel display device includes the organic light-emitting diode, and a first electrode of the organic light-emitting diode is electrically connected to a source electrode or a drain electrode of a thin film transistor.

BRIEF DESCRIPTION OF THE DRAWINGS

The above and other features and advantages of the present invention will become more apparent by reference to the following detailed description when considered in conjunction with the attached drawing in which:

FIG. 1 is a schematic diagram illustrating a structure of an organic light-emitting diode according to an embodiment of the present invention.

DETAILED DESCRIPTION

Hereinafter, exemplary embodiments of the present invention will be described. As used herein, the term "and/or" includes any and all combinations of one or more of the associated listed items. Expressions such as "at least one of," when preceding a list of elements, modify the entire list of elements and do not modify the individual elements of the list.

According to an embodiment of the present invention, a compound represented by Formula 1 below is provided:

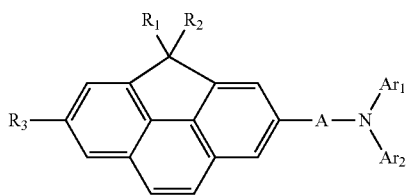

Formula 1

In Formula 1, $R_1$ and $R_2$ are each independently a halogen group, a cyano group, a substituted or unsubstituted $C_1$-$C_{60}$ alkyl group, a substituted or unsubstituted $C_6$-$C_{60}$ aryl group, a substituted or unsubstituted $C_3$-$C_{60}$ heteroaryl group, or a substituted or unsubstituted $C_6$-$C_{60}$ condensed polycyclic group.

$R_3$ is hydrogen, deuterium, a halogen group, a cyano group, a substituted or unsubstituted $C_6$-$C_{60}$ aryl group, a substituted or unsubstituted $C_3$-$C_{60}$ heteroaryl group, or a substituted or unsubstituted $C_6$-$C_{60}$ condensed polycyclic group.

A is a single bond or a linking group such as a substituted or unsubstituted $C_6$-$C_{10}$ arylene group, a substituted or unsubstituted $C_2$-$C_{11}$ heteroarylene group, or a linking group in which at least two of the arylene groups and/or the heteroarylene groups are linked.

$Ar_1$ and $Ar_2$ are each independently a substituted or unsubstituted $C_6$-$C_{60}$ aryl group, a substituted or unsubstituted $C_3$-$C_{60}$ heteroaryl group, or a substituted or unsubstituted $C_6$-$C_{60}$ condensed polycyclic group.

The compounds of Formula 1 have higher driving voltages and efficiency than conventional hole transport materials. Thus, an organic light-emitting diode (OLED) including the compound of Formula 1 exhibits good driving lifetime and increased power efficiency. Therefore, an OLED with low power consumption may be manufactured.

The compound of Formula 1 has a linking group A, which has a relatively small aromatic group, such as a substituted or unsubstituted $C_6$-$C_{10}$ arylene group, a substituted or unsubstituted $C_2$-$C_{11}$ heteroarylene group, or a linking group in which at least two of the arylene groups and/or the heteroarylene groups are linked. Due to the linking group A, the compound of Formula 1 has better hole injection or hole transport ability than compounds of Formula 1 containing relatively large aromatic groups (e.g., an anthracenyl group).

The substituents of the compound of Formula 1 will now be described in more detail.

According to one embodiment, in Formula 1, $R_1$ and $R_2$ may be each independently a halogen group, a cyano group, a substituted or unsubstituted $C_1$-$C_{30}$ alkyl group, a substituted or unsubstituted $C_6$-$C_{30}$ aryl group, a substituted or unsubstituted $C_3$-$C_{30}$ heteroaryl group, or a substituted or unsubstituted $C_6$-$C_{30}$ condensed polycyclic group.

$R_3$ may be hydrogen, deuterium, a halogen group, a cyano group, a substituted or unsubstituted $C_6$-$C_{30}$ aryl group, a substituted or unsubstituted $C_6$-$C_{30}$ heteroaryl group, or a substituted or unsubstituted $C_6$-$C_{30}$ condensed polycyclic group.

A may be a linking group such as a substituted or unsubstituted $C_6$-$C_{10}$ arylene group, a substituted or unsubstituted $C_2$-$C_{11}$ heteroarylene group, or a linking group in which at least two of the arylene groups and/or the heteroarylene groups are linked.

$Ar_1$ and $Ar_2$ may be each independently a substituted or unsubstituted $C_6$-$C_{60}$ aryl group, a substituted or unsubstituted $C_3$-$C_{30}$ heteroaryl group, or a substituted or unsubstituted $C_6$-$C_{30}$ condensed polycyclic group.

According to another embodiment, in Formula 1, $R_1$ and $R_2$ may be each independently hydrogen, deuterium, a halogen group, a cyano group, a substituted or unsubstituted $C_1$-$C_{20}$ alkyl group, or any one of Formulae 2a through 2c below:

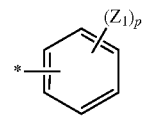

2a

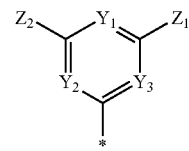

2b

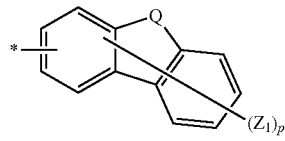

2c

In Formulae 2a through 2c, $Y_1$, $Y_2$, and $Y_3$ are each independently a linking group represented by —N═, or —C($R_{21}$)═.

Q is a linking group represented by —C($R_{30}$)($R_{31}$)—, —N($R_{32}$)—, —S—, or —O—.

$Z_1$, $Z_2$, $R_{21}$, $R_{30}$, $R_{31}$, and $R_{32}$ are each independently a hydrogen atom, deuterium, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, an amino group substituted with a $C_6$-$C_{20}$ aryl group or a $C_3$-$C_{20}$ heteroaryl group, a halogen group, a cyano group, a nitro group, a hydroxyl group, or a carboxyl group.

p is an integer of 1 to 7; and * denotes a binding site.

In another embodiment, in Formula 1, $R_3$ may be hydrogen, deuterium, a halogen group, or at least one of Formulae 3a through 3d below:

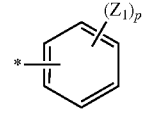

3a

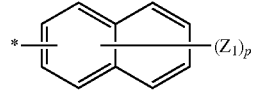

3b

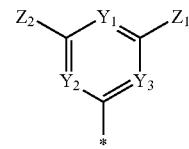

3c

-continued

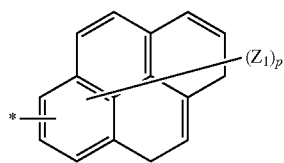
3d

In Formulae 3a through 3d, $Y_1$, $Y_2$, and $Y_3$ are each independently a linking group represented by —N═, or —C($R_{21}$)═.

$Z_1$, $Z_2$, and $R_{21}$ are each independently a hydrogen atom, deuterium, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen group, a cyano group, a nitro group, a hydroxyl group, or a carboxyl group.

p is an integer of 1 to 7; and * denotes a binding site.

According to another embodiment, in Formula 1, A may be a linking group such as any one of Formulae 4a to 4c or a linking group in which at least two groups represented by one or more of Formulae 4a to 4c are linked:

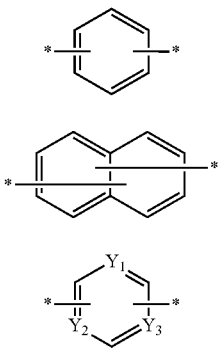

4a

4b

4c

In Formulae 4a to 4c, $Y_1$, $Y_2$, and $Y_3$ are each independently a linking group represented by —N═ or —C($R_{21}$)═. $R_{21}$ is a hydrogen atom, deuterium, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen group, a cyano group, a nitro group, a hydroxyl group, or a carboxyl group.

In another embodiment, in Formula 1, $Ar_1$ and $Ar_2$ may be each independently any one of Formulae 5a to 5e below:

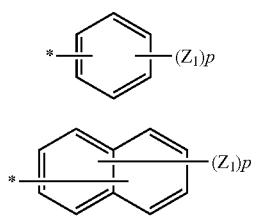

5a

5b

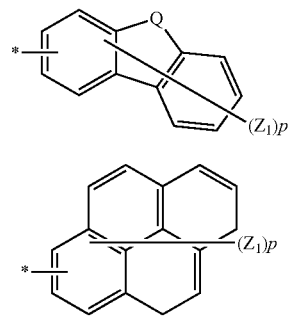

5c

5d

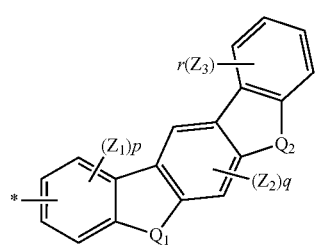

5e

In Formulae 5a to 5e, $Q_1$ and $Q_2$ are each independently a linking group represented by —C($R_{30}$)($R_{31}$)—, —N($R_{32}$)—, —S—, or —O—.

$Z_1$, $Z_2$, $Z_3$, $R_{30}$, $R_{31}$, and $R_{32}$ are each independently a hydrogen atom, deuterium, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, an amino group that is substituted with a $C_6$-$C_{20}$ aryl group or a $C_3$-$C_{20}$ heteroaryl group, a substituted or unsubstituted $C_6$-$C_{20}$ condensed polycyclic group, a halogen group, a cyano group, a nitro group, a hydroxyl group, or a carboxyl group.

p is an integer of 1 to 9; q is 1 or 2; r is an integer of 1 to 4; * denotes a binding site.

According to another embodiment, in Formula 1, $R_1$ and $R_2$ may combine to form a ring.

Hereinafter, representative examples of the substituents used herein will be described. The number of carbon atoms that define the substituents is non-limiting, and do not limit the properties of the substituents.

The unsubstituted $C_1$-$C_{60}$ alkyl group is a linear or branched alkyl group. Examples of the unsubstituted $C_1$-$C_{60}$ alkyl group include methyl, ethyl, propyl, isobutyl, sec-butyl, pentyl, iso-amyl, hexyl, heptyl, octyl, nonanyl, dodecyl, and the like. To obtain a substituted $C_1$-$C_{60}$ alkyl group, at least one hydrogen atom of the unsubstituted $C_1$-$C_{60}$ alkyl group may be substituted with deuterium, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_4$-$C_{16}$ heteroaryl group.

The unsubstituted $C_2$-$C_{60}$ alkenyl group is a group containing at least one carbon-carbon double bond in the center or at a terminal end of the unsubstituted $C_2$-$C_{60}$ alkyl group. Examples of the unsubstituted $C_2$-$C_{60}$ alkenyl group include ethenyl, propenyl, butenyl, and the like. To obtain a substituted $C_2$-$C_{60}$ alkenyl group, at least one hydrogen atom of the unsubstituted $C_2$-$C_{60}$ alkenyl group may be substituted with the substituents described above with respect to the substituted $C_1$-$C_{60}$ alkyl group.

The unsubstituted $C_2$-$C_{60}$ alkynyl group is a group containing at least one carbon-carbon triple bond in the center or at a terminal end of the $C_2$-$C_{60}$ alkyl group defined above. Examples of the unsubstituted $C_2$-$C_{60}$ alkynyl group include acetylene, propylene, phenylacetylene, naphthylacetylene, isopropylacetylene, t-butylacetylene, diphenylacetylene, and the like. To obtain a substituted $C_2$-$C_{50}$ alkynyl group, at least one hydrogen atom of the unsubstituted $C_2$-$C_{60}$ alkynyl group may be substituted with the substituents described above with respect to the substituted $C_1$-$C_{60}$ alkyl group.

The unsubstituted $C_3$-$C_{60}$ cycloalkyl group denotes a $C_3$-$C_{60}$ ring-type alkyl group. To obtain a substituted $C_3$-$C_{60}$ cycloalkyl group, at least one hydrogen atom of the unsubstituted $C_3$-$C_{60}$ cycloalkyl group may be substituted with the substituents described above with respect to the substituted $C_1$-$C_{60}$ alkyl group.

The unsubstituted $C_1$-$C_{60}$ alkoxy group has the Formula —OA in which A is the unsubstituted $C_1$-$C_{60}$ alkyl group. Non-limiting examples of the unsubstituted $C_1$-$C_{60}$ alkoxy group include methoxy, ethoxy, propoxy, isopropyloxy, butoxy, pentoxy, and the like. To obtain a substituted $C_1$-$C_{60}$ alkoxy group, at least one hydrogen atom of the unsubstituted $C_1$-$C_{60}$ alkoxy group may be substituted with the substituents described above with respect to the substituted $C_1$-$C_{60}$ alkyl group.

The unsubstituted $C_6$-$C_{60}$ aryl group refers to a $C_6$-$C_{60}$ carbocyclic aromatic system containing at least one ring. When the $C_6$-$C_{60}$ aryl group contains at least two rings, the rings may be fused with each other or linked to each other by a single bond. The term "aryl" refers to an aromatic system, including phenyl, naphthyl, anthracenyl, and the like. To obtain a substituted $C_6$-$C_{60}$ aryl group, at least one hydrogen atom of the unsubstituted $C_6$-$C_{60}$ aryl group may be substituted with the substituents described above with respect to the substituted $C_1$-$C_{60}$ alkyl group.

Examples of the substituted or unsubstituted $C_6$-$C_{60}$ aryl group include a phenyl group, a $C_1$-$C_{10}$ alkylphenyl group (e.g., an ethylphenyl group), a halophenyl group (e.g., an o-, m- or p-fluorophenyl group, or a dichlorophenyl group), a cyanophenyl group, a dicyanophenyl group, a trifluoromethoxyphenyl group, a biphenyl group, a halobiphenyl group, a cyanobiphenyl group, a $C_1$-$C_{10}$ alkylbiphenyl group, a $C_1$-$C_{10}$ alkoxybiphenyl group, an o-, m-, or p-tolyl group, an o-, m- or p-cumenyl group, a mesityl group, a phenoxyphenyl group, an (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (e.g., a fluoronaphthyl group), a $C_1$-$C_{10}$ alkylnaphthyl group (e.g., a methylnaphthyl group), a $C_1$-$C_{10}$ alkoxynaphthyl group (e.g., a methoxynaphthyl group), a cyanonaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl, a pyranthrenyl group, or an ovalenyl group.

The unsubstituted $C_3$-$C_{60}$ heteroaryl group indicates a group having 1, 2 or 3 hetero atom(s) selected from N, O, P, and S. When the $C_3$-$C_{60}$ heteroaryl group contains at least two rings, the rings may be fused with each other or linked to each other by a single bond. Non-limiting examples of the unsubstituted $C_3$-$C_{60}$ heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, and a dibenzothiophene group. To obtain a substituted $C_3$-$C_{60}$ heteroaryl group, at least one hydrogen atom of the unsubstituted $C_3$-$C_{60}$ heteroaryl group may be substituted with the substituents described above with respect to the substituted $C_1$-$C_{60}$ alkyl group.

The unsubstituted $C_6$-$C_{60}$ aryloxy group has the formula —$OA_1$ in which $A_1$ is the $C_6$-$C_{60}$ aryl group as described above. Non-limiting examples of the unsubstituted $C_6$-$C_{60}$ aryloxy group include a phenoxy group and the like. To obtain a substituted $C_6$-$C_{60}$ aryloxy group, at least one hydrogen atom of the unsubstituted $C_6$-$C_{60}$ aryloxy group may be substituted with the substituents described above with respect to the substituted $C_1$-$C_{60}$ alkyl group.

The unsubstituted $C_6$-$C_{60}$ arylthio group has the formula —$SA_1$ in which $A_1$ is the $C_6$-$C_{60}$ aryl group described above. Non-limiting examples of the unsubstituted $C_6$-$C_{60}$ arylthio group may include a benzylthio group, a naphthylthio group, and the like. To obtain a substituted $C_6$-$C_{60}$ arylthio group, at least one hydrogen atom of the unsubstituted $C_6$-$C_{60}$ arylthio group may be substituted with the substituents described above with respect to the substituted $C_1$-$C_{60}$ alkyl group.

The unsubstituted $C_6$-$C_{60}$ condensed polycyclic group indicates a substituent having at least two rings in which at least one aromatic ring and at least one non-aromatic ring are fused with each other, or a substituent having an unsaturated group but not having a conjugated system in the ring. The unsubstituted $C_6$-$C_{60}$ condensed polycyclic group differs from the aryl and heteroaryl groups in that it is overall non-aromatic.

In some embodiments, the compound of Formula 1 may be one of Compounds 1 through 88 below, but is not limited thereto.

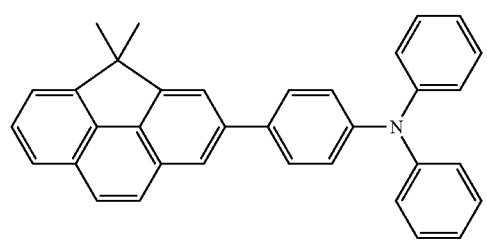

1

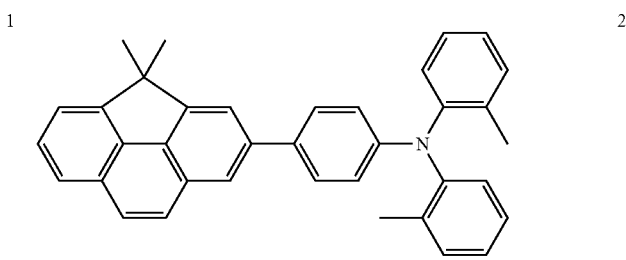

2

-continued
3
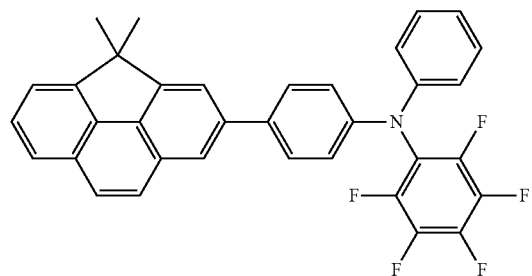
4
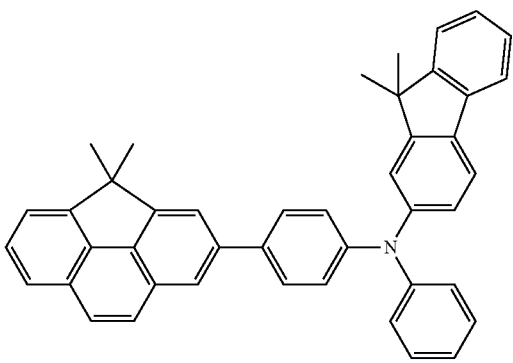
5
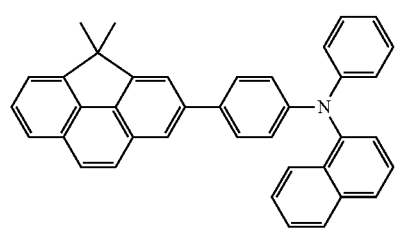
6
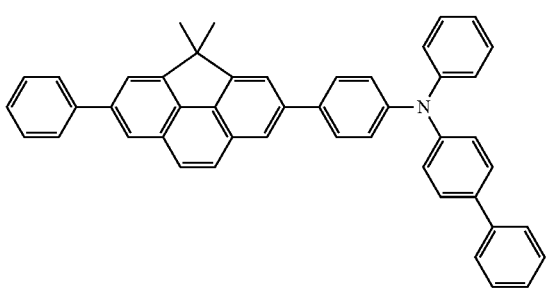
7
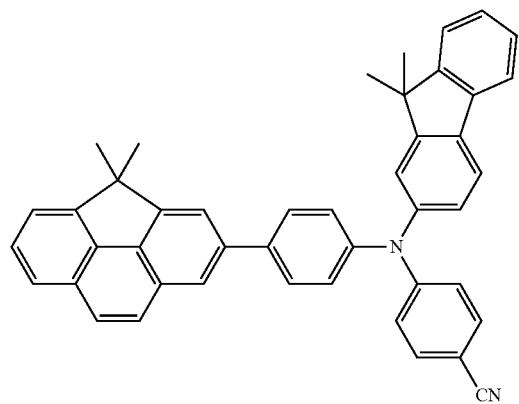
8
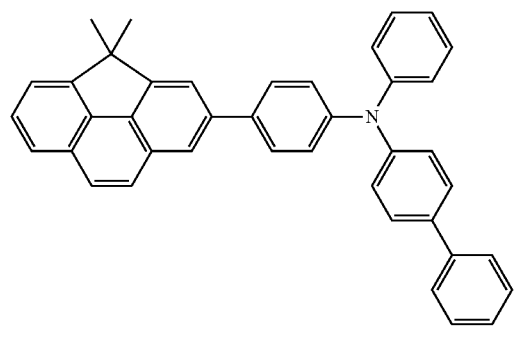
9
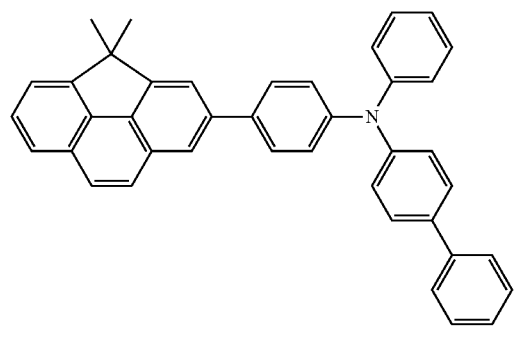
10
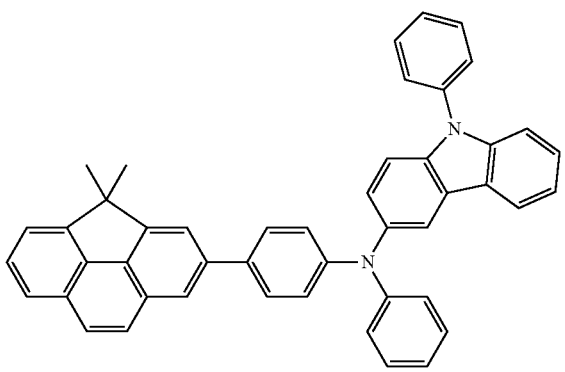

-continued

-continued
19
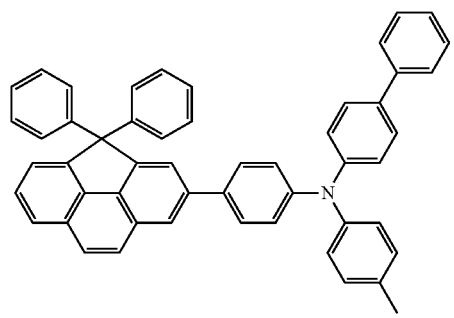
20
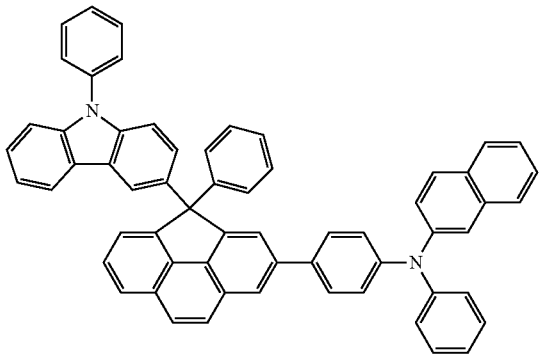
21
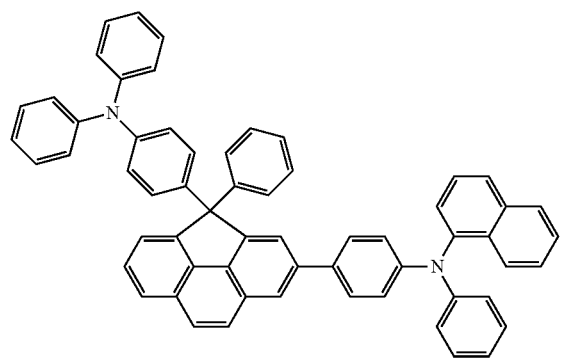
22
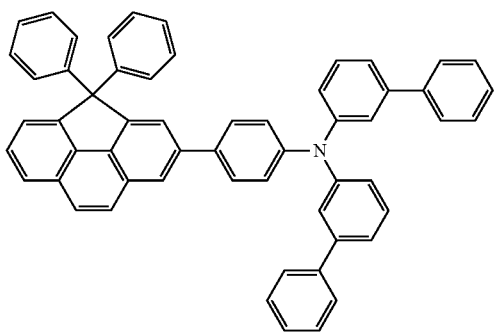
23
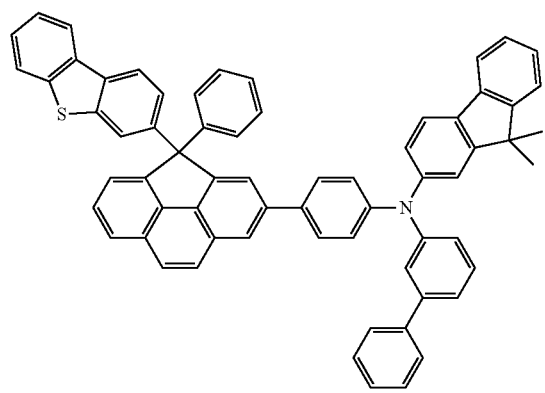
24
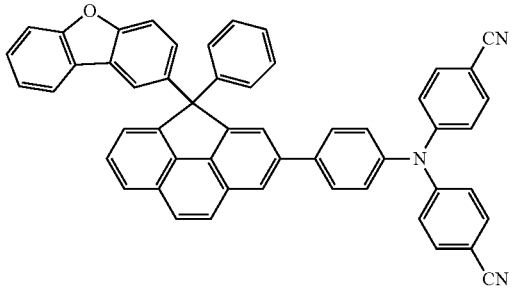
25
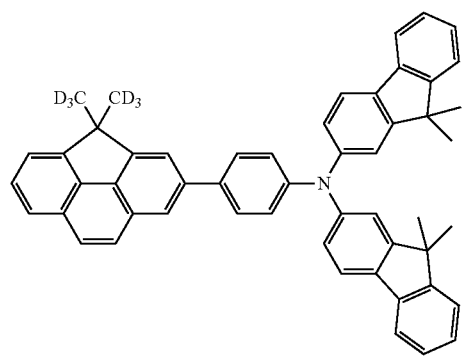
26
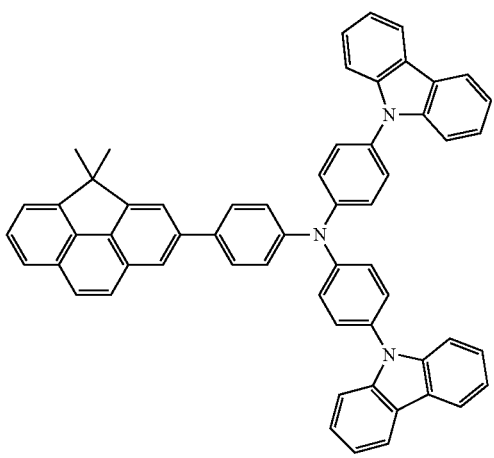

-continued
27
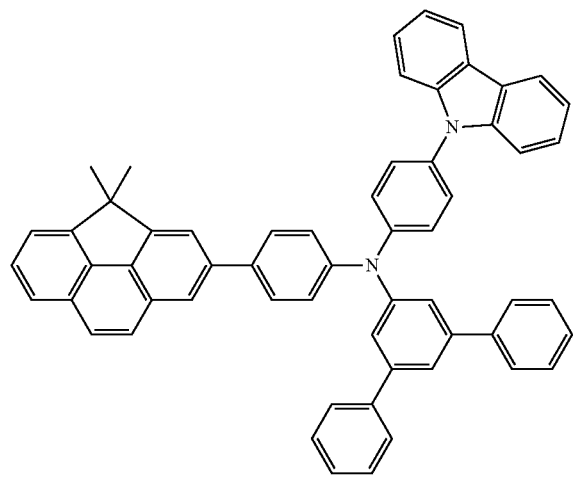
28
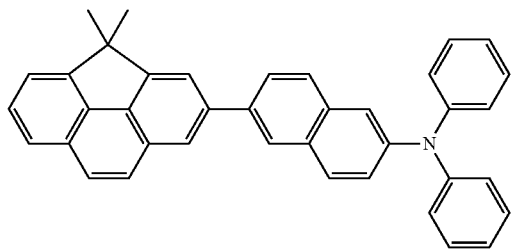
29
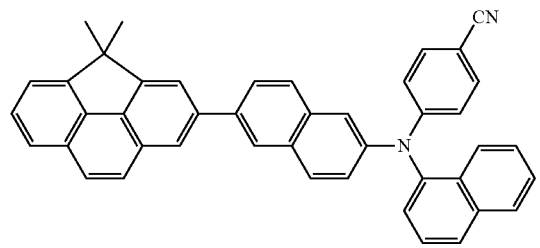
30
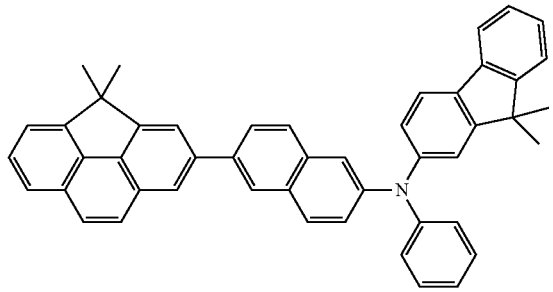
31
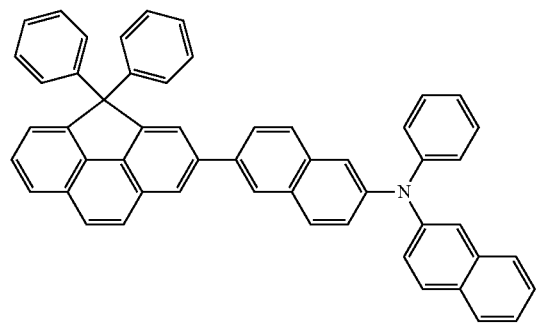
32
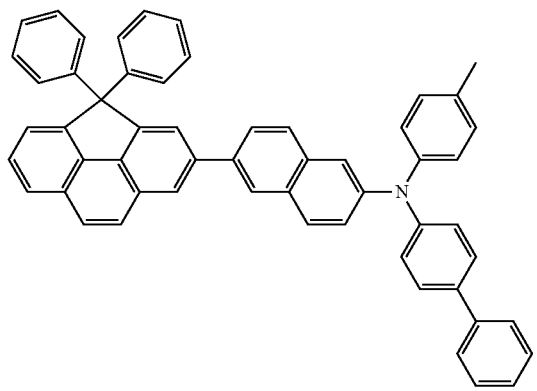
33
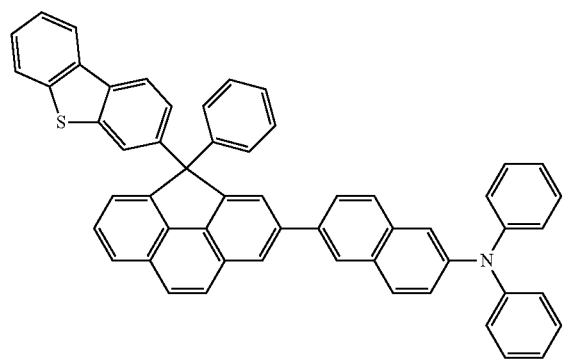
34
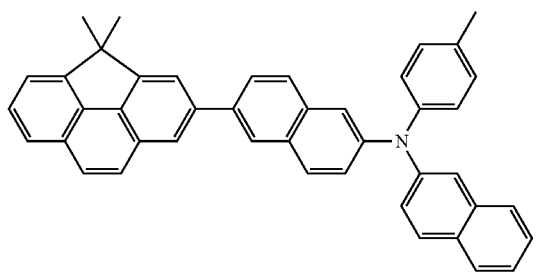

-continued
35
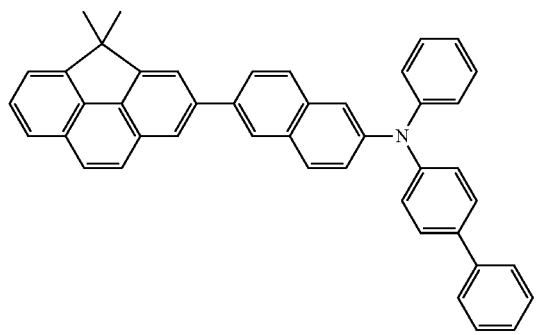
36
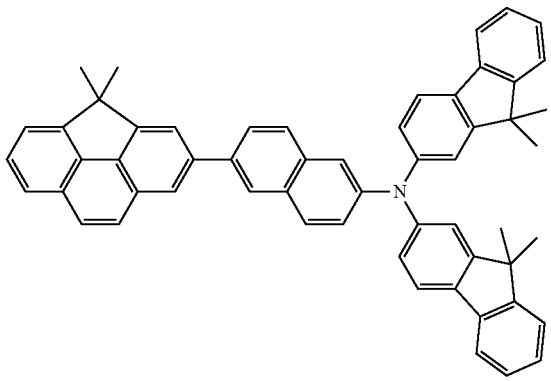
37
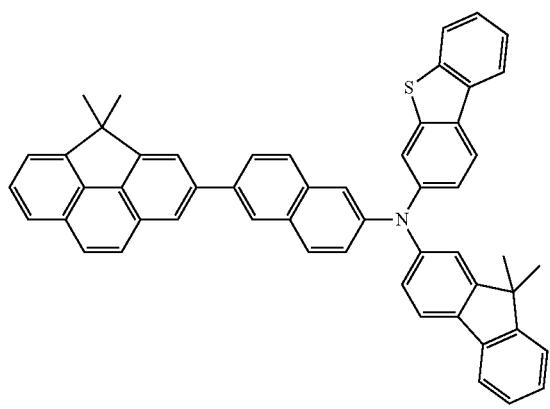
38
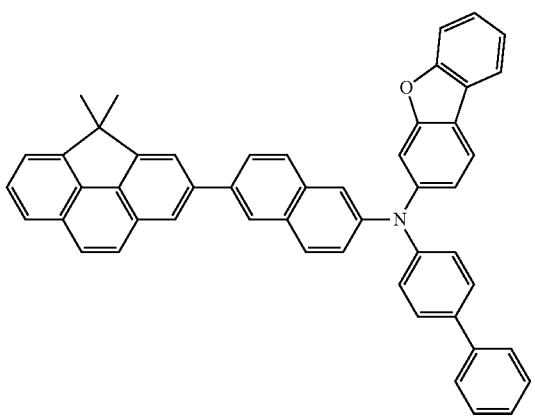
39
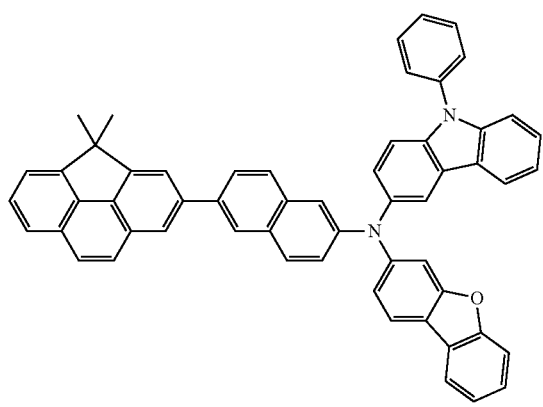
40
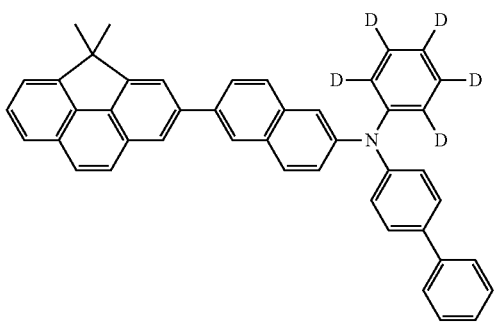
41
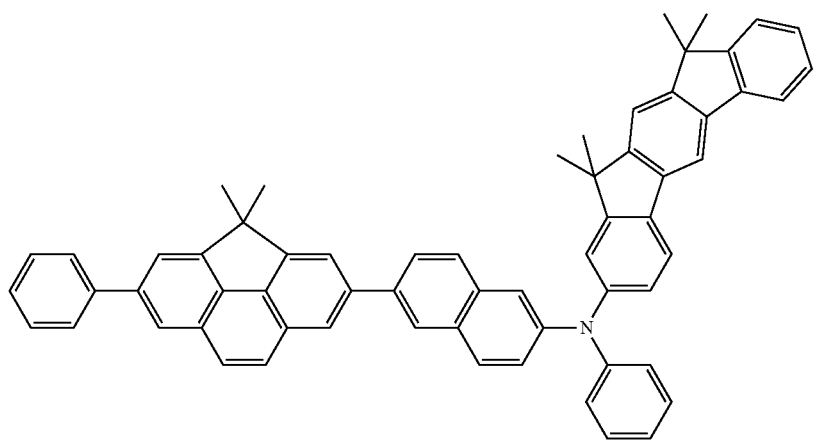

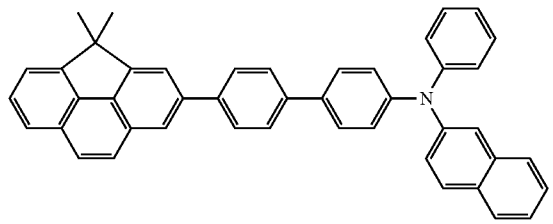
42
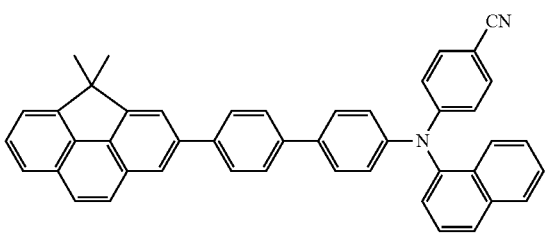
43
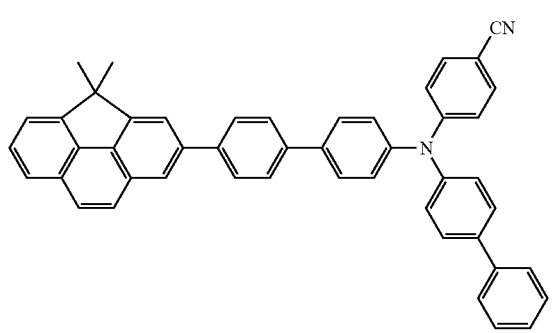
44
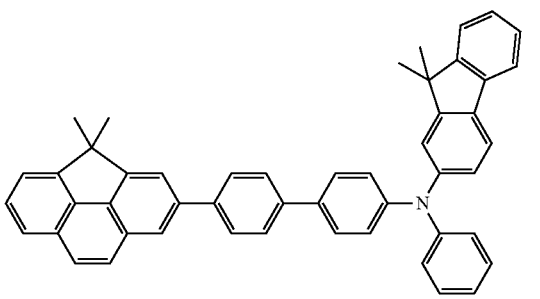
45
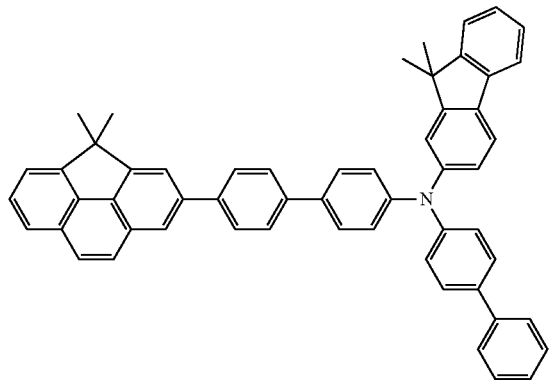
46
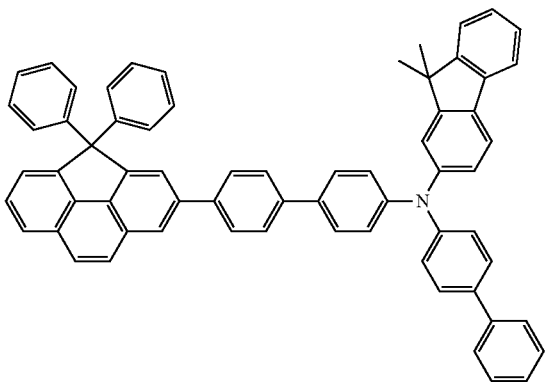
47
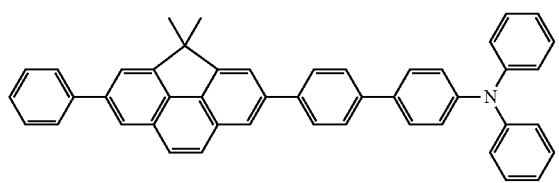
48
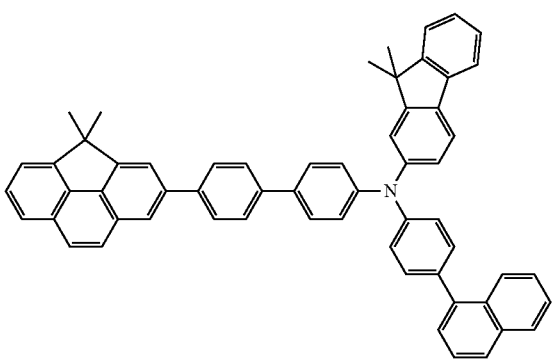
49

-continued
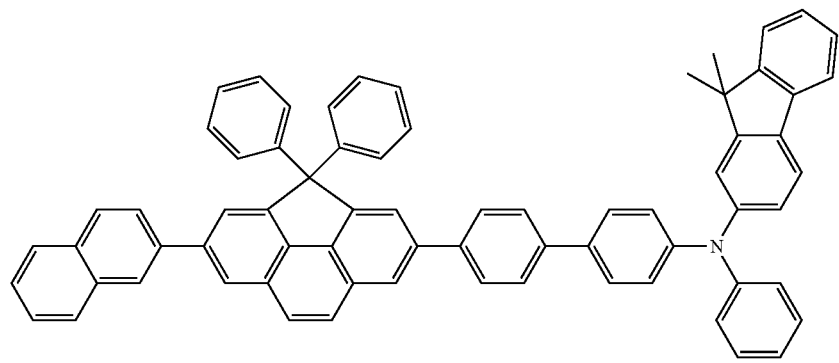
50
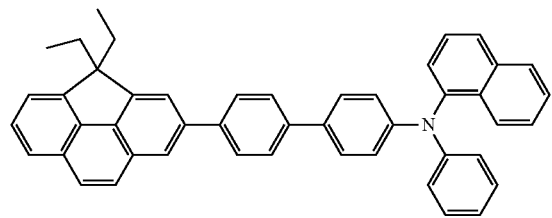
51
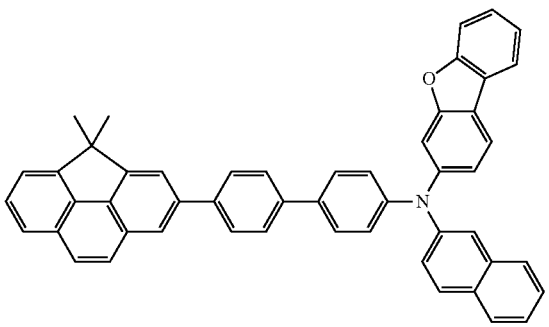
52
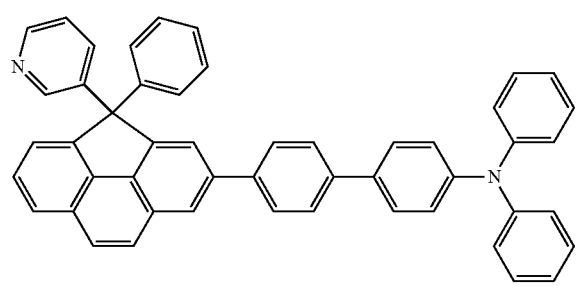
53
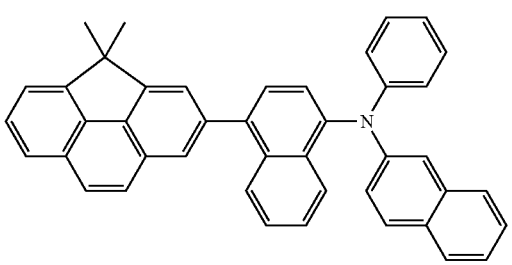
54
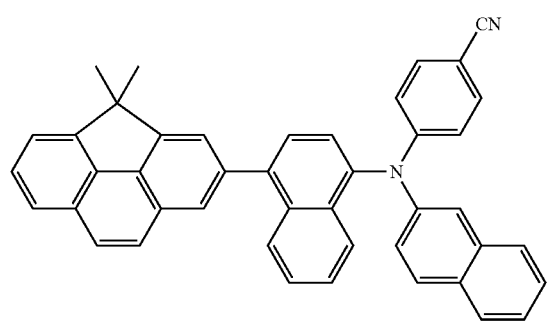
55
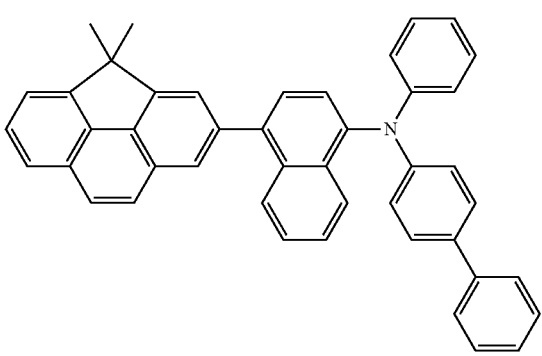
56

-continued
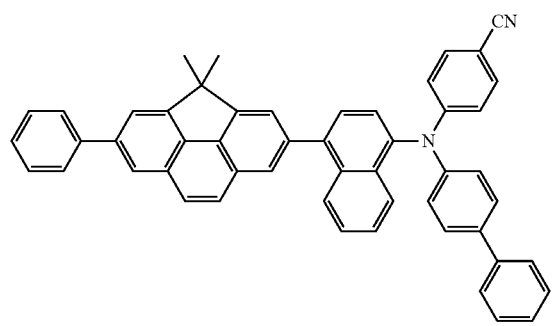
57
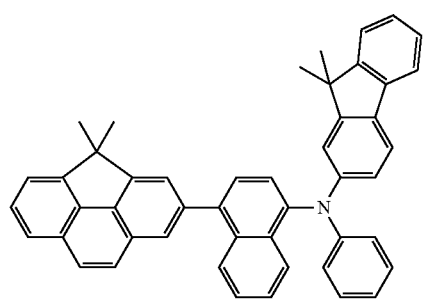
58
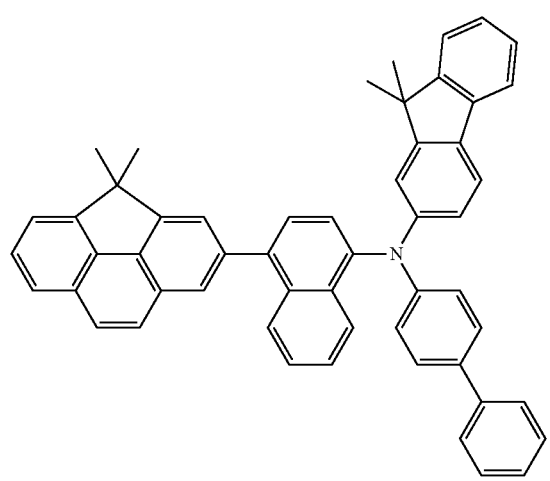
59
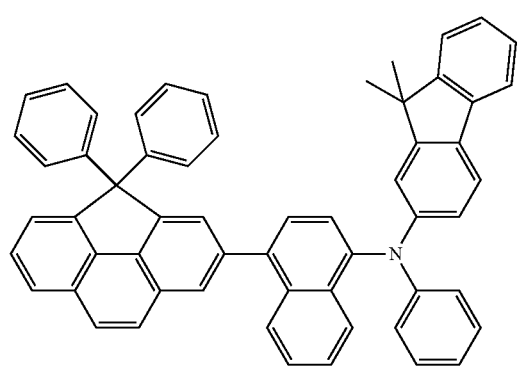
60
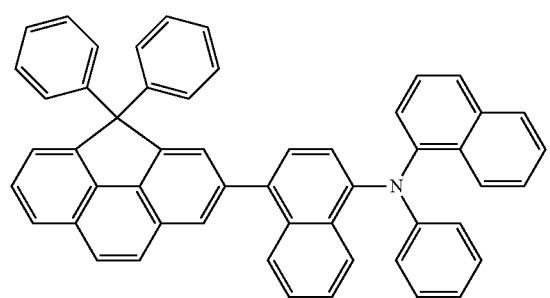
61
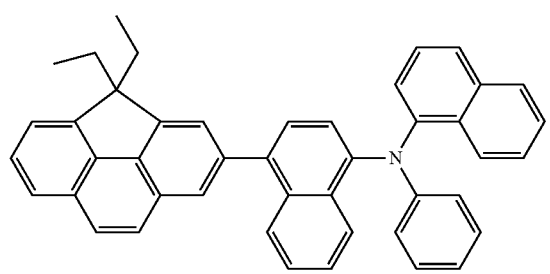
62
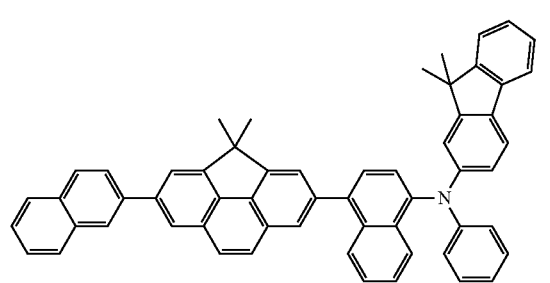
63
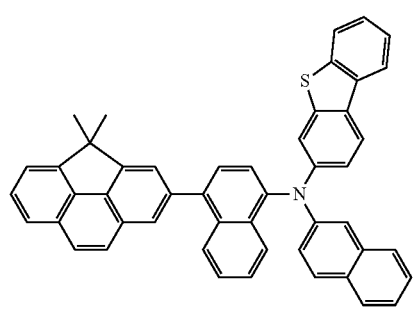
64

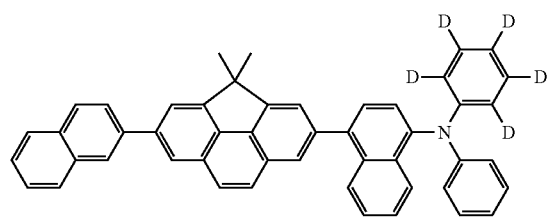
65
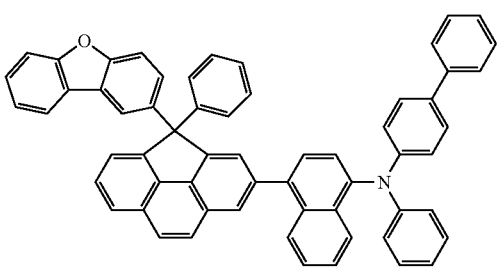
66
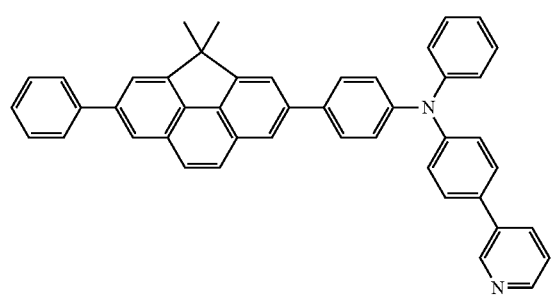
67
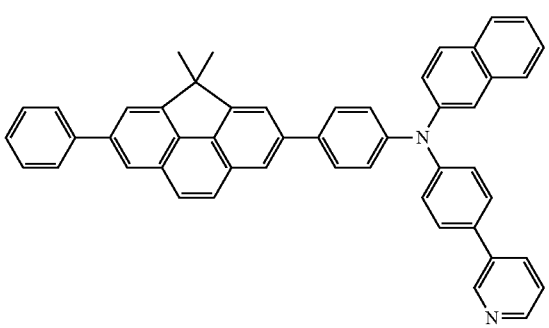
68
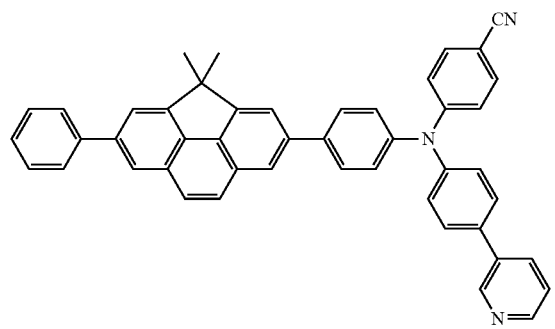
69
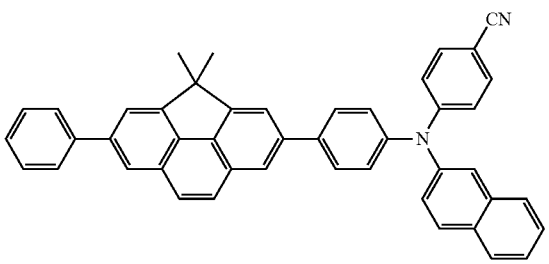
70
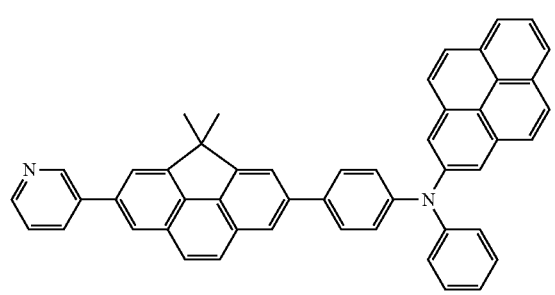
71
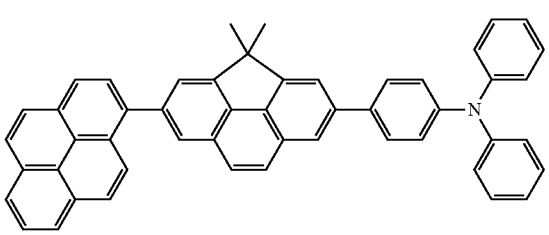
72
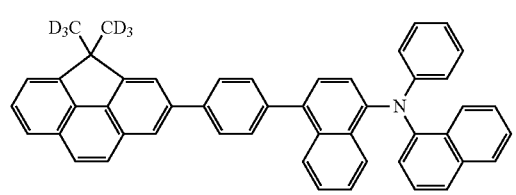
73
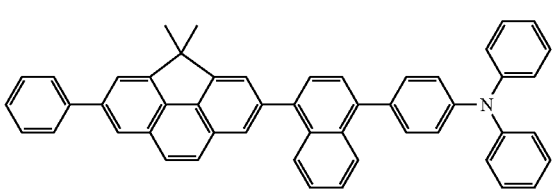
74

-continued
| | |
|---|---|
| 75 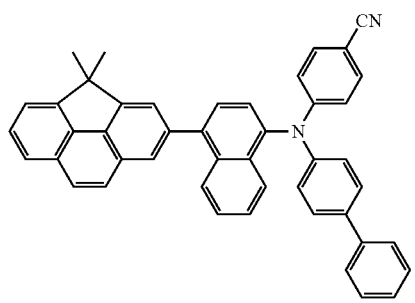 | 76 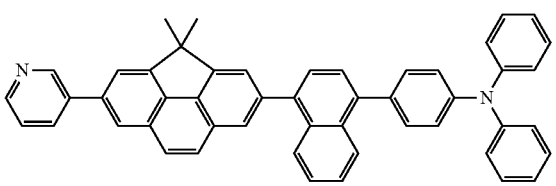 |
| 77 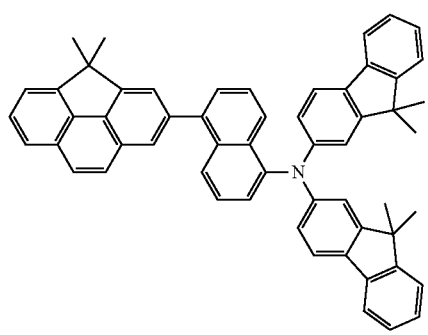 | 78 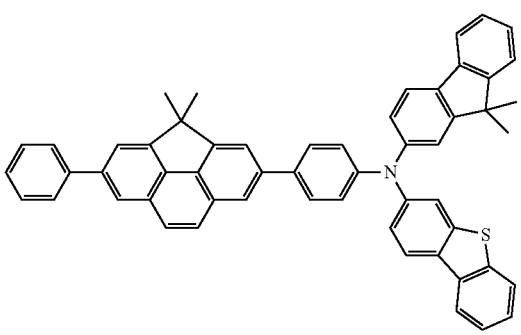 |
| 79 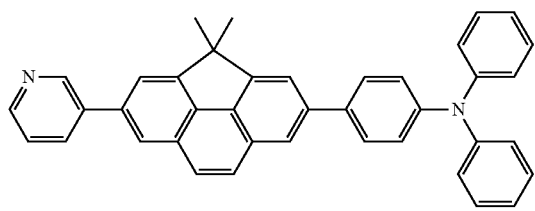 | 80 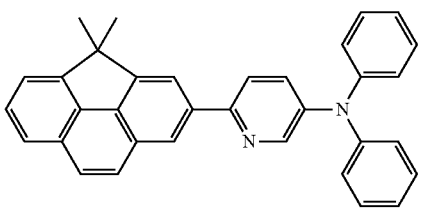 |
| 81 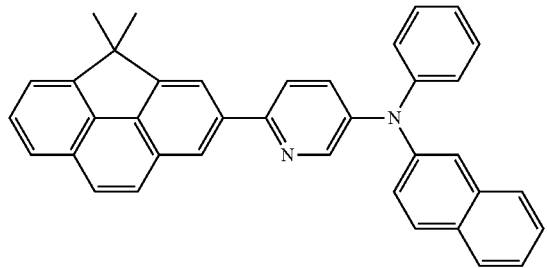 | 82 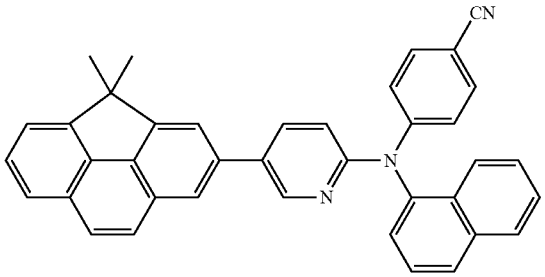 |
| 83 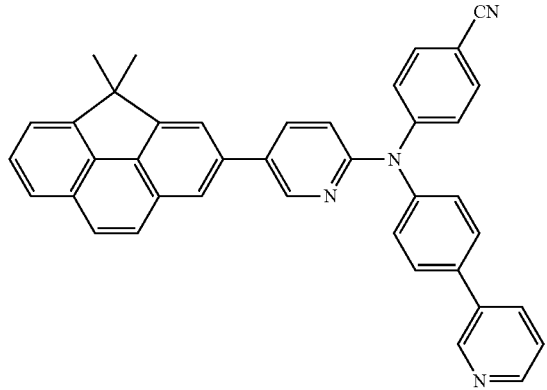 | 84 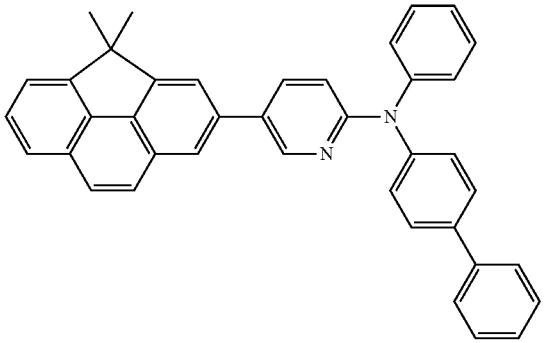 |

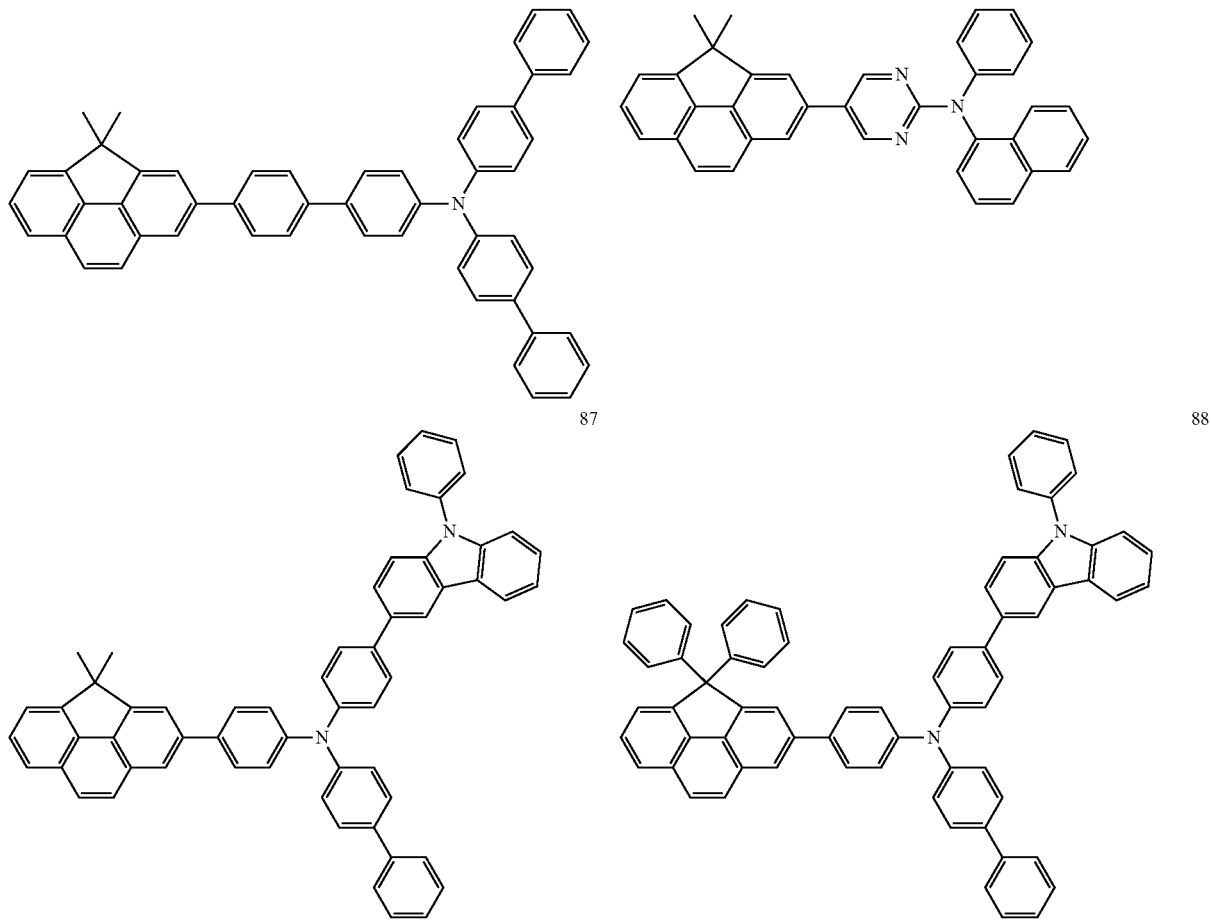

According to another embodiment of the present invention, an OLED includes a first electrode; a second electrode; and an organic layer between the first electrode and the second electrode. The organic layer includes the compound of Formula 1 described above.

The organic layer may include at least one of a hole injection layer (HIL), a hole transport layer (HTL), a functional layer having both hole injection and hole transport abilities (hereinafter, referred to as an "H-functional layer"), a buffer layer, an electron blocking layer (EBL), an emission layer (EML), a hole blocking layer (HBL), an electron transport layer (ETL), an electron injection layer (EIL), or a functional layer having both electron transport and electron injection abilities (hereinafter, referred to as an "E-functional layer").

In some embodiments, the organic layer may be a HIL, a HTL, or a H-functional layer. For example, the organic layer may be a HTL or a HIL.

In one embodiment, the OLED may include an EIL, an ETL, an EML, a HIL, a HTL, or an H-functional layer. The EML may include the compound of Formula 1; and an anthracene-based compound, an arylamine-based compound, or a styryl-based compound.

In another embodiment, the OLED may include an EIL, an ETL, an EML, a HIL, a HTL, or an H-functional layer, and the HIL, the HTL, or the H-functional layer may include the compound of Formula 1 (which has hole injection ability and/or hole transport ability). Any one of a red layer, a green layer, a blue layer, or a white layer of the EML may include a phosphorescent compound.

Also, the HIL, the HTL, or the H-functional layer may include a charge-generating material. In this regard, the charge-generating material may be a p-dopant. Examples of the p-dopant include quinone derivatives, metal oxides, and cyano-containing compounds.

In another embodiment, the organic layer may include an ETL, and the ETL may include an electron transporting organic compound and a metal complex. The metal complex may be a Li complex.

The term "organic layer" as used herein refers to a single layer and/or a plurality of layers positioned between the first electrode and the second electrode.

The organic layer may include at least one of a HIL, a HTL, or an H-functional layer, and at least one of the HIL, the HTL, or the H-functional layer may include the compound of Formula 1.

FIG. 1 is a schematic diagram illustrating the structure of an OLED according to an embodiment of the present invention. Hereinafter, a structure and manufacturing method of an OLED will be described with reference to FIG. 1.

The substrate (not shown) may be any substrate generally used in OLEDs, and may be, for example, a glass substrate or a transparent plastic substrate having good mechanical strength, thermal stability, transparency, surface smoothness, ease of handling, and waterproofness.

The first electrode may be formed by applying a first electrode material on the substrate by deposition or sputtering. When the first electrode is an anode, the first electrode material may be selected from materials having a high work function so as to facilitate hole injection. The first electrode may be a reflective electrode or a transparent electrode. Non-limiting examples of the first electrode material include indium-tin oxide (ITO), indium-zinc-oxide (IZO), tin oxide ($SnO_2$), and zinc oxide (ZnO), which are transparent and have high conductivity. Also, when magnesium (Mg), aluminum (Al), aluminum-lithium (Al—Li), calcium (Ca), magnesium-indium (Mg—In), or magnesium-silver (Mg—Ag) is used as the first electrode material, the first electrode may be formed as a reflective electrode.

The first electrode may be formed as a single layer or have a multi-layered structure with at least two layers. For example, the first electrode may have a three-layered structure including ITO/Ag/ITO, but is not limited thereto.

The organic layer is formed on the first electrode.

The organic layer may include a HIL, a HTL, a buffer layer (not shown), an EML, an ETL, or an EIL.

The HIL may be formed on the first electrode by various methods such as vacuum deposition, spin coating, casting, or LB deposition.

When the HIL is formed by vacuum deposition, the deposition conditions may vary according to the compound used as the material for forming the HIL, the structure of the desired HIL, and the thermal characteristics. For example, the deposition conditions may be, but are not limited to, a deposition temperature of about 100° C. to about 500° C., a degree of vacuum of about $10^{-8}$ torr to about $10^{-3}$ torr, and a deposition speed of about 0.01 Å/sec to about 100 Å/sec.

When the HIL is formed by spin coating, the coating conditions may vary according to the compound used as the material for forming the HIL, the structure of the desired HIL, and the thermal characteristics. For example, the coating conditions may be, but are not limited to, a coating speed of about 2,000 rpm to about 5,000 rpm and a heat treatment temperature for removing the solvent after coating of about 80° C. to about 200° C.

The material for forming the HIL may be a compound according to an embodiment of the present invention or a known hole injection material. Non-limiting examples of the hole injection material include, but are not limited to, N,N'-diphenyl-N,N'-bis-[4-(phenyl-m-tolyl-amino)-phenyl]biphenyl-4,4'-diamine (DNTPD), a phthalocyanine compound such as copper phthalocyanine, 4,4',4''-tris(3-methylphenylphenylamino)triphenylamine (m-MTDATA), N,N'-di(1-naphthyl)-N,N'-diphenylbenzidine (NPB), TDATA, 2-TNATA, polyaniline/dodecylbenzenesulfonic acid (Pani/DBSA), poly(3,4-ethylenedioxythiophene)/poly(4-styrene-sulfonate) (PEDOT/PSS), polyaniline/camphor sulfonicacid (Pani/CSA), and (polyaniline)/poly(4-styrenesulfonate) (PANI/PSS):

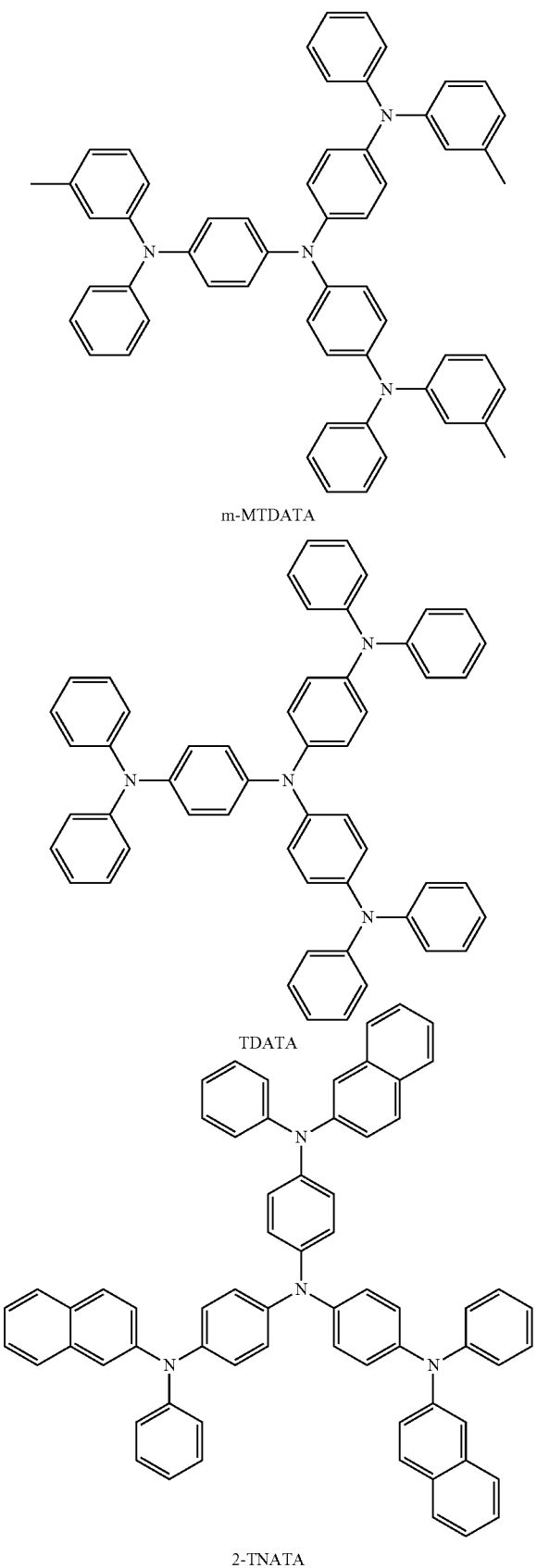

m-MTDATA

TDATA

2-TNATA

The thickness of the HIL may be about 100 Å to about 10,000 Å. In some embodiments, the thickness of the HIL may be about 100 Å to about 1,000 Å. When the thickness of the HIL is within these ranges, satisfactory hole injection properties may be obtained without a substantial increase in driving voltage.

Next, the HTL may be formed on the HIL by various methods, such as vacuum deposition, spin coating, casting, or LB deposition. When the HTL is formed by vacuum deposition or spin coating, the deposition or coating conditions may vary according to the compounds used. However, in general, the deposition or coating conditions may be similar or identical to the conditions used for forming the HIL.

A material for forming the HTL may be a compound according to an embodiment of the present invention or a known hole transporting material. Non-limiting examples of the hole transporting material include, but are not limited to, carbazole derivatives such as N-phenylcarbazole and polyvinylcarbazole, N,N'-bis(3-methylphenyl)-N,N-diphenyl-[1,1-biphenyl]-4,4'-diamine (TPD), 4,4',4"-tris(N-carbazolyl) triphenylamine (TCTA), and N,N'-di(1-naphthyl)-N,N'-diphenylbenzidine (NPB).

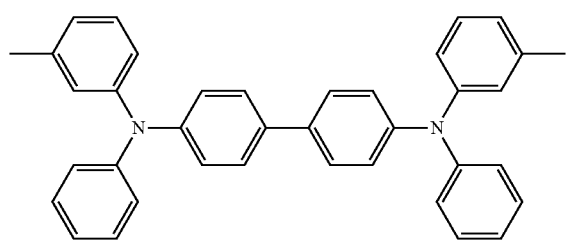

TPD

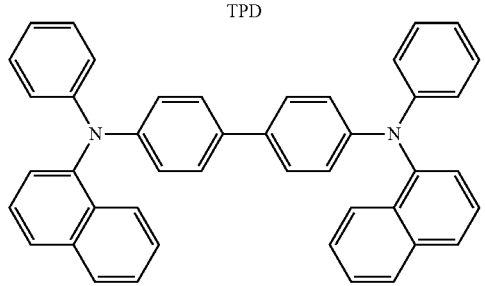

NPD

The thickness of the HTL may be about 50 Å to about 2,000 Å. In some embodiments, the thickness of the HTL may be about 100 Å to about 1,500 Å. When the thickness of the HTL is within these ranges, satisfactory hole transport properties may be obtained without a substantial increase in driving voltage.

The H-functional layer may include at least one of the hole injection materials and the hole transporting materials described above. The thickness of the H-functional layer may be about 500 Å to about 10,000 Å. In some embodiments, the thickness of the H-functional layer may be about 100 Å to about 1,000 Å. When the thickness of the H-functional layer is within these ranges, satisfactory hole injection and hole transport properties may be obtained without a substantial increase in driving voltage.

At least one of the HIL, the HTL, or the H-functional layer may include at least one of a compound represented by Formula 300 below and a compound represented by Formula 350 below:

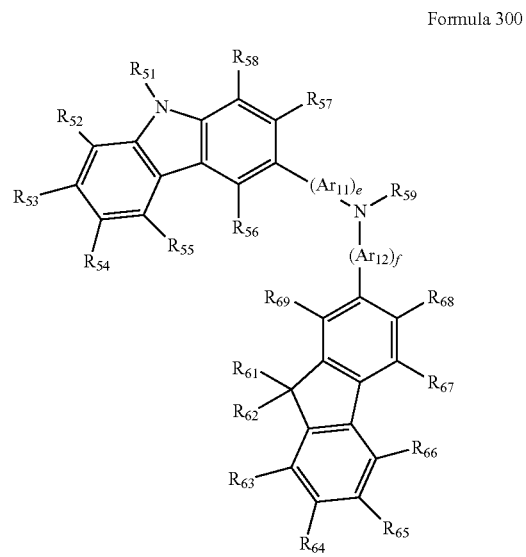

Formula 300

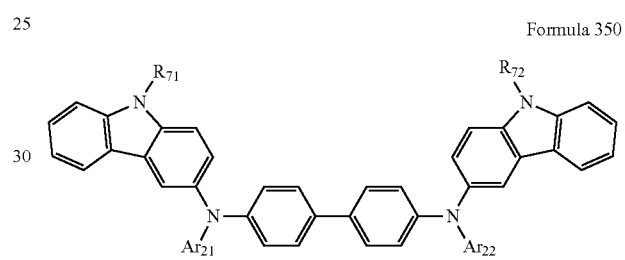

Formula 350

In Formulae 300 and 350, $Ar_{11}$, $Ar_{12}$, $Ar_{21}$, and $Ar_{22}$ are each independently a substituted or unsubstituted $C_6$-$C_{60}$ arylene group. A detailed description of $Ar_{11}$, $Ar_{12}$, $Ar_{21}$, and $Ar_{22}$ is already provided in the description of $Ar_1$ and $Ar_2$ above.

In Formula 300, e and f may be each independently an integer of 0 to 5, for example, 0, 1, or 2. For example, e may be 1 and f may be 0, but e and f are not limited thereto.

In Formulae 300 and 350, $R_{51}$ through $R_{58}$, $R_{61}$ through $R_{69}$, $R_{71}$, and $R_{72}$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, or a substituted or unsubstituted $C_6$-$C_{60}$ arylthio group. For example, $R_{51}$ through $R_{58}$, $R_{61}$ through $R_{69}$, $R_{71}$, and $R_{72}$ may be each independently (but are not limited to) hydrogen; deuterium; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid group or a salt thereof; a $C_1$-$C_{10}$ alkyl group (for example, a methyl group, an ethyl group, a propyl group, a butyl group, a pentyl group, a hexyl group, or the like); a C$_1$-C$_{10}$ alkoxy group (for example, a methoxy group, an ethoxy group, a propoxy group, a butoxy group, a pentoxy group, or the like); a C$_1$-C$_{10}$ alkyl group or a C$_1$-C$_{10}$ alkoxy group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, or a phosphoric acid group or a salt thereof; a phenyl group; a naphthyl group; an anthryl group; a fluorenyl group; a pyrenyl group; or a phenyl group, a naphthyl group, an anthryl group, a fluorenyl group, or a pyrenyl group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a C$_1$-C$_{10}$ alkyl group, or a C$_1$-C$_{10}$ alkoxy group.

In Formula 300, R$_{59}$ may be one of a phenyl group; a naphthyl group; an anthryl group; a biphenyl group; a pyridyl group; or a phenyl group, a naphthyl group, an anthryl group, a biphenyl group or a pyridyl group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a substituted or unsubstituted C$_1$-C$_{20}$ alkyl group, or a substituted or unsubstituted C$_1$-C$_{20}$ alkoxy group.

In one embodiment, the compound of Formula 300 may be a compound represented by Formula 300A below, but is not limited thereto:

Formula 300A

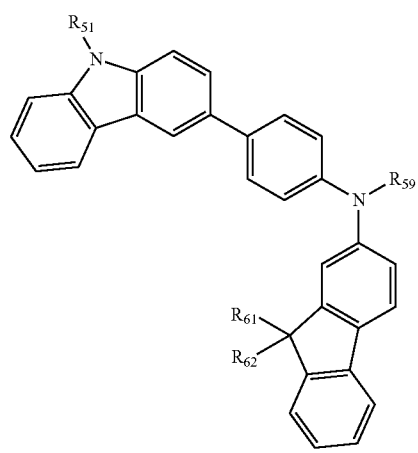

In Formula 300A, R$_{51}$, R$_{60}$, R$_{61}$, and R$_{59}$ are the same as defined above.

For example, at least one of the HIL, the HTL, or the H-functional layer may include at least one of Compounds 301 through 320 below, but is not limited thereto:

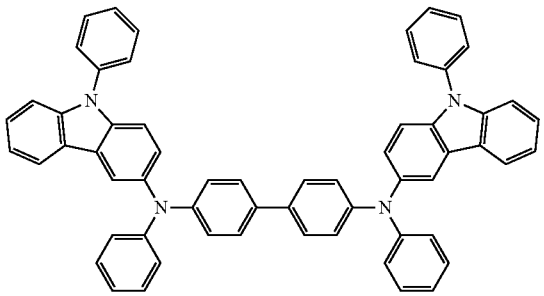

301

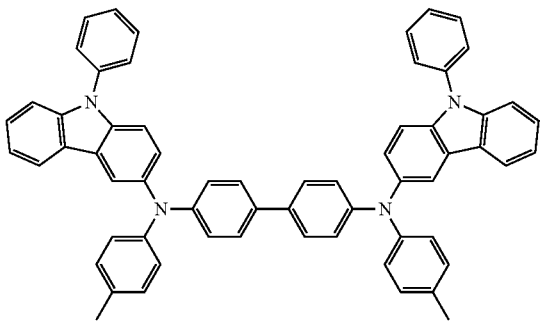

302

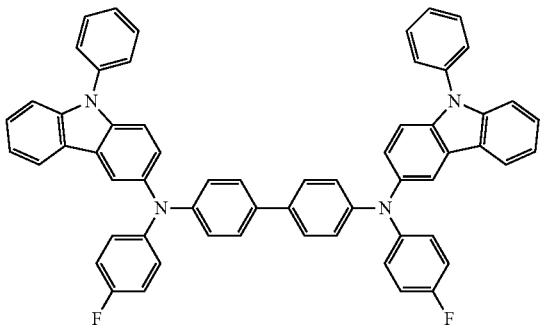

303

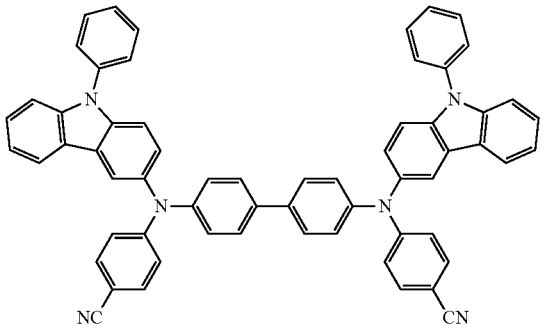

304

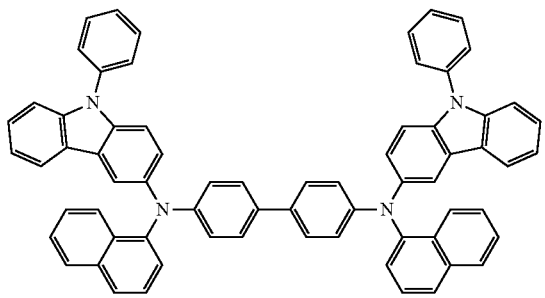
305
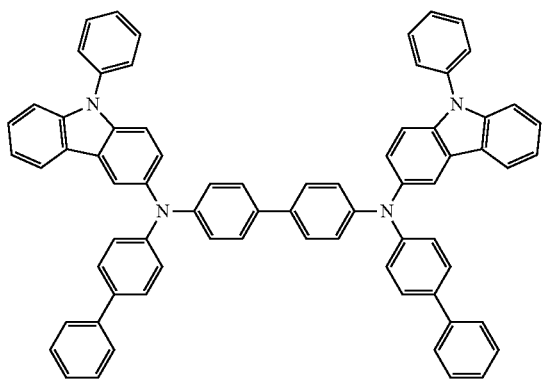
306
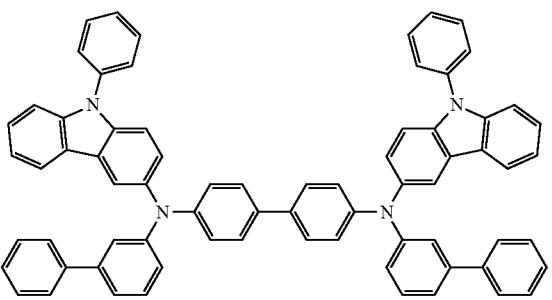
307
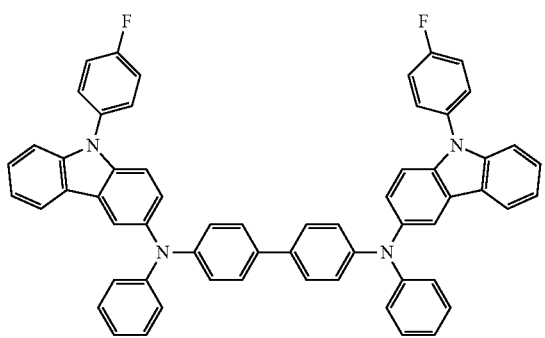
308
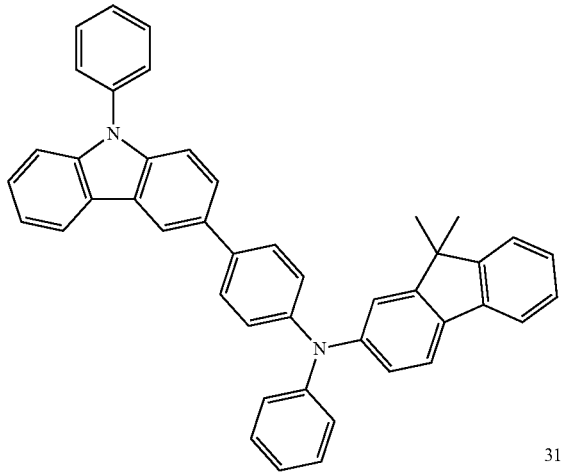
309
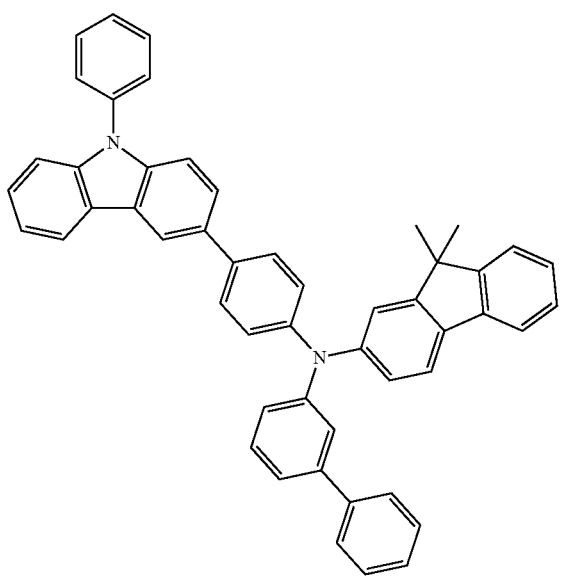
310
311

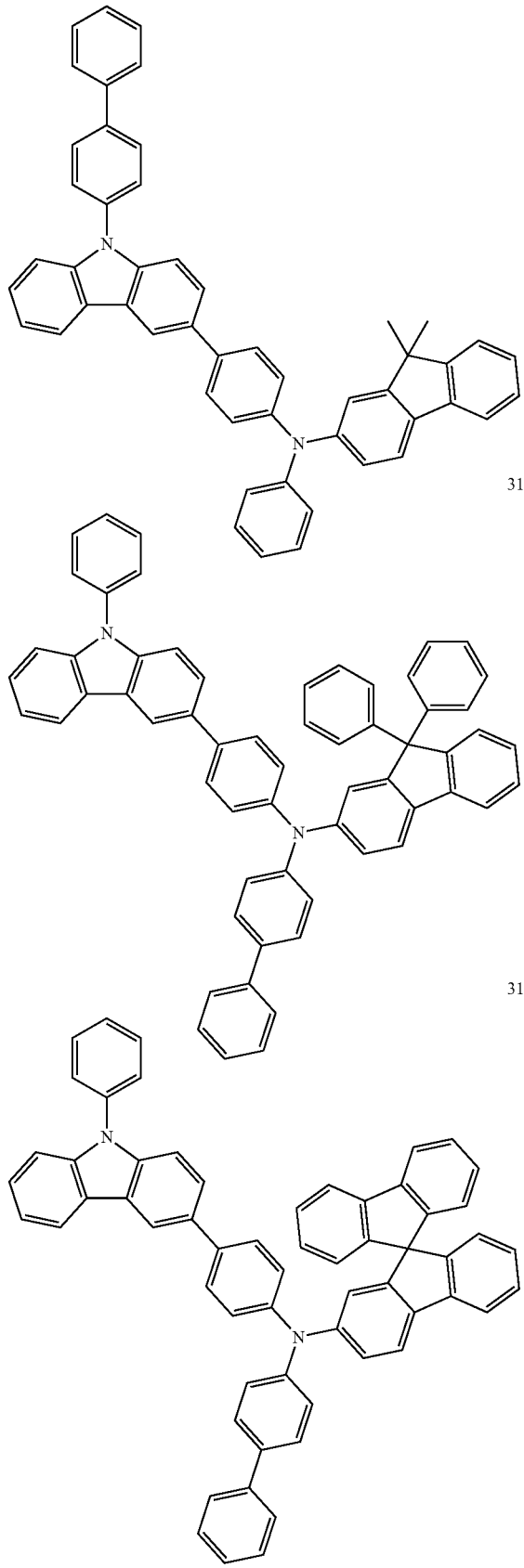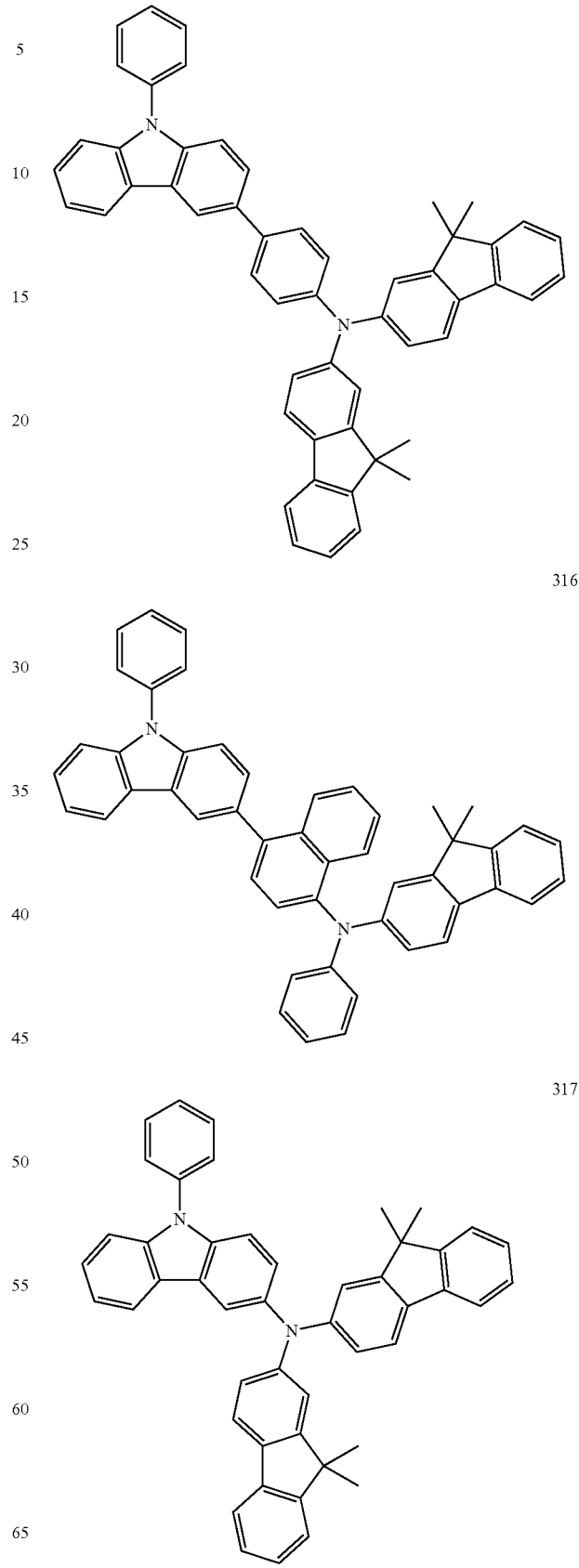

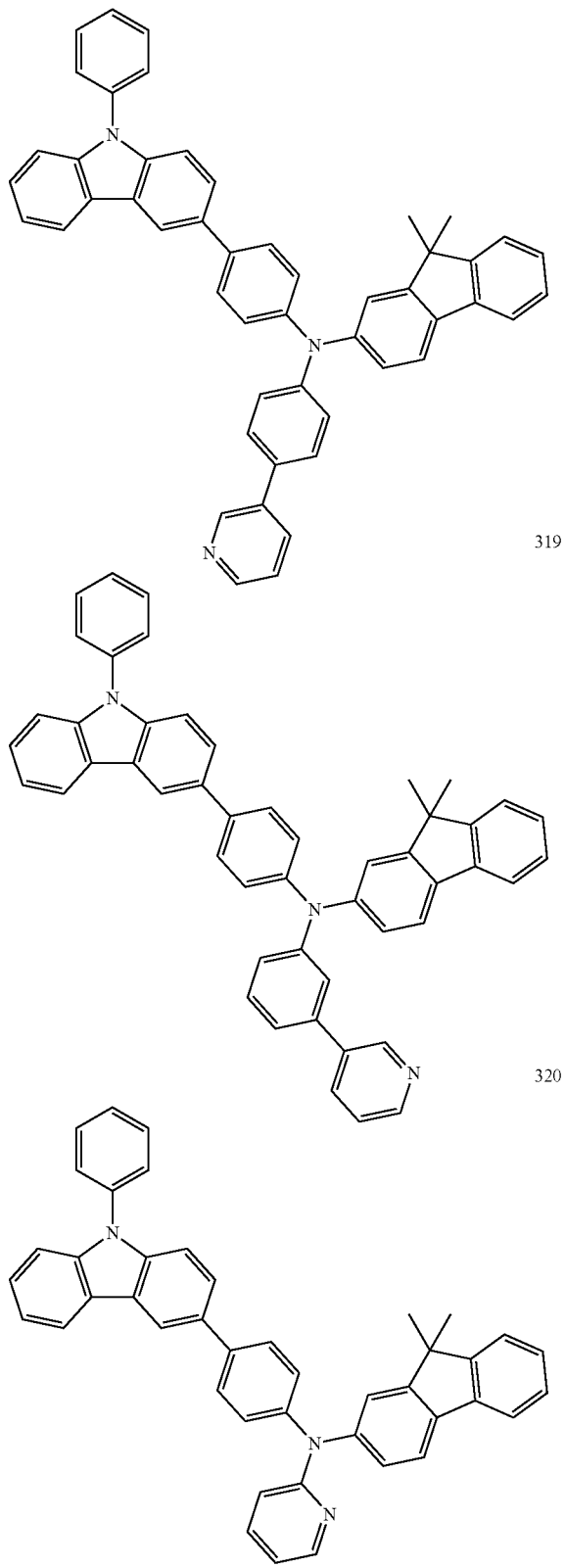

At least one of the HIL, the HTL, or the H-functional layer may further include a charge-generating material so as to increase the conductivity of the layers, in addition to the hole injection material, the hole transporting material and/or the material having hole injection and hole transport abilities.

The charge-generating material may be, for example, a p-dopant. The p-dopant may be selected from quinone derivatives, metal oxides, or cyano-containing compounds, but is not limited thereto. Non-limiting examples of the p-dopant may include quinone derivatives such as tetra-cyanoquinodimethane (TCNQ) and 2,3,5,6-tetrafluoro-tetracyano-1,4-benzoquinodimethane (F4-CTNQ); metal oxides such as tungsten oxides and molybdenum oxides; and cyano-containing compounds such as Compound 200 below and the like.

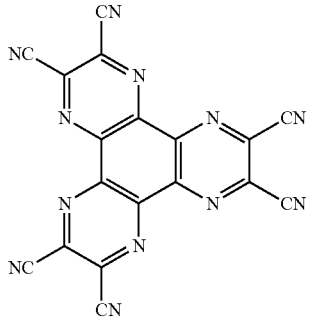

Compound 200

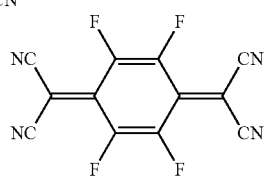

F4-CTNQ

When the HIL, the HTL or the H-functional layer further includes the charge-generating material, the charge-generating material may be homogeneously or inhomogeneously dispersed in these layers.

The buffer layer may be positioned between the EML and at least one of the HIL, the HTL, or the H-functional layer. The buffer layer may increase efficiency by compensating for an optical resonance distance according to the wavelength of light emitted from the EML. The buffer layer may include a hole injection material and a hole transporting material. Also, the buffer layer may include the same material as one of the materials included in the HIL, the HTL, or the H-functional layer, which are formed below the buffer layer.

Next, the EML may be formed on the HTL, the H-functional layer, or the buffer layer by vacuum deposition, spin coating, casting, or LB deposition. When the EML is formed by vacuum deposition or spin coating, the deposition or coating conditions may vary according to the compounds used. However, in general, the conditions may be similar or identical to the conditions for forming the HIL.

The EML may include a host. Examples of the host include, but are not limited to, Alq$_3$, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di(naphth-2-yl)anthracene (TBADN), E3, distyrylarylene (DSA), dmCBP (see the following formula), and Compounds 501 through 509 below.

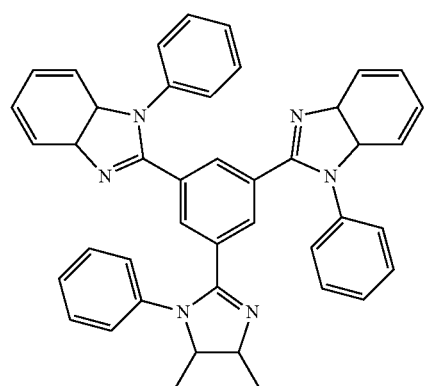
TPBI
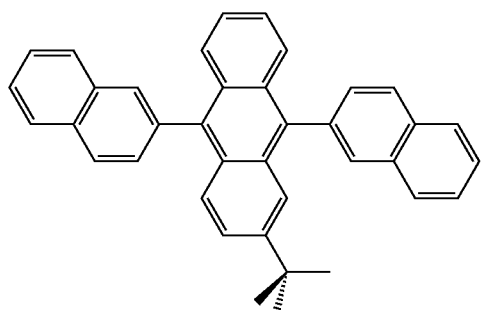
TBADN
E3
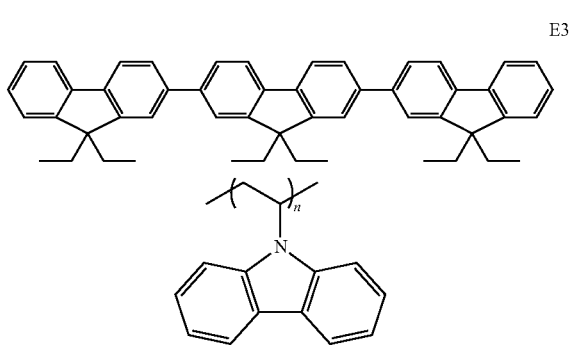
PVK
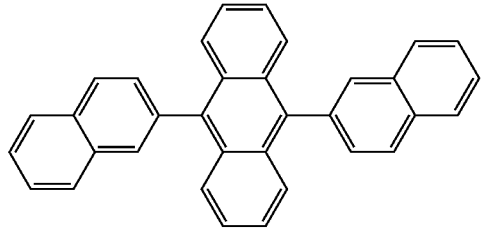
ADN
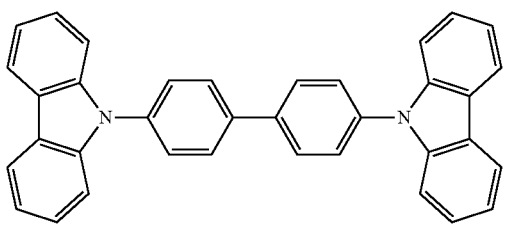
CBP
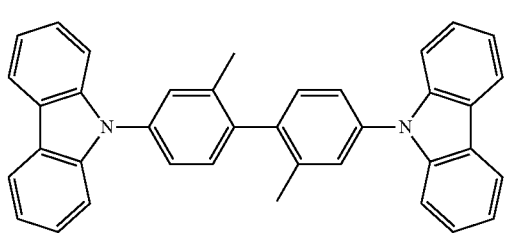
dmCBP
501
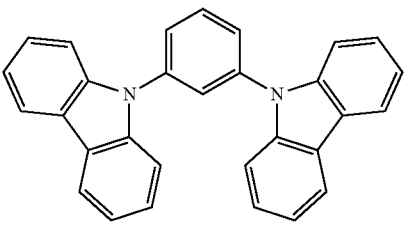
502
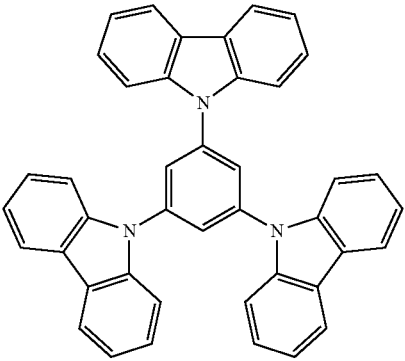
503
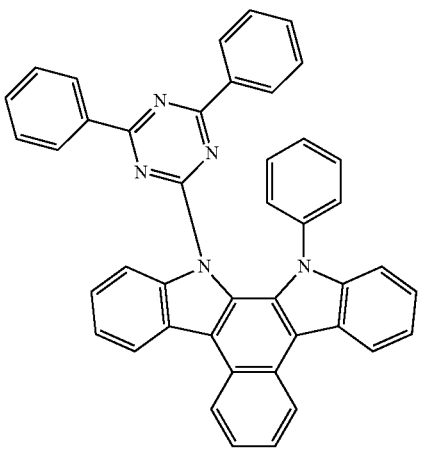

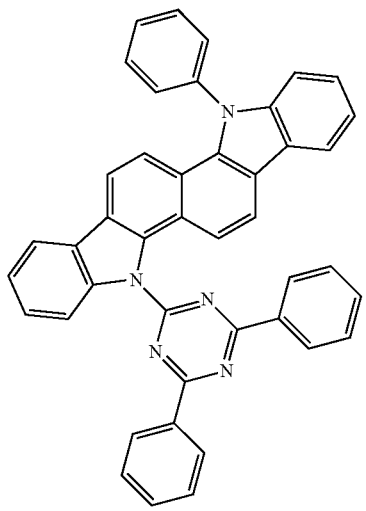
504

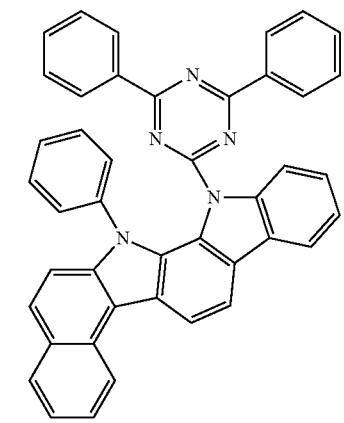
505

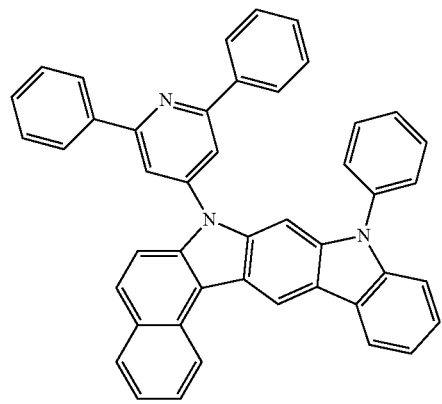
506

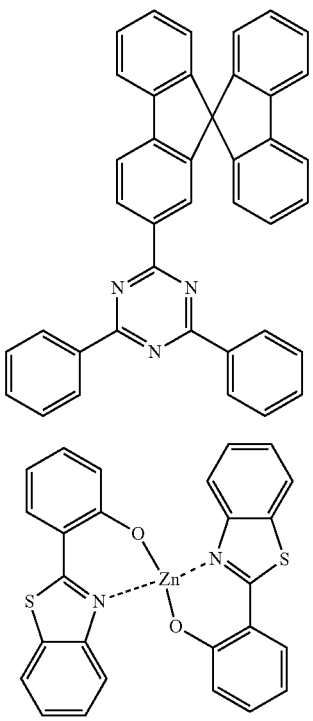
507

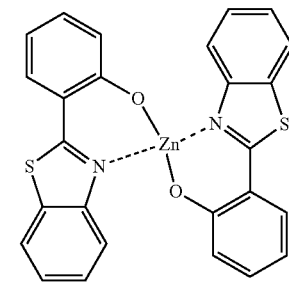
508

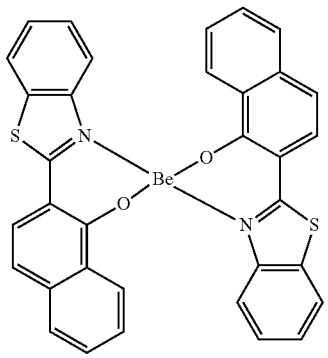
509

Also, the host may be an anthracene-based compound represented by Formula 400 below:

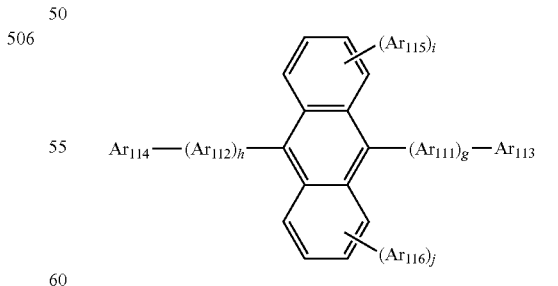

Formula 400

In Formula 400, $Ar_{111}$ and $Ar_{112}$ are each independently a substituted or unsubstituted $C_6$-$C_{60}$ arylene group. $Ar_{113}$ through $Ar_{116}$ are each independently a substituted or unsubstituted $C_1$-$C_{10}$ alkyl group or a substituted or unsubstituted $C_6$-$C_{60}$ aryl group. Each of g, h, I, and j may be independently an integer of 0 to 4.

For example, in Formula 400, $Ar_{111}$ and $Ar_{112}$ may be each independently one of a phenylene group, a naphthylene group, a phenanthrenylene group, a pyrenylene group; or a phenylene group, a naphthylene group, a phenanthrenylene group, a fluorenyl group, or a pyrenylene group substituted with at least one of a phenyl group, a naphthyl group, or an anthryl group, but $Ar_{111}$ and $Ar_{112}$ are not limited thereto.

In Formula 400, g, h, i, and j may be each independently 0, 1, or 2.

In Formula 400, $Ar_{113}$ through $Ar_{116}$ may be each independently one of a $C_1$-$C_{10}$ alkyl group substituted with at least one of a phenyl group, a naphthyl group, or an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group or a fluorenyl group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, or a fluorenyl group; or

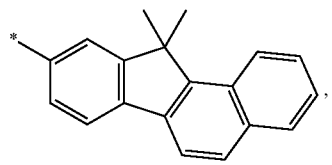 [SMILES: *c1ccc2c(c1)C(C)(C)c1c-2ccc2ccccc12]

but $Ar_{113}$ through $Ar_{116}$ are not limited thereto.

For example, the anthracene-based compound of Formula 400 may be one of the following compounds, but is not limited thereto:

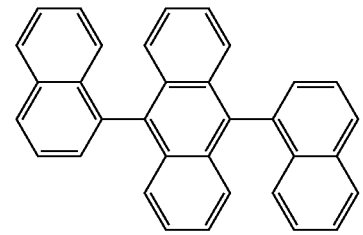

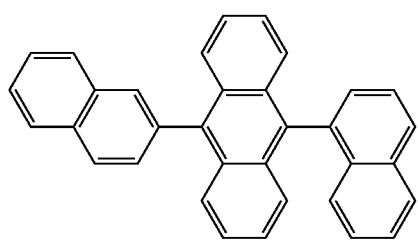

-continued

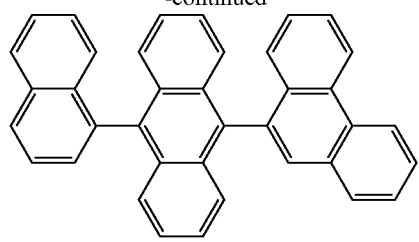

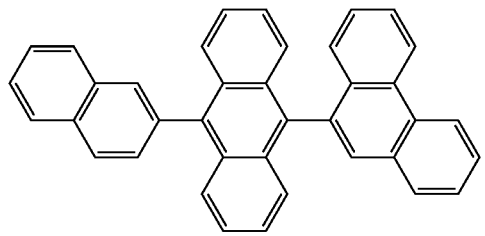

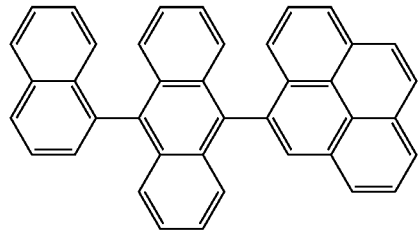

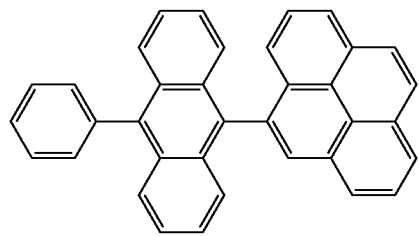

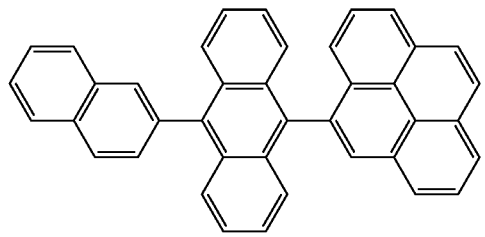

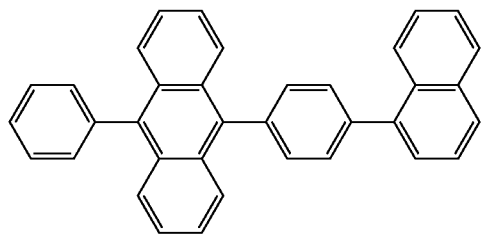

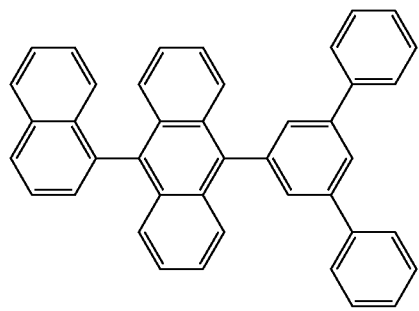

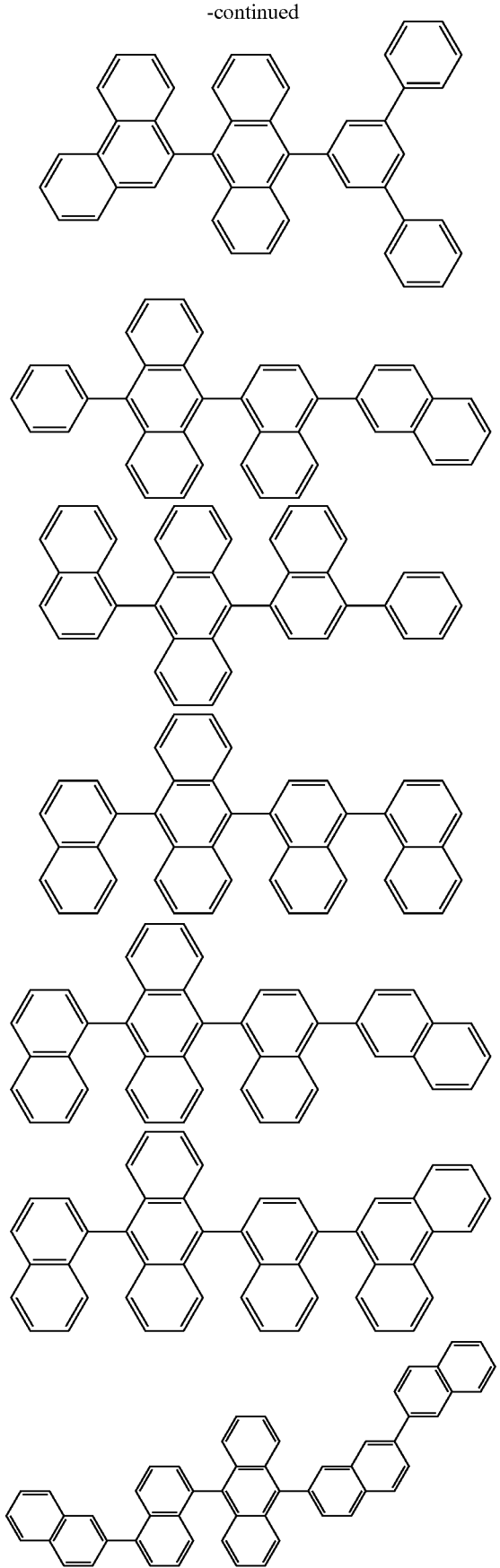

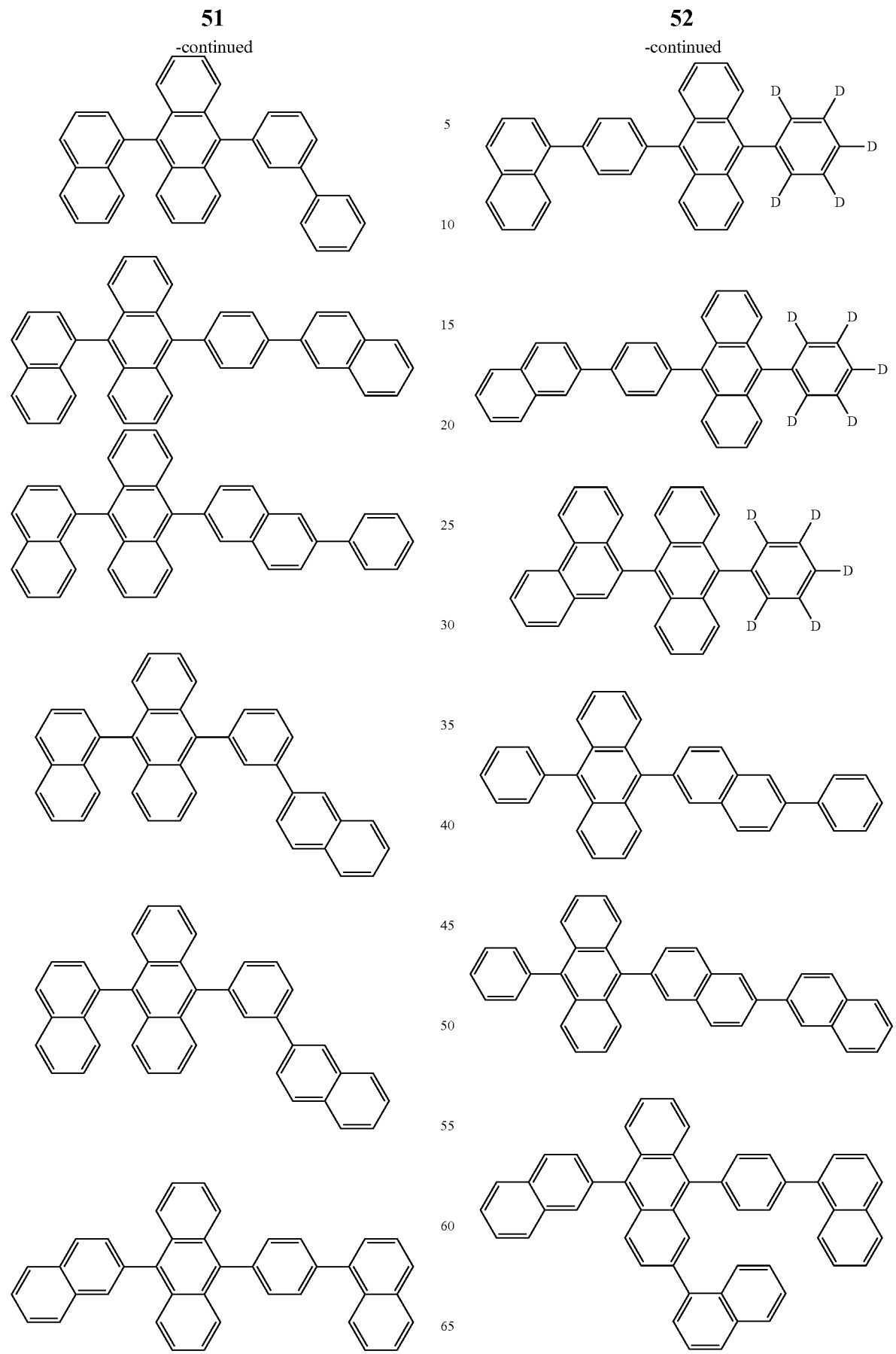

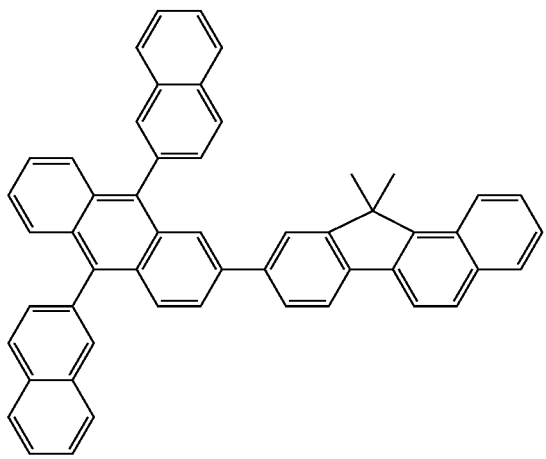

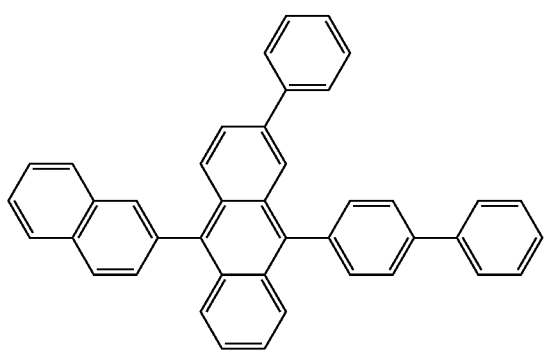

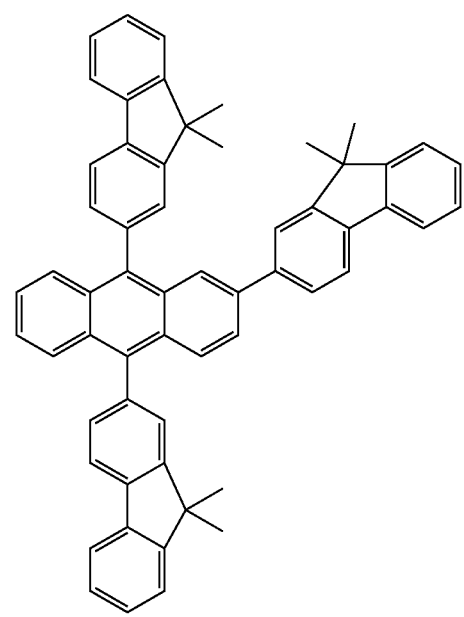

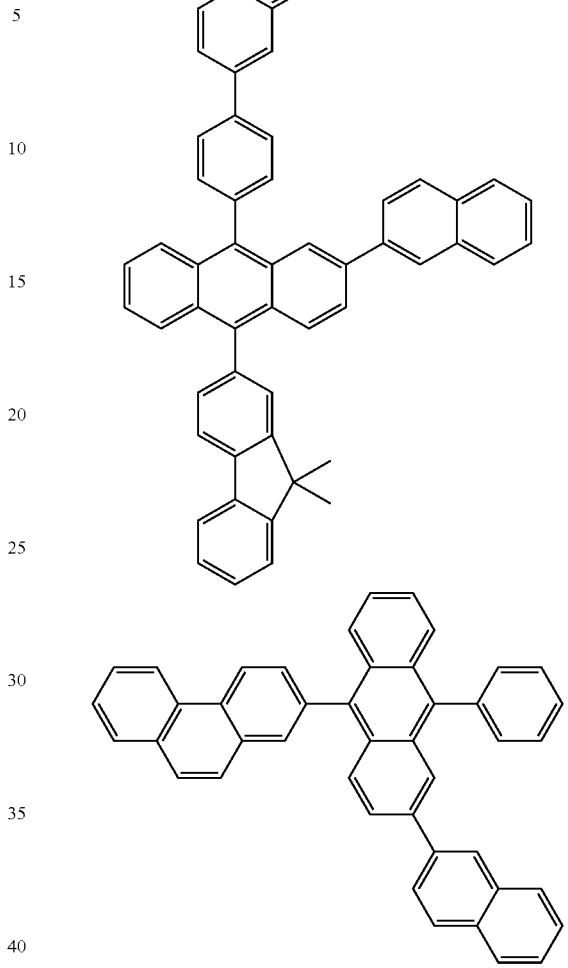

Also, the host may be an anthracene-based compound represented by Formula 401 below:

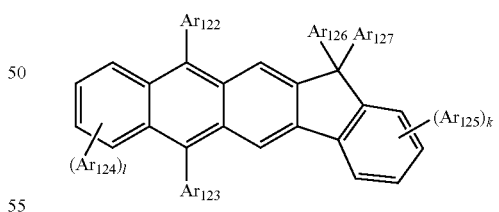

Formula 401

In Formula 401, $Ar_{122}$ through $Ar_{125}$ are the same as defined above with respect to $Ar_{113}$ of Formula 400.

In Formula 401, $Ar_{126}$ and $Ar_{127}$ may be each independently a $C_1$-$C_{10}$ alkyl group (for example, a methyl group, an ethyl group, or a propyl group).

In Formula 401, k and l may be each independently an integer of 0 to 4. For example, k and l may be each independently 0, 1, or 2.

For example, the anthracene-based compound of Formula 401 may be one of the following compounds, but is not limited thereto:

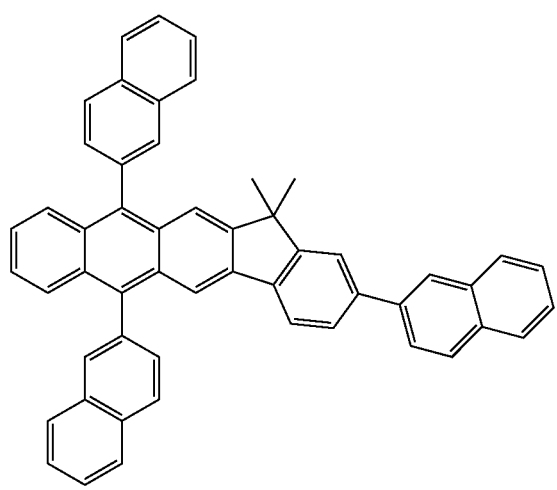
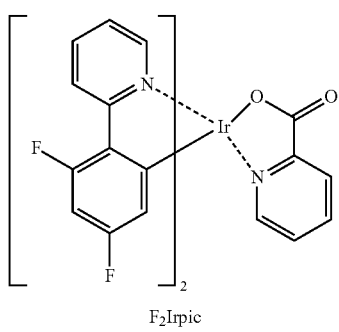
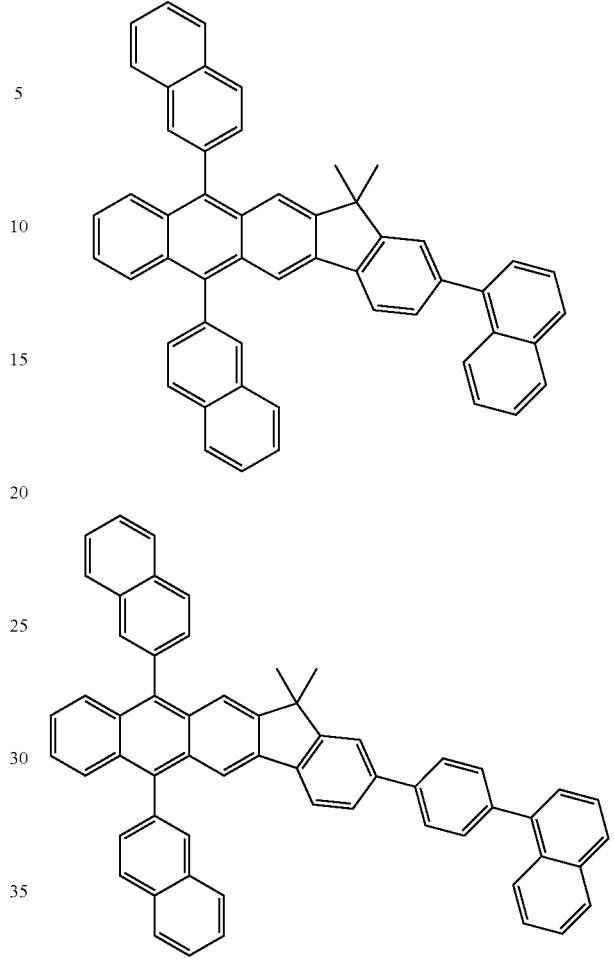
When the OLED is a full-color OLED, the EML may be patterned into a red EML, a green EML, and a blue EML.
At least one of the red EML, the green EML, and the blue EML may include one of the following dopants (ppy=phenylpyridine).
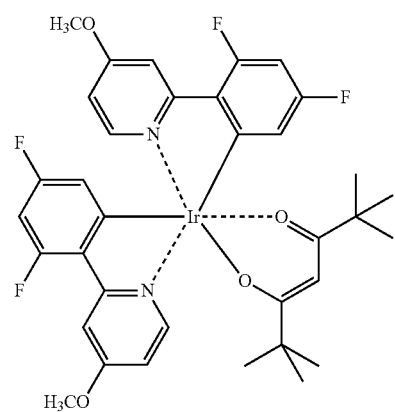
F₂Irpic        (F₂ppy)₂Ir(tmd)
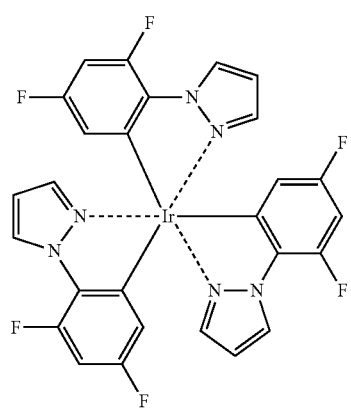
Ir(dfppz)₃

-continued
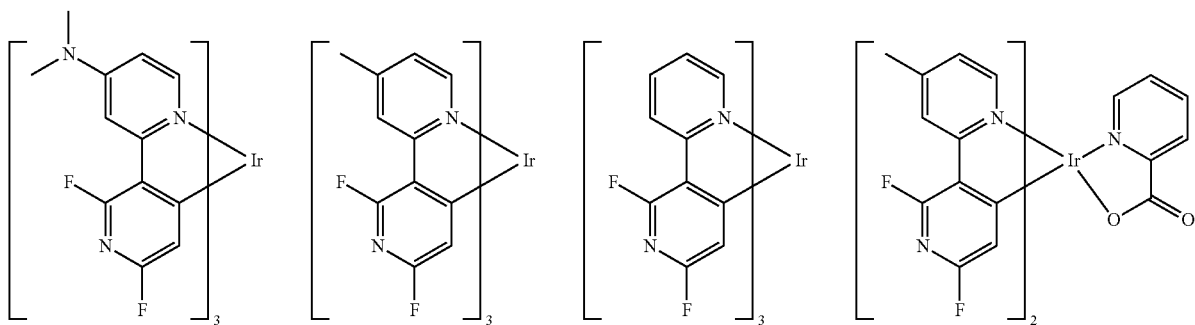
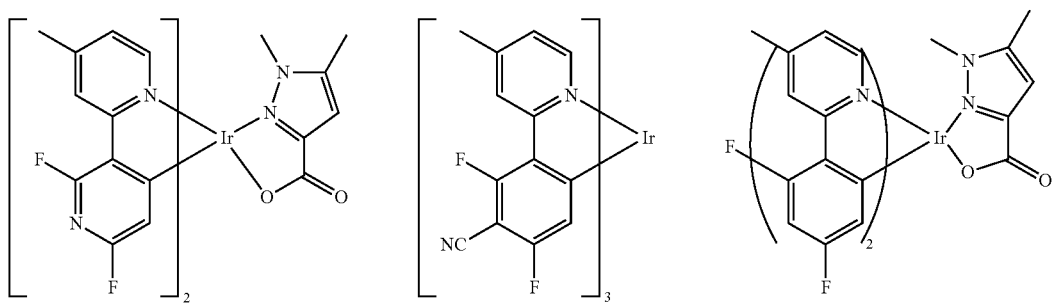
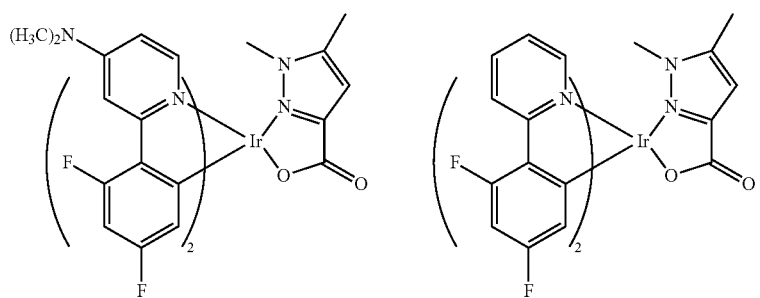
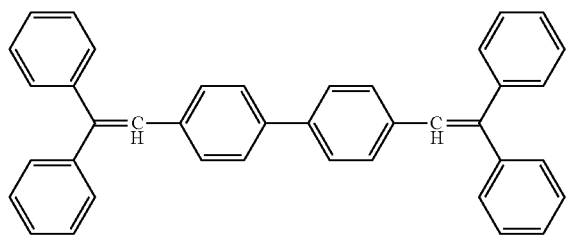
DPVBi
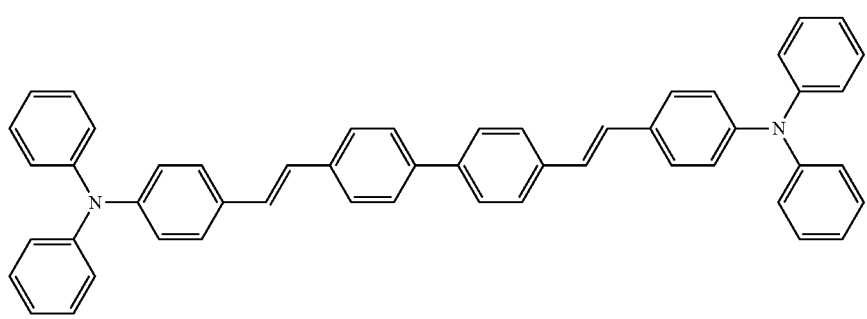
DPAVBi

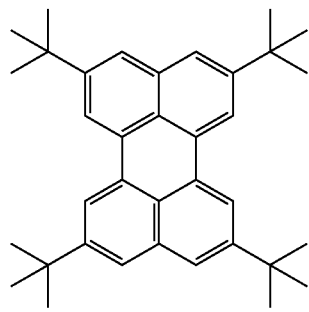
TBPe
Examples of a red dopant include, but are not limited to, the following compounds.
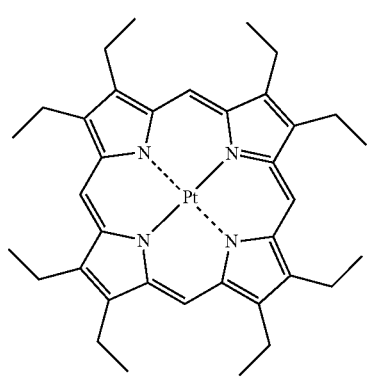
PtOEP
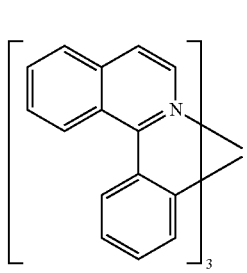
Ir(piq)₃
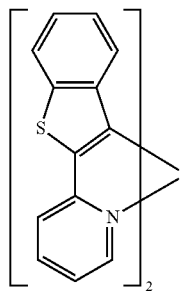
Btp₂Ir(acac)
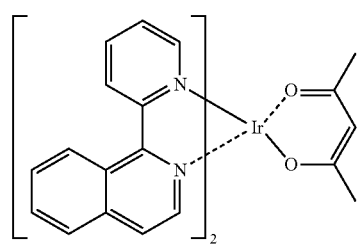
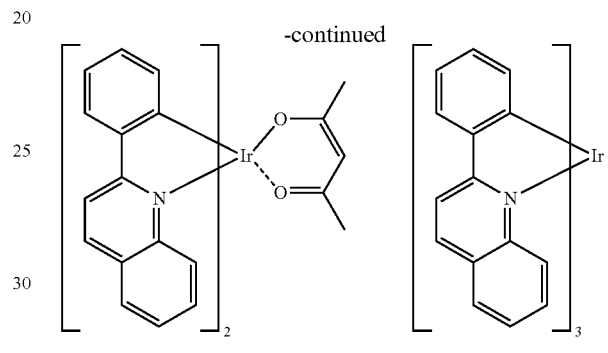
Ir(pq)₂(acac)    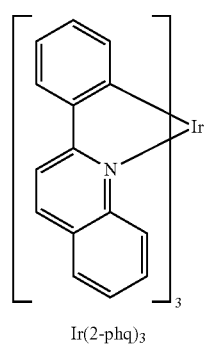 Ir(2-phq)₃
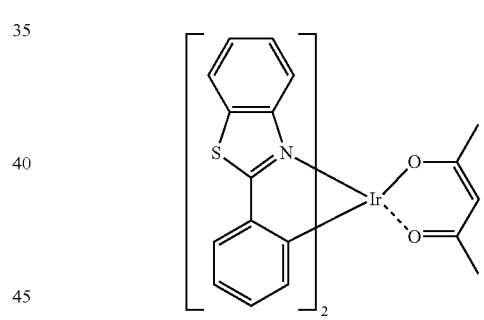
Ir(BT)₂(acac)
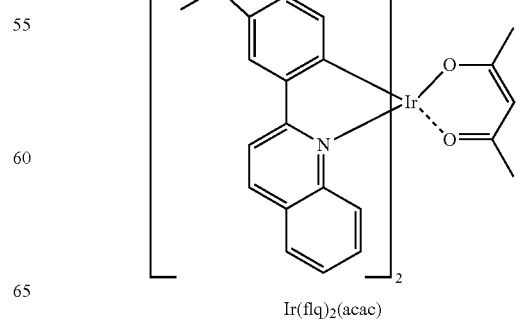
Ir(flq)₂(acac)

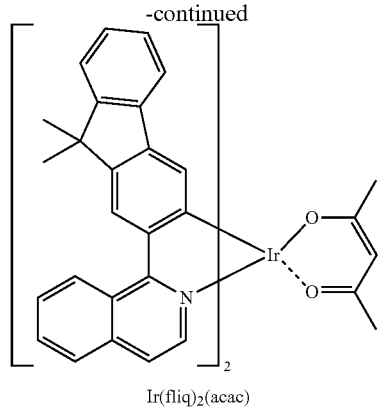
Ir(fliq)₂(acac)
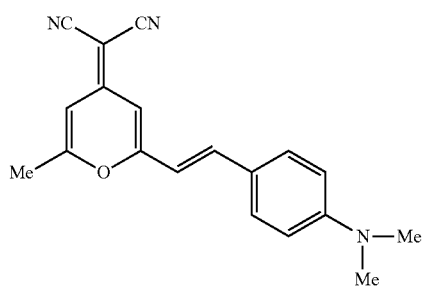
DCM
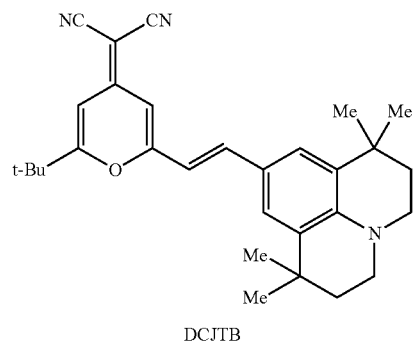 [SMILES: CC(C)(C)C1=CC(=C(C#N)C#N)C=C(/C=C/c2cc3c4c(c2)C(C)(C)CCN4CCC3(C)C)O1]
DCJTB
Examples of a green dopant include, but are not limited to, the following compounds.
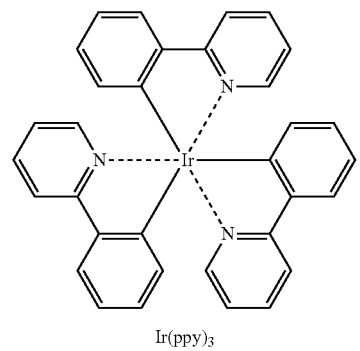
Ir(ppy)₃
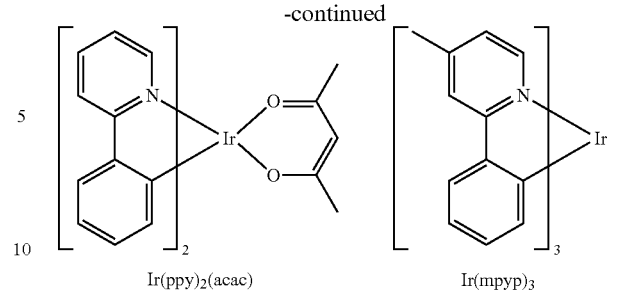
Ir(ppy)₂(acac)    Ir(mpyp)₃
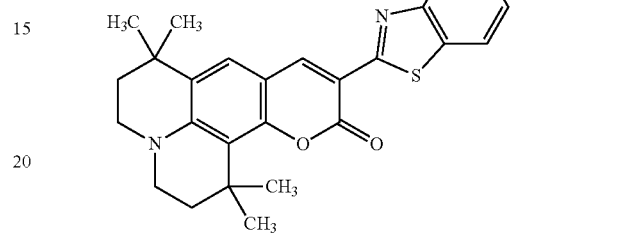
C545T
The dopant that may be included in the EML may be a Pt-complex as described below, but is not limited thereto:
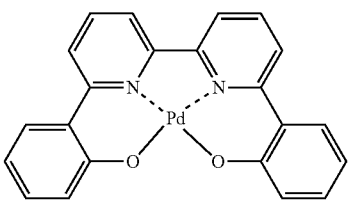
D1
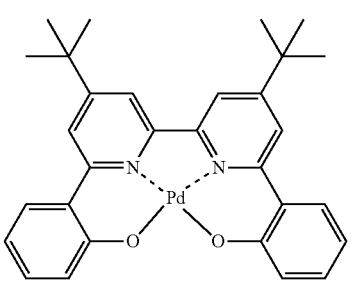
D2
D3

D4 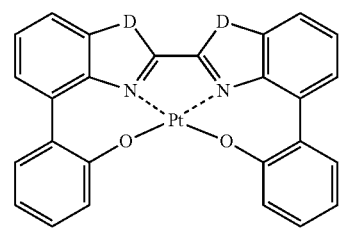
D5 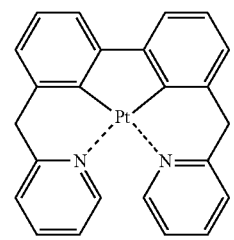
D6 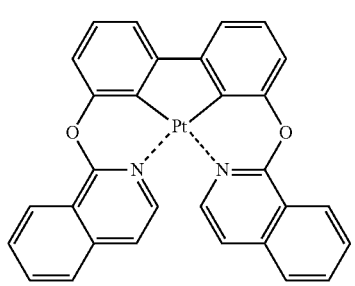
D7 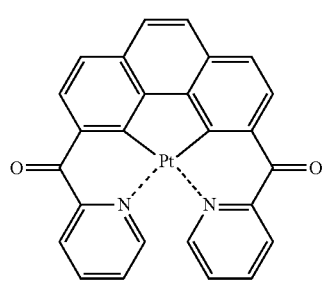
D8 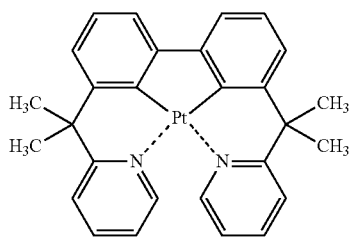
D9 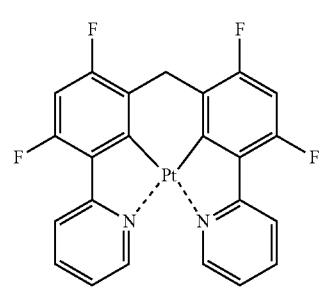
D10 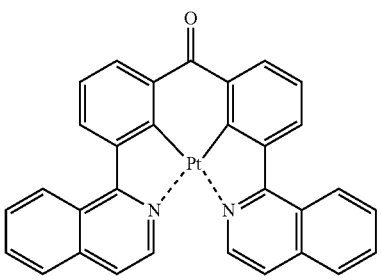
D11 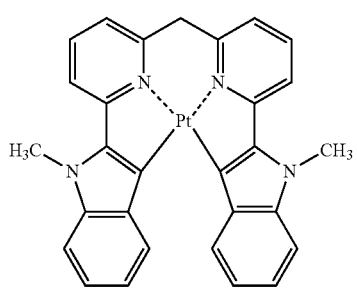
D12 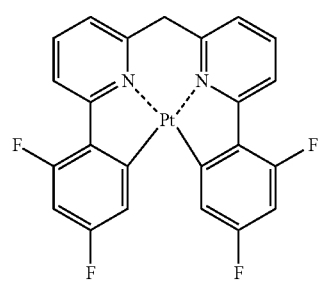
D13 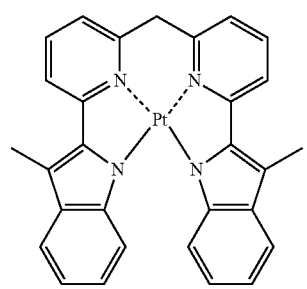
D14 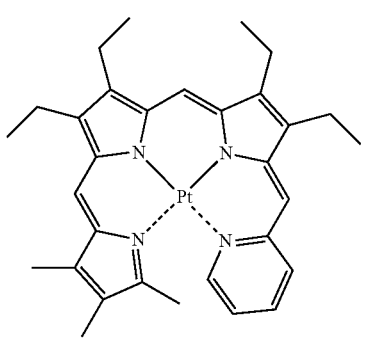

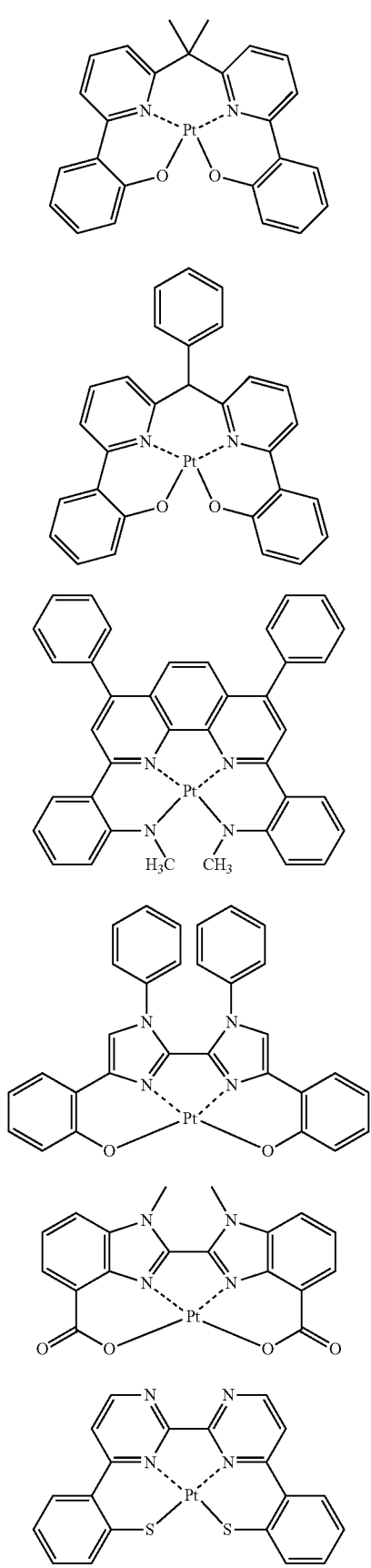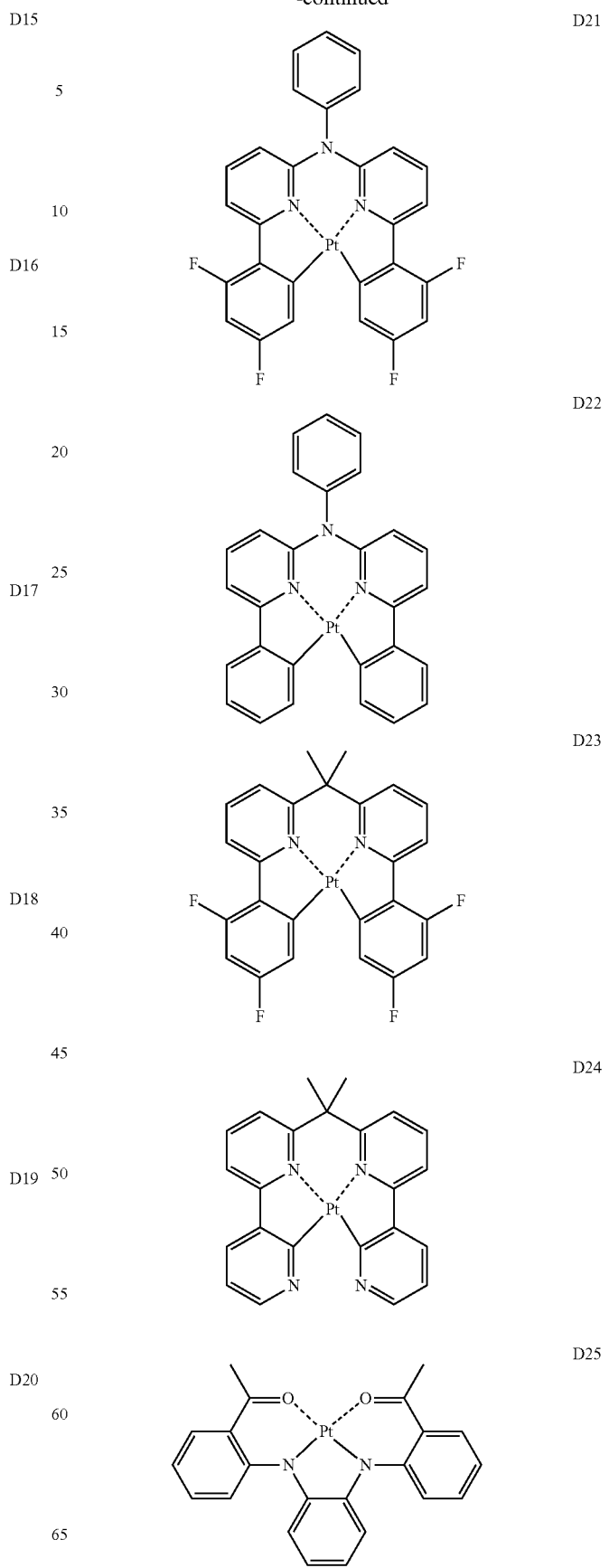

-continued
D26
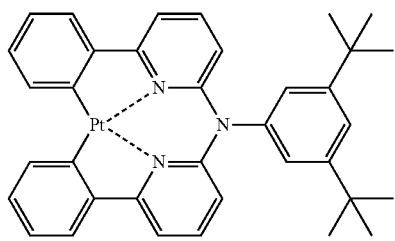
D27
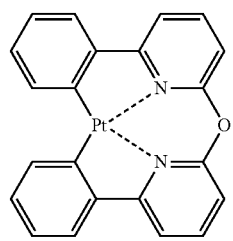
D28
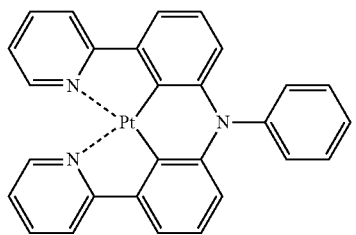
D29
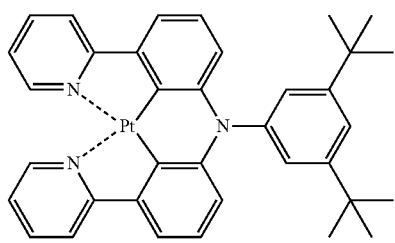
D30
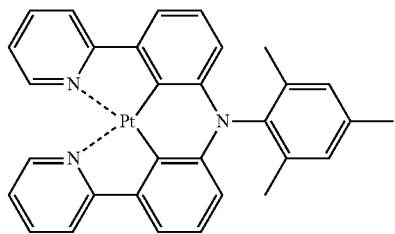
D31
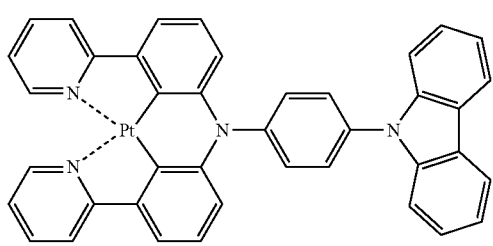
-continued
D32
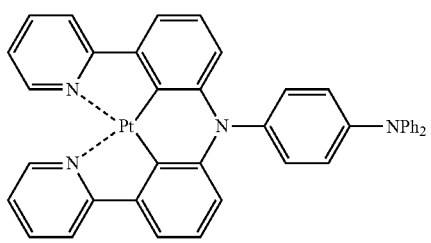
D33
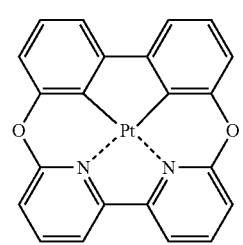
D34
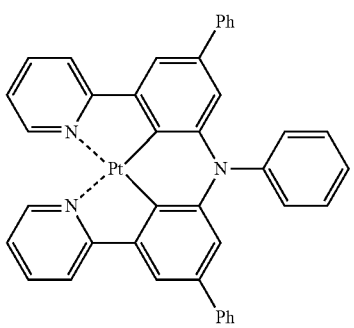
D35
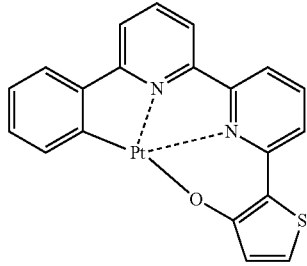
D36
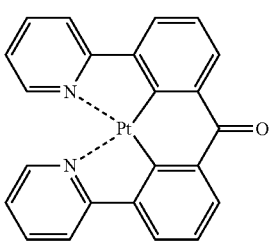

-continued
D37
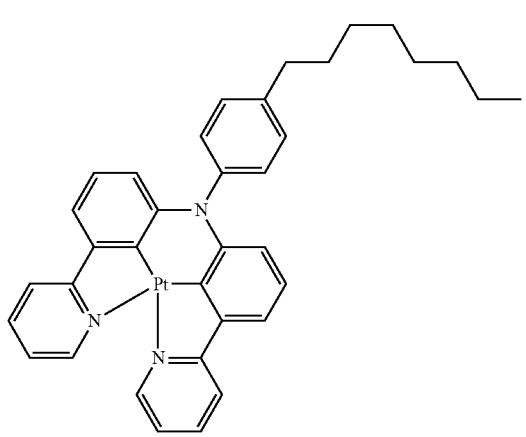
D38
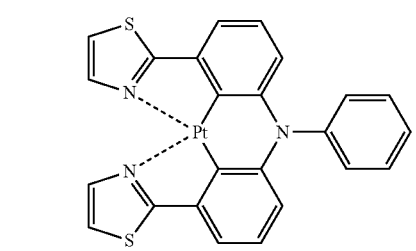
D39
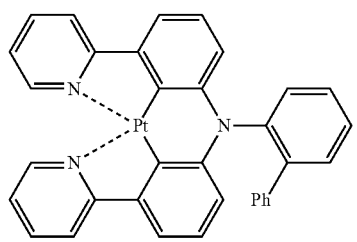
D40
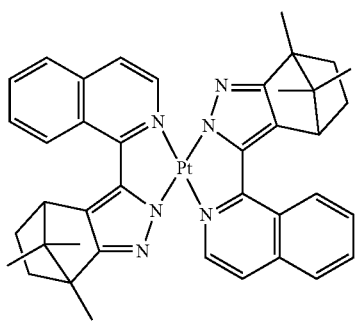
D41
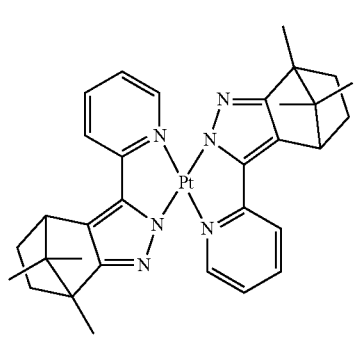
-continued
D42
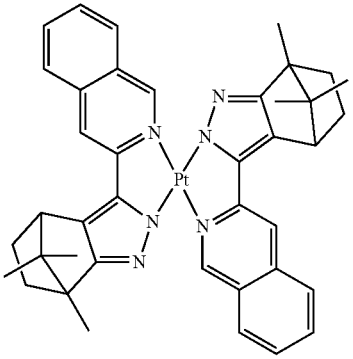
D43
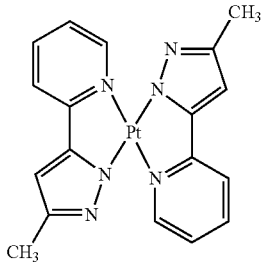
D44
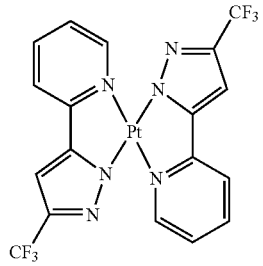
D45
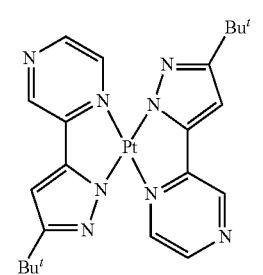
D46
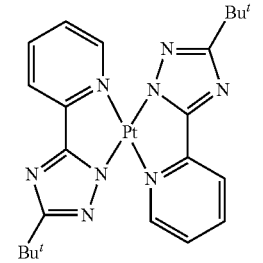

-continued

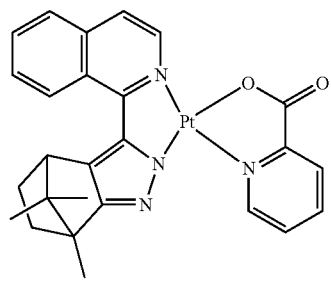
D47

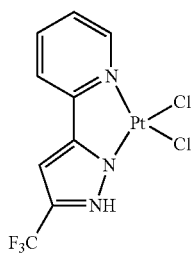
D48

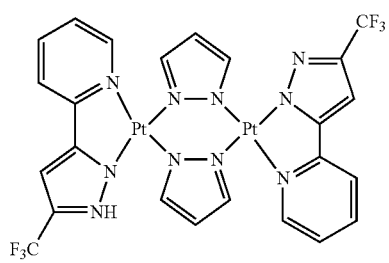
D49

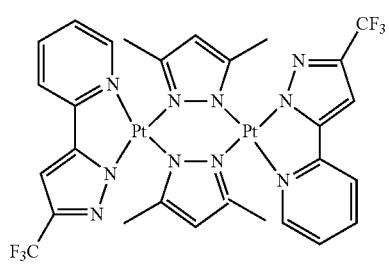
D50

Also, the dopant included in the EML may be an Os-complex such as those depicted below, but is not limited thereto:

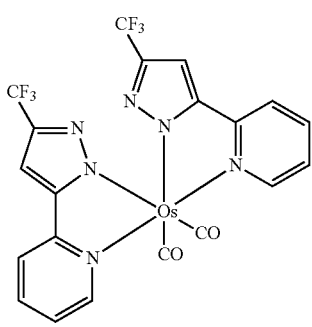

Os(fppz)$_2$(CO)$_2$

-continued

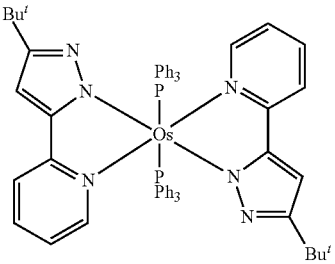

Os(fppz)$_2$(PPh$_2$Me)$_2$

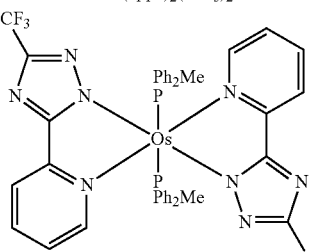

Os(bppz)$_2$(PPh$_3$)$_2$

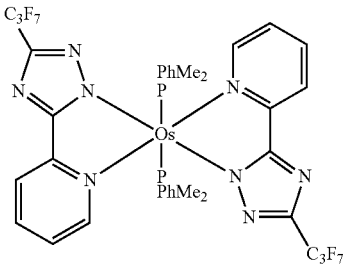

Os(fptz)$_2$(PPh$_2$Me)$_2$

Os(hptz)$_2$(PPh$_2$Me$_2$)$_2$

When the EML includes a host and a dopant, the amount of the dopant may be generally about 0.01 to about 15 parts by weight based on 100 parts by weight of the host, but is not limited thereto.

The thickness of the EML may be about 100 Å to about 1,000 Å. In some embodiment, the thickness of the EML may be about 200 Å to about 600 Å. When the thickness of the ETL is within these ranges, good luminescent properties may be obtained without a substantial increase in driving voltage.

Next, the ETL is formed on the EML by various methods, such as vacuum deposition, spin coating, or casting. When the ETL is formed by vacuum deposition or spin coating, the deposition or coating conditions may vary according to the compounds used. However, in general, the deposition and coating conditions may be similar or identical to the conditions for forming the HIL. The material for forming the ETL may be any electron transporting material that stably transports electrons injected from a cathode. Examples of the electron transporting materials may include, but are not limited to, a quinoline derivative such as tris(8-quinolinolate) aluminum (Alq$_3$), TAZ, Balq, beryllium bis(benzoquinolin-10-olate) (Bebq$_2$), ADN, Compound 201 below, and Compound 202 below.

Compound 201

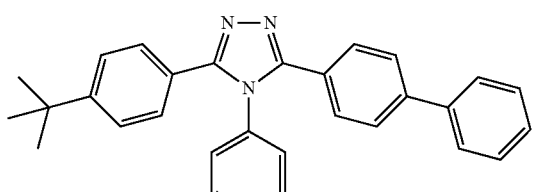

TAZ

Compound 202

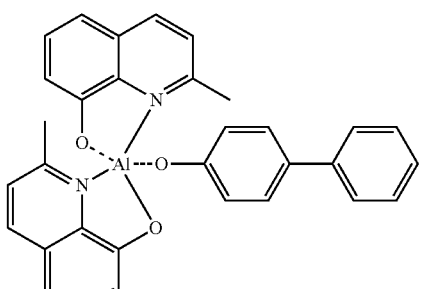

BAlq

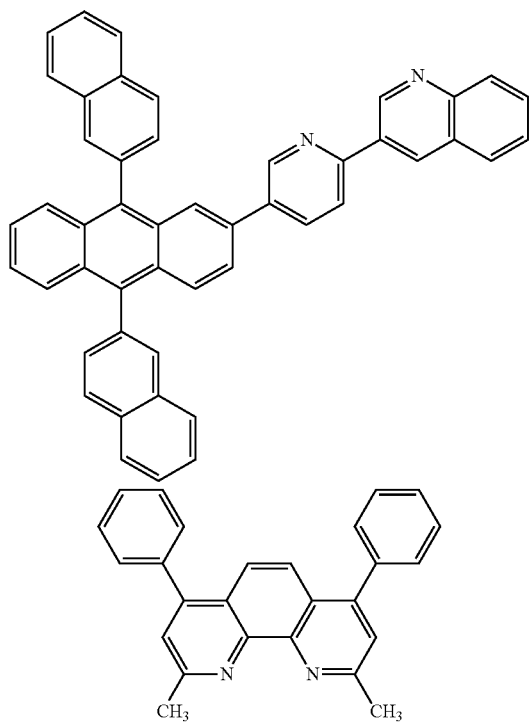

BCP

The thickness of the ETL may be about 100 Å to about 1,000 Å. In some embodiments, the thickness of the ETL may be about 150 Å to about 500 Å. When the thickness of the ETL is within these ranges, satisfactory electron transport properties may be obtained without a substantial increase in driving voltage.

The ETL may further include a known electron transporting organic compound and a metal-containing material.

The metal-containing material may include a Li-complex. Examples of the Li-complex may include, but are not limited to, lithium quinolate (LiQ) and Compound 203 below.

Compound 203

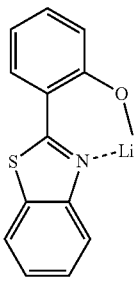

Also, the EIL, which facilitates electron injection from a cathode, may be formed on the ETL, and the material for forming the EIL is not particularly limited.

The material for forming the EIL may include a known material for forming an EIL, such as LiF, NaCl, CsF, Li$_2$O, or BaO. The deposition conditions of the EIL may vary according to the compound used. However, in general, the conditions may be similar or identical to the conditions for forming the HIL.

The thickness of the EIL may be about 1 Å to about 100 Å. In some embodiments, the thickness of the EIL may be about 3 Å to about 90 Å. When the thickness of the EIL is within these ranges, satisfactory electron injection properties may be obtained without a substantial increase in driving voltage.

The second electrode is formed on these organic layers. The second electrode may be a cathode, which is an electron injection electrode. In this regard, a metal for forming the second electrode may include a metal having a low work function, such as a metal, an alloy, an electrically conducting compound, or a mixture thereof. In particular, the second electrode may be formed as a thin film of lithium (Li), magnesium (Mg), aluminum (Al), aluminum-lithium (Al—Li), calcium (Ca), magnesium-indium (Mg—In), or magnesium-silver (Mg—Ag), thus being transparent. In order to obtain a top-emission type OLED, the second electrode may be formed as a transparent electrode using ITO or IZO.

The OLED has been described with reference to FIG. 1, but is not limited thereto.

In addition, when the EML includes a phosphorescent dopant, a HBL may be formed between the HTL and the EML or between the H-functional layer and the EML using various methods such as vacuum deposition, spin coating, casting, or LB deposition. The HBL functions to prevent triplet excitons or holes from diffusing into the ETL. When the HBL is formed by vacuum deposition or spin coating, the deposition or coating conditions may vary according to the compound used. However, in general, the deposition or coating conditions may be similar or identical to the conditions for forming the HIL. A material for forming the HBL may be a known hole blocking material, such as an oxadiazole derivative, a triazole derivative, or a phenanthroline derivative. For example, the material for forming the HBL may be BCP below.

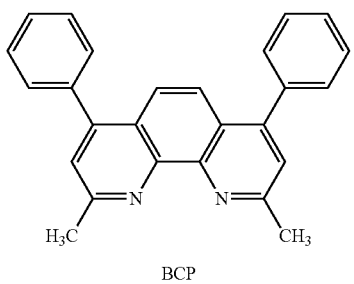

BCP

The thickness of the HBL may be about 20 Å to about 1,000 Å, for example, about 30 Å to about 300 Å. When the thickness of the HBL is within these ranges, satisfactory hole blocking properties may be obtained without a substantial increase in driving voltage.

The OLED may be used in various types of flat panel display devices, for example, passive matrix OLEDs and active matrix OLEDs. In particular, in an active matrix OLED, a first electrode formed on the substrate side, which is a pixel electrode, may be electrically connected to a source electrode or a drain electrode of a thin film transistor. Also, the OLED may be used in a dual-screen flat panel display device.

According to an embodiment of the present invention, the organic layer of the OLED may be formed using a compound of Formula 1 by deposition, or, according to another embodiment of the present invention, using a compound of Formula prepared in a liquid state using a wet process.

OLEDs according to embodiments of the present invention will now be described with reference to the following Synthesis Examples and Examples. These Examples are presented for illustrative purposes only and are not intended to limit the scope of the invention.

EXAMPLES

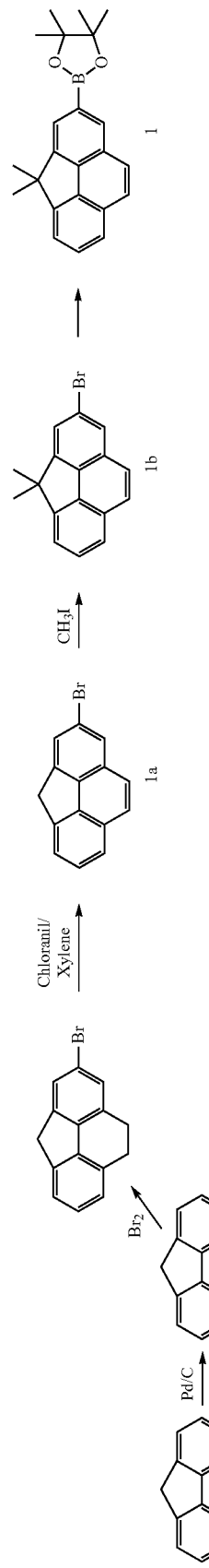
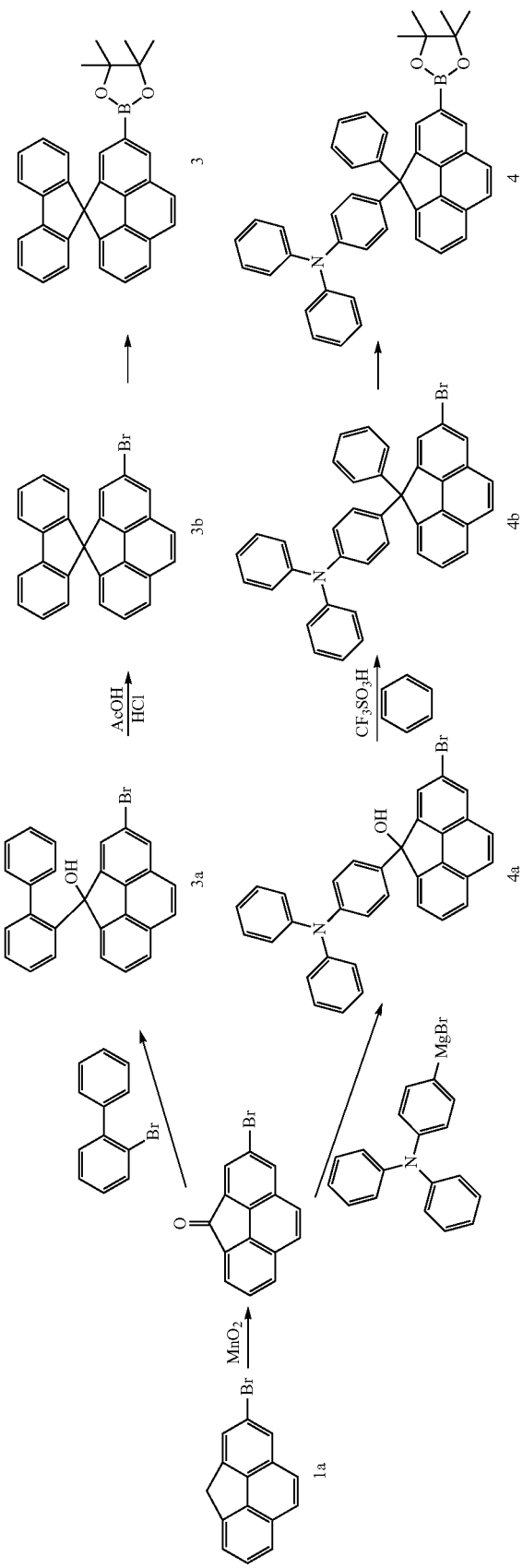

Synthesis of Intermediate 1

1) Synthesis of 8,9-dihydro-4H-cyclopenta[def]phenanthrene 10.0 g (52.6 mmol) of 4H-cyclopenta[def]phenanthrene and 8.40 g of 5% Pd/C were dissolved in 70 ml of EtOH in a Par reactor bottle, and the resultant solution was stirred at room temperature for 24 hours with hydrogen pressure being maintained at 40 psi. After the reaction was completed, the reaction solution was filtered and the solvent was evaporated therefrom to obtain 8.60 g of white target material (yield: 85.0%). The obtained compound was confirmed by liquid chromatography-mass spectrometry (LC-MS).

$C_{15}H_{12}$: calc. 192.09, found [M+1] 193.1.

2) Synthesis of 2-bromo-8,9-dihydro-4H-cyclopenta[def]phenanthrene 8.5 g (44.2 mmol) of 8,9-dihydro-4H-cyclopenta[def]phenanthrene was dissolved in 80 ml of $CCl_4$, and 7.1 g (44.2 mmol) of $Br_2$ was then slowly added thereto at 0° C. The reaction solution was stirred at room temperature for 4 hours and a 10% $Na_2SO_3$ solution was added thereto to separate the organic layer. The obtained organic layer was dried with magnesium sulfate, the solvent was evaporated therefrom, and the resultant product was recrystallized with n-hexane. As a result, 9.6 g of the target material was obtained (yield: 80%). The obtained compound was confirmed by LC-MS.

$C_{15}H_{11}Br$: calc. 270.00, found [M+1] 271.00.

3) Synthesis of Intermediate 1a 9.3 g (34.3 mmol) of 2-bromo-8,9-dihydro-4H-cyclopenta[def]phenanthrene and 8.8 g (36.0 mmol) of o-chloranil were dissolved in 70 ml of xylene, and the mixture was stirred at 110° C. for 72 hours. Thereafter, the reaction solution was cooled to room temperature, and the solvent was evaporated therefrom to obtain a residue. The residue was purified with silicagel column chromatography to obtain 7.48 g of Intermediate 1a (yield: 81%). The obtained compound was confirmed by LC-MS.

$C_{15}H_9Br$: calc. 267.99, found [M+1] 268.97.

4) Synthesis of Intermediate 1b 7.3 g (27.1 mmol) of Intermediate 1a, 73.2 g (216.8 mmol) of t-BuOK, and 60 ml of HMPA were dissolved in 60 ml of DMSO, and the resultant product was stirred at room temperature for 1 hour. Subsequently, 30.6 g (216.8 mmol) of $CH_3I$ was slowly added to the reaction solution at 0° C., the resultant was stirred for 30 minutes, 40 ml of water was added thereto, and the resulting product was extracted three times with 70 ml of methylene chloride. The obtained organic layer was dried with magnesium sulfate, and the solvent was evaporated therefrom to obtain a residue. The residue was purified with silicagel column chromatography to obtain 6.3 g of Intermediate 1b (yield: 78%). The obtained compound was confirmed by LC-MS.

$C_{17}H_{13}Br$: calc. 296.02, found [M+1] 297.05.

5) Synthesis of Intermediate 1

2.97 g (10.0 mmol) of Intermediate 1b, 2.54 g (10.0 mmol) of bis(pinacolato)diborone, 0.36 g (0.5 mmol) of [1,1-bis(diphenylphosphino)ferrocene]dichloro palladium (II) ($PdCl_2(dppf_2)$), and 2.94 g (30.0 mmol) of KOAc were dissolved in 40 ml of DMSO, and the resultant solution was stirred at 80° C. for 6 hours. Subsequently, the reaction solution was cooled down to room temperature and extracted three times with 50 ml of water and 50 ml of diethylether. The obtained organic layer was dried with magnesium sulfate, and a solvent was evaporated therefrom to obtain a residue. The residue was purified with silicagel column chromatography to obtain 3.06 g of Intermediate 1 (yield: 89%). The obtained compound was confirmed by LC-MS.

$C_{23}H_{25}BO_2$: calc. 344.19, found [M+1] 345.20.

Synthesis of Intermediate 2

1) Synthesis of 2,6-dibromo-8,9-dihydro-4H-cyclopenta[def]phenanthrene 8.9 g of a target material was obtained (yield: 57%) in the same manner as step 2) of the synthesis of Intermediate 1, except that the amount of $Br_2$ used was 14.2 g (88.4 mmol). The obtained compound was confirmed by LC-MS.

$C_{15}H_{10}Br_2$: calc. 347.91, found [M+1] 348.90.

2) Synthesis of Intermediate 2a 6.8 g of Intermediate 2a was obtained (yield: 80%) in the same manner as in step 3) of the synthesis of Intermediate 1, except that 2,6-dibromo-8,9-dihydro-4H-cyclopenta[def]phenanthrene was used instead of 2-bromo-8,9-dihydro-4H-cyclopenta[def]phenanthrene. The obtained compound was confirmed by LC-MS.

$C_{15}H_8Br_2$: calc. 345.90, found [M+1] 346.90.

3) Synthesis of Intermediate 2b 5.8 g of Intermediate 2b was obtained (yield: 79%) in the same manner as in step 4) of the synthesis of Intermediate 1, except that Intermediate 2a was used instead of Intermediate 1a. The obtained compound was confirmed by LC-MS.

$C_{17}H_{12}Br_2$: calc. 373.93, found [M+1] 374.93.

4) Synthesis of Intermediate 2

2.91 g of Intermediate 2 was obtained (yield: 62%) in the same manner as in step 5) of the synthesis of Intermediate 1, except that Intermediate 2b was used instead of Intermediate 1b and the amount of bis(pinacolato)diborone used was 5.08 g (20.0 mmol). The obtained compound was confirmed by LC-MS.

$C_{29}H_{36}B_2NO_4$: calc. 470.28, found [M+1] 471.20.

Synthesis of Intermediate 3

1) Synthesis of 2-bromo-cyclopenta[def]phenanthren-4-one 7.4 g (27.5 mmol) of Intermediate 1a and 310 g of $MnO_2$ were dissolved in 200 ml of benzene, and the resultant solution was then stirred at 80° C. for 20 hours. The reaction solution was cooled down to room temperature and then filtered to remove $MnO_2$, and the filtrate was washed with 50 ml of $CHCl_3$, 50 ml of THF and 50 ml of MeOH, in that order. The resultant filtrate was evaporated to obtain a residue. The residue was recrystallized with acetone to obtain 3.74 g of 2-bromo-cyclopenta[def]phenanthren-4-one (yield: 48%). The obtained compound was confirmed by LC-MS.

$C_{15}H_7BrO$: calc. 281.97, found [M+1] 282.97.

2) Synthesis of Intermediate 3a 3.05 g (13.1 mmol) of 2-bromo biphenyl was dissolved in 50 ml of THF, and 15.4 ml (26.2 mmol) of t-BuLi (1.7M in Pentane) was then slowly added thereto at −78° C. The resultant solution was stirred for 1 hour at −78° C., 3.7 g (13.1 mmol) of 2-bromo-cyclopenta[def]phenanthrene-4-one was slowly added thereto for 30 minutes, and the resultant reaction solution was stirred at −78° C. for 30 minutes and then further stirred at room temperature for 3 hours. Then, 40 ml of water was added to the reaction solution and the resulting reaction solution was extracted three times with 50 ml of ethyl acetate. The obtained organic layer was dried with magnesium sulfate, and the solvent was evaporated therefrom to obtain a residue. The residue was purified with silicagel column chromatography to obtain 5.44 g of Intermediate 3a (yield: 95%). The obtained compound was confirmed by LC-MS.

$C_{27}H_{17}BrO$: calc. 436.05, found [M+1] 437.05.

3) Synthesis of Intermediate 3b 5.4 g (12.3 mmol) of Intermediate 3a was dissolved in 50 ml of acetic acid, 3 ml of concentrated hydrochloric acid was then slowly added thereto at 0° C., and the resultant solution was stirred for 2 hours. A white solid obtained during the reaction was filtrated and washed with acetic acid and ethanol to obtain 4.70 g of Intermediate 3b (yield: 90%). The obtained compound was confirmed by LC-MS.

$C_{27}H_{15}Br$: calc. 418.04, found [M+1] 418.05.

4) Synthesis of Intermediate 3

4.1 g of Intermediate 3 was obtained (yield: 88%) in the same manner as in step 5) of the synthesis of Intermediate 1, except that Intermediate 3b was used instead of Intermediate 1b. The obtained compound was confirmed by LC-MS.

$C_{33}H_{27}BO_2$: calc. 466.21, found [M+1]466.30.

Synthesis of Intermediate 4

1) Synthesis of Intermediate 4a 3.7 g (13.1 mmol) of 2-bromo-cyclopenta[def]phenanthrene-4-one was dissolved in 50 ml of ether and 20 ml of THF, 4.55 g (13.1 mmol) of (4-(diphenylamino)-phenyl)-magnesium bromide was then slowly added thereto, and the resultant solution was stirred at 80° C. for 3 hours. The reaction solution was cooled down to room temperature, 30 ml of water was added thereto, the pH of the reaction solution was adjusted to 3 to 4 using a 1N HCl solution, and the resultant reaction solution was extracted three times with 50 ml of ethyl acetate. The obtained organic layer was dried with magnesium sulfate, and the solvent was evaporated therefrom to obtain a residue. The residue was purified with silicagel column chromatography to obtain 4.98 g of Intermediate 4a (yield: 72%). The obtained compound was confirmed by LC-MS.

$C_{33}H_{22}BrNO$: calc. 527.09, found [M+1] 528.1.

2) Synthesis of Intermediate 4b 4.98 g (9.43 mmol) of Intermediate 4a was dissolved in 50 ml of benzene, 2.52 ml (28.3 mmol) of trifluoromethane sulfonic acid was then slowly added thereto, and the resultant solution was stirred at 80° C. for 2 hours. Then, the reaction solution was cooled down to room temperature, 40 ml of water was added to the reaction solution, and the resulting reaction solution was extracted three times with 50 ml of ethyl acetate. The obtained organic layer was dried with magnesium sulfate, and the solvent was evaporated therefrom to obtain a residue. The residue was recrystallized with ethyl acetate-hexane to obtain 3.9 g of Intermediate 4b (yield: 70%). The obtained compound was confirmed by LC-MS.

$C_{39}H_{26}BrN$: calc. 587.12, found [M+1] 587.12.

3) Synthesis of Intermediate 4

4.76 g of Intermediate 4 was obtained (yield: 75%) in the same manner as in step 5) of the synthesis of Intermediate 1, except that Intermediate 4b was used instead of Intermediate 1b. The obtained compound was confirmed by LC-MS.

$C_{46}H_{38}BNO_2$: calc. 635.30 found 436.30.

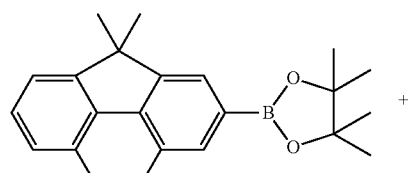

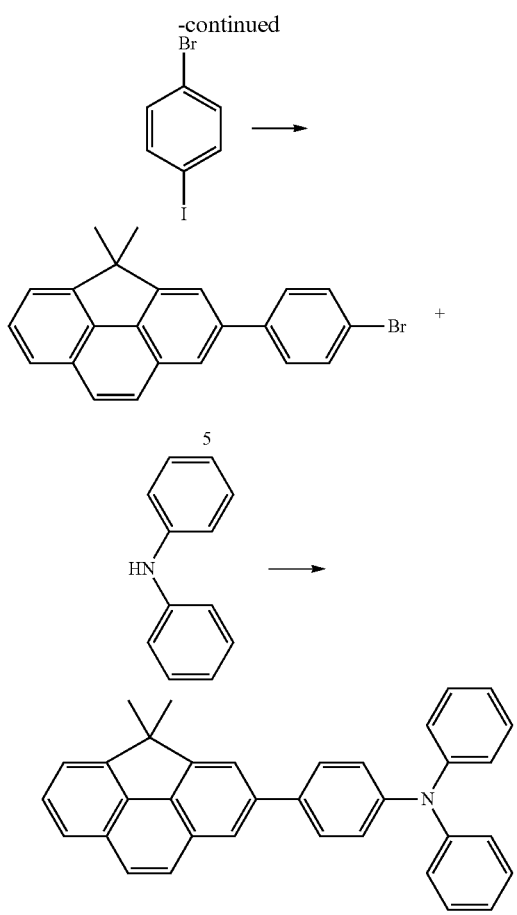

Synthesis of Intermediate 5

5.16 g (15.0 mmol) of Intermediate 1, 2.83 g (10.0 mmol) of 4-bromoiodobenzene, 0.18 g (0.2 mmol) of $Pd_2(dba)_3$, 0.04 g (0.4 mmol) of $PtBu_3$, and 1.44 g (15.0 mmol) of KOtBu were dissolved in 40 ml of toluene, and the resultant solution was stirred at 85° C. for 4 hours. Then, the reaction solution was cooled down to room temperature, 30 ml of water was added thereto, and the resultant reaction solution was extracted three times with 30 ml of diethylether. The obtained organic layer was dried with magnesium sulfate, and the solvent was evaporated therefrom to obtain a residue. The residue was purified with silicagel column chromatography to obtain 3.28 g of Intermediate 5 (yield: 88%). The obtained compound was confirmed by LC-MS.

$C_{23}H_{17}Br$: calc. 372.05, found [M+1] 373.1.

Synthesis of Compound 1

3.73 g (10 mmol) of Intermediate 5, 1.86 g (11 mmol) of diphenylamine, 0.18 g (0.2 mmol) of $Pd_2(dba)_3$, 0.04 g (0.2 mmol) of $P(tBu)_3$, and 1.44 g (15 mmol) of NaOtBu were dissolved in 70 ml of toluene, and the resultant solution was stirred at 80° C. for 4 hours. Then, the reaction solution was cooled down to room temperature, 40 ml of water was added thereto, and the resultant reaction solution was extracted three times with 50 ml of ethylether. The obtained organic layer was dried with magnesium sulfate, and the solvent was evaporated therefrom to obtain a residue. The residue was purified with silicagel column chromatography to obtain 3.45 g of Compound 1 (yield: 75%). The obtained compound was confirmed by $^1$H NMR and mass spectrometry/fast atom bombardment (MS/FAB).

$C_{35}H_{27}N$: calc. 461.21, found [M+1] 462.22.

$^1$H NMR (CDCl$_3$, 400 MHz) δ 8.09 (d, 1H), 7.75-7.71 (m, 2H), 7.64-7.62 (dd, 1H), 7.51 (s, 1H), 7.44-7.41 (m, 3H), 7.33-7.29 (t, 1H), 7.08 (m, 1H), 7.06 (m, 2H), 7.04 (m, 1H), 6.81-6.77 (m, 2H), 6.67-6.63 (m, 2H), 6.16-6.13 (m, 4H), 1.82 (s, 6H)

Synthesis of Compound 3

3.58 g of Compound 3 was obtained (yield: 65%) in the same manner as in the synthesis of Compound 1, except that 2,3,4,5,6-pentafluoro-N-phenylaniline was used instead of diphenylamine. The obtained compound was confirmed by $^1$H NMR and MS/FAB.

$C_{35}H_{22}F_5N$: calc. 551.17, found [M+1] 552.20.

$^1$H NMR (CDCl$_3$, 400 MHz) δ 8.10 (d, 1H), 7.75-7.72 (m, 2H), 7.64-7.62 (dd, 1H), 7.52 (s, 1H), 7.48-7.46 (m, 2H), 7.43-7.42 (d, 1H), 7.33-7.29 (t, 1H), 7.12-7.10 (m, 1H), 7.08-7.07 (m, 1H), 6.93-6.91 (m, 1H), 6.90-6.89 (m, 1H), 6.63-6.59 (m, 1H), 6.43-6.39 (m, 2H), 1.82 (s, 6H)

Synthesis of Compound 4

4.56 g of Compound 4 was obtained (yield: 79%) in the same manner as in the synthesis of Compound 1, except that (9,9-dimethyl-9H-fluorene-2-yl)-phenyl-amine was used instead of diphenylamine. The obtained compound was confirmed by $^1$H NMR and MS/FAB.

$C_{44}H_{35}N$: calc. 577.28, found [M+1] 578.28.

$^1$H NMR (CDCl$_3$, 400 MHz) δ 8.09 (d, 1H), 7.78-7.72 (m, 3H), 7.64-7.62 (dd, 1H), 7.56-7.49 (dd, 2H), 7.45-7.42 (m, 3H), 7.36-7.29 (m, 2H), 7.14-7.04 (m, 4H), 6.67-6.63 (m, 2H), 6.43-6.38 (m, 3H), 6.24-6.20 (m, 2H), 1.83 (s, 6H), 1.61 (s, 6H)

Synthesis of Compound 6

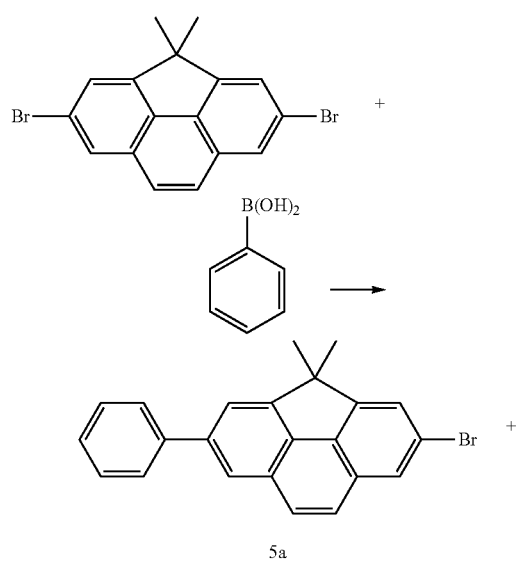

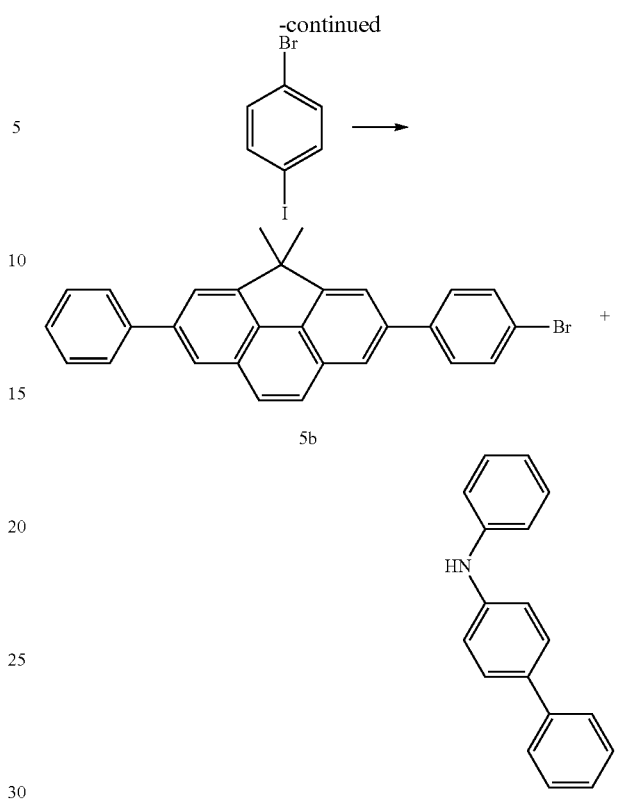

1) Synthesis of Intermediate 5a 3.76 g (10 mmol) of Intermediate 2b, 1.22 g (10 mmol) of phenylboric acid, 0.58 g (0.5 mmol) of Pd(PPh$_3$)$_4$, and 4.14 g (30 mmol) of K$_2$CO$_3$ were dissolved in 60 ml of THF and 40 ml of H$_2$O, and the resultant solution was then stirred at 80° C. for 24 hours. Then, the reaction solution was cooled down to room temperature, 40 ml of water was added thereto, and the resultant reaction solution was extracted three times with 50 ml of ethylether. The obtained organic layer was dried with magnesium sulfate, and the solvent was evaporated therefrom to obtain a residue. The residue was purified with silicagel column chromatography to obtain 2.68 g of Intermediate 5a (yield: 72%). The obtained compound was confirmed by LC-MS.

$C_{23}H_{17}Br$: calc. 372.05, found [M+1] 373.1.

2) Synthesis of Intermediate 5b 2.91 g of Intermediate 5b was obtained (yield: 65%) in the same manner as in the synthesis of Compound 5, except that Intermediate 5a was used instead of Intermediate 1. The obtained compound was confirmed by LC-MS.

$C_{29}H_{21}Br$: calc. 448.08, found [M+1] 449.10.

3) Synthesis of Compound 6

4.49 g (10 mmol) of Intermediate 5b, 2.45 g (10 mmol) of N-phenylbiphenyl-4-amine, 0.18 g (0.2 mmol) of Pd$_2$(dba)$_3$, 0.04 g (0.2 mmol) of P(tBu)$_3$, and 1.44 g (15.6 mmol) of NaOtBu were dissolved in 60 ml of toluene, and the resultant solution was stirred at 80° C. for 3 hours. Then, the reaction solution was cooled down to room temperature, 30 ml of water was added thereto, and the resultant reaction solution was extracted three times with 50 ml of ethylether. The obtained organic layer was dried with magnesium sulfate, and the solvent was evaporated therefrom to obtain a residue. The residue was purified with silicagel column chromatography to obtain 4.72 g of Compound 6 (yield: 77%). The obtained compound was confirmed by ¹H NMR and MS/FAB.

$C_{47}H_{35}N$: calc. 613.28, found [M+1] 614.30.

¹H NMR (CDCl₃, 400 MHz) δ 8.19 (d, 1H), 8.12 (d, 1H), 7.69-7.68 (m, 2H), 7.64-7.62 (m, 4H), 7.52-7.38 (m, 12H), 7.08-7.03 (m, 2H), 6.86-6.77 (m, 4H), 6.66-6.63 (m, 1H), 6.22-6.19 (m, 2H), 1.83 (s, 6H)

Synthesis of Compound 12

5.21 g of Compound 12 was obtained (yield: 85%) in the same manner as in the synthesis of Compound 1, except that bis-biphenyl-4-yl-amine was used instead of diphenylamine. The obtained compound was confirmed by ¹H NMR and MS/FAB.

$C_{47}H_{35}N$: calc. 613.28, found [M+1] 614.28.

¹H NMR (CDCl₃, 400 MHz) δ 8.10 (d, 1H), 7.75-7.71 (m, 2H), 7.64-7.61 (m, 5H), 7.52-7.49 (m, 5H), 7.44-7.38 (m, 9H), 7.33-7.29 (t, 1H), 6.86-6.82 (m, 4H), 6.54-6.50 (m, 2H), 1.82 (s, 6H)

Synthesis of Compound 13

4.68 g of Compound 13 was obtained (yield: 67%) in the same manner as in the synthesis of Compound 1, except that (9,9-diphenyl-9H-fluorene-2-yl)-phenyl-amine was used instead of diphenylamine. The obtained compound was confirmed by ¹H NMR and MS/FAB.

$C_{54}H_{37}N$: calc. 699.29, found [M+1] 670.30.

¹H NMR (CDCl₃, 400 MHz) δ 8.10 (d, 1H), 7.92-7.87 (m, 3H), 7.74-7.72 (m, 2H), 7.64-7.59 (m, 2H), 7.51 (s, 1H), 7.44-7.41 (m, 6H), 7.33-7.29 (t, 1H), 7.21-7.15 (m, 3H), 7.09-7.04 (m, 2H), 6.83-6.63 (m, 7H), 6.46 (d, 1H), 6.24-6.21 (m, 2H), 1.82 (s, 6H)

Synthesis of Compound 16

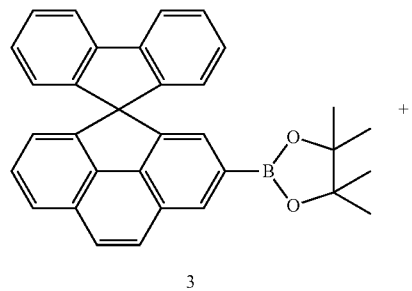

3

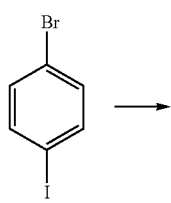

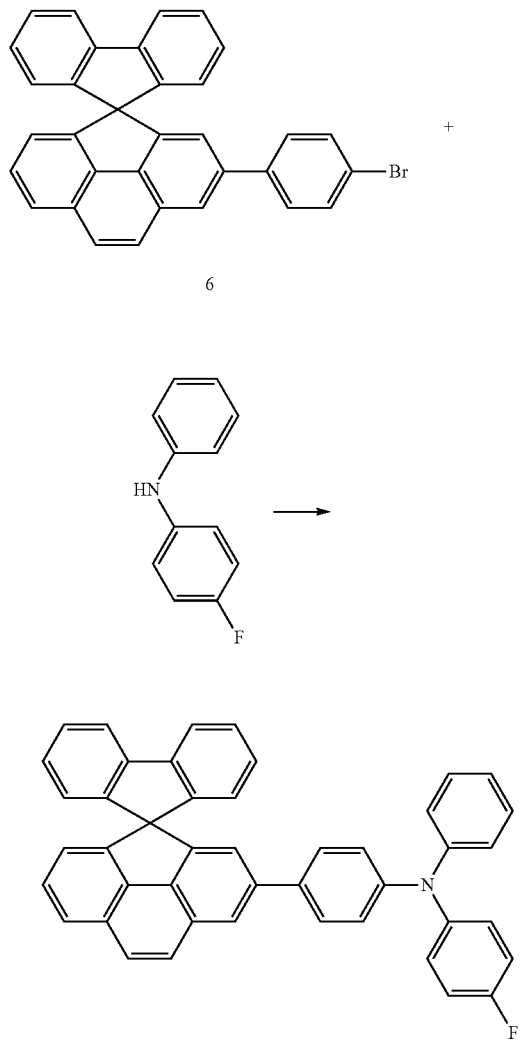

1) Synthesis of Intermediate 6

3.96 g of Intermediate 6 was obtained (yield: 80%) in the same manner as in the synthesis of Compound 5, except that Intermediate 3 was used instead of Intermediate 1. The obtained compound was confirmed by LC-MS.

$C_{33}H_{19}Br$: calc. 494.07, found [M+1] 495.10.

2) Synthesis of Compound 16

4.38 g of Compound 16 was obtained (yield: 73%) in the same manner as in the synthesis of Compound 1, except that Intermediate 6 was used instead of Intermediate 5. The obtained compound was confirmed by ¹H NMR and MS/FAB.

$C_{45}H_{28}FN$: calc. 601.22, found [M+1] 602.22.

¹H NMR (CDCl₃, 400 MHz) δ 8.12 (d, 1H), 7.94-7.92 (dd, 2H), 7.73-7.71 (m, 2H), 7.51 (s, 1H), 7.45-7.40 (m, 4H), 7.25 (d, 1H), 7.21-7.17 (m, 2H), 7.08-7.03 (m, 2H), 6.92-6.87 (m, 2H), 6.81-6.77 (m, 2H), 6.71-6.63 (m, 3H), 6.48-6.45 (m, 2H), 6.30-6.26 (t, 1H), 6.22-6.14 (m, 3H)

Synthesis of Compound 21

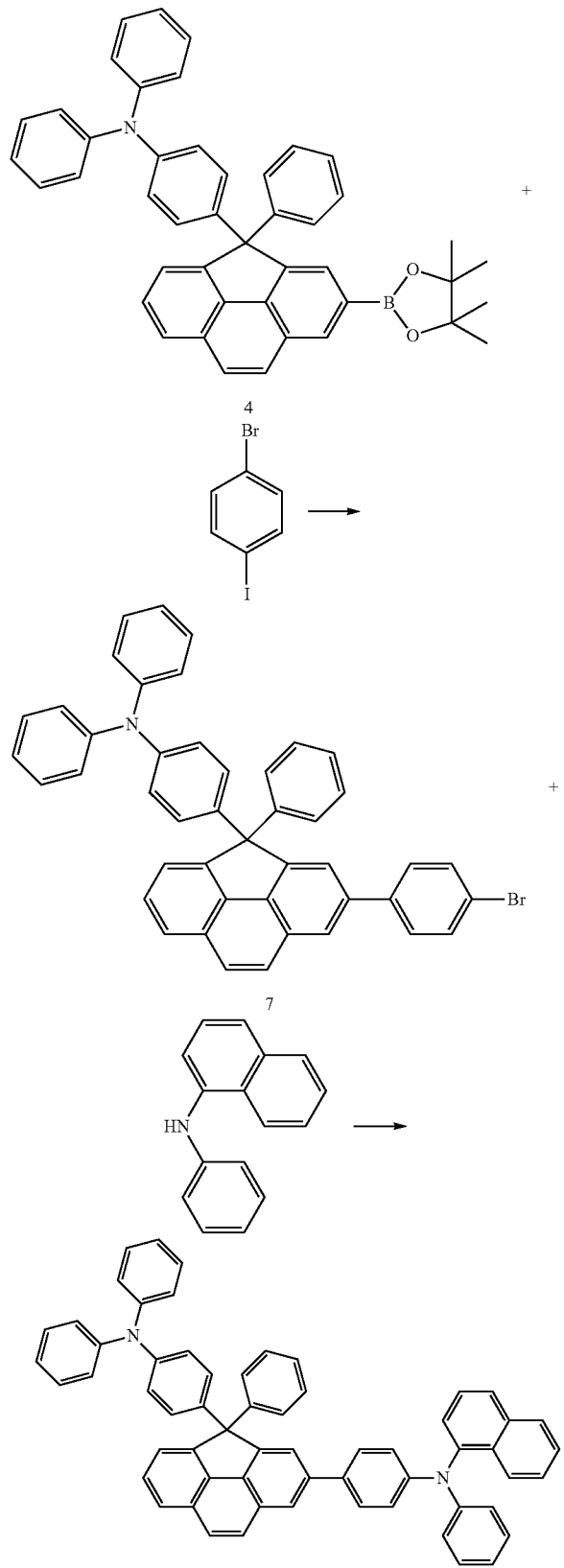

1) Synthesis of Intermediate 7

4.58 g of Intermediate 7 was obtained (yield: 69%) in the same manner as in the synthesis of Compound 5, except that Intermediate 4 was used instead of Intermediate 1. The obtained compound was confirmed by LC-MS.

$C_{45}H_{30}BrN$: calc. 664.63, found [M+1] 665.63.

2) Synthesis of Compound 21

6.18 g of Compound 21 was obtained (yield: 77%) in the same manner as in the synthesis of Compound 1, except that Intermediate 7 was used instead of Intermediate 5 and N-phenylnaphthalene-1-amine was used instead of diphenylamine. The obtained compound was confirmed by $^1$H NMR and MS/FAB.

$C_{61}H_{42}N_2$: calc. 802.33, found [M+1] 803.33.

$^1$H NMR (CDCl$_3$, 400 MHz) δ 8.17-8.13 (m, 2H), 7.87-7.85 (m, 1H), 7.70-7.68 (m, 1H), 7.56 (s, 1H), 7.49-7.83 (m, 7H), 7.28-7.21 (m, 3H), 7.15-7.01 (m, 10H), 6.81-6.74 (m, 3H), 6.66-6.61 (m, 3H), 6.53-6.50 (m, 2H), 6.28-6.23 (m, 2H), 6.16-6.13 (m, 5H), 6.08-6.05 (m, 2H)

Synthesis of Compound 22

5.29 g of Compound 22 was obtained (yield: 72%) in the same manner as in the synthesis of Compound 1, except that Intermediate 6 was used instead of Intermediate 5 and bis-biphenyl-3-yl-amine was used instead of diphenylamine. The obtained compound was confirmed by $^1$H NMR and MS/FAB.

$C_{57}H_{37}N$: calc. 735.29, found [M+1] 736.3.

$^1$H NMR (CDCl$_3$, 400 MHz) δ 8.13 (d, 1H), 7.70-7.69 (dd, 2H), 7.61-7.55 (m, 5H), 7.45-7.38 (m, 8H), 7.29-7.23 (m, 6H), 7.15-7.08 (m, 8H), 6.95-6.94 (m, 2H), 6.54-6.50 (m, 2H), 6.28-6.24 (t, 1H), 6.18-6.16 (m, 2H)

Synthesis of Compound 26

5.14 g of Compound 26 was obtained (yield: 65%) in the same manner as in the synthesis of Compound 1, except that bis-(4-carbazole-9-yl-phenyl)-amine was used instead of diphenylamine. The obtained compound was confirmed by $^1$H NMR and MS/FAB.

$C_{59}H_{41}N_3$: calc. 791.98, found [M+1] 792.99.

$^1$H NMR (CDCl$_3$, 400 MHz) δ 8.12-8.09 (m, 5H), 7.75-7.71 (m, 2H), 7.64-7.62 (dd, 1H), 7.52 (s, 1H), 7.44-7.41 (m, 3H), 7.35-7.25 (m, 13H), 7.15-7.12 (m, 4H), 6.83-6.79 (m, 4H), 6.54-6.50 (m, 2H), 1.82 (s, 6H)

Synthesis of Compound 27

5.52 g of Compound 27 was obtained (yield: 71%) in the same manner as in the synthesis of Compound 1, except that (4-carbazole-9-yl-phenyl)-[1,1';3'1"]terphenyl-5'-yl-amine was used instead of diphenylamine. The obtained compound was confirmed by $^1$H NMR and MS/FAB.

$C_{59}H_{42}N_2$: calc. 778.83, found [M+1] 779.83.

$^1$H NMR (CDCl$_3$, 400 MHz) δ 8.12-8.09 (m, 3H), 7.75-7.71 (m, 2H), 7.67-7.62 (m, 5H), 7.53-7.52 (m, 2H), 7.49 (s, 1H), 7.445-7.41 (m, 8H), 7.37 (s, 1H), 7.34-7.25 (m, 6H), 7.16-7.12 (m, 2H), 6.87-6.86 (d, 2H), 6.79-6.75 (m, 2H), 6.60-6.56 (m, 2H), 1.82 (s, 6H)
Synthesis of Compound 33
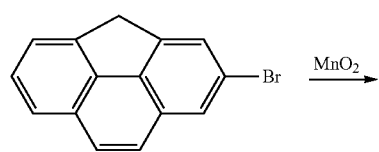
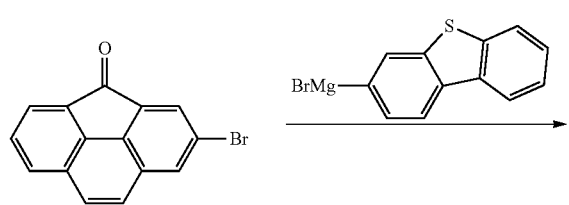
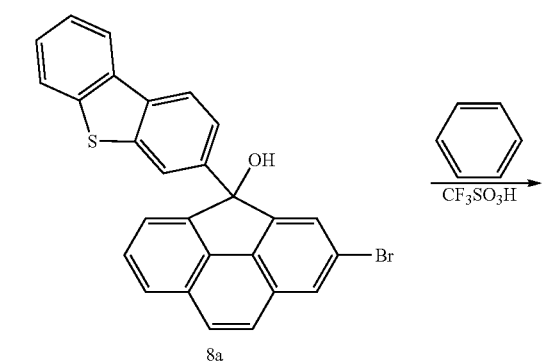
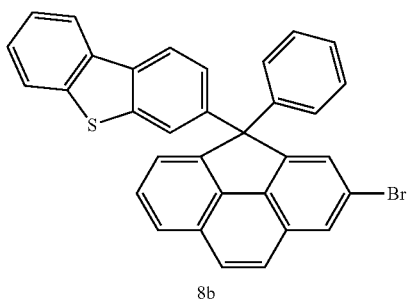
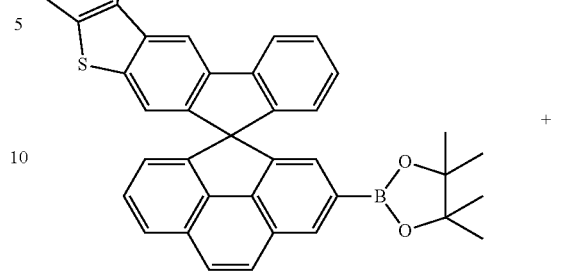
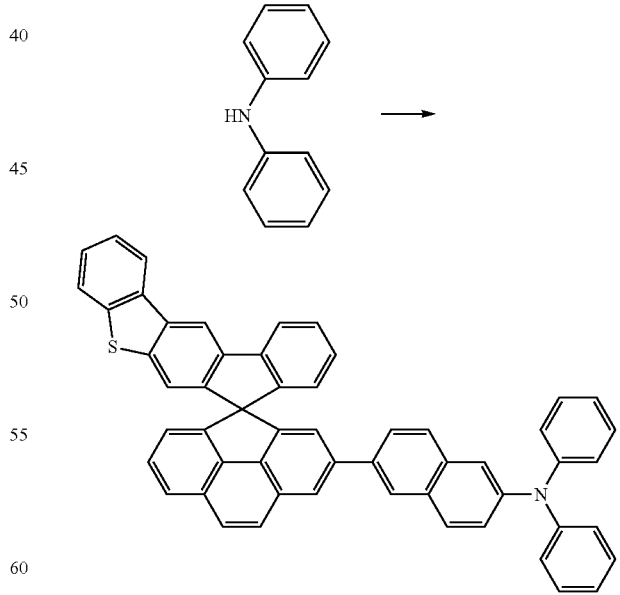
1) Synthesis of Intermediate 8a
2.84 g of Intermediate 8a was obtained (yield: 61%) in the same manner as in the synthesis of Intermediate 4a, except that (3-dibenzothienyl)-magnesium bromide was used instead of (4-(diphenylamino)-phenyl)-magnesium bromide. The obtained compound was confirmed by LC-MS.

$C_{27}H_{15}BrOS$: calc. 466.00, found [M+1] 467.00.

2) Synthesis of Intermediate 8b 2.84 g of Intermediate 8b was obtained (yield: 69%) in the same manner as in the synthesis of Intermediate 4b, except that Intermediate 8a was used instead of Intermediate 4a. The obtained compound was confirmed by LC-MS.

$C_{33}H_{19}BrS$: calc. 526.04, found [M+1] 527.04.

3) Synthesis of Intermediate 8

4.3 g of Intermediate 8 was obtained (yield: 75%) in the same manner as in the synthesis of Intermediate 1, except that Intermediate 8b was used instead of Intermediate 1b. The obtained compound was confirmed by LC-MS.

$C_{39}H_{31}BO_2S$: calc. 574.21, found 575.22.

4) Synthesis of Intermediate 9

3.77 g of Intermediate 9 was obtained (yield: 58%) in the same manner as in the synthesis of Compound 5, except that Intermediate 8 was used instead of Intermediate 1 and 2-bromo-6-iodonaphthalene was used instead of 4-bromoiodobenzene. The obtained compound was confirmed by LC-MS.

$C_{43}H_{23}BrS$: calc. 650.07, found [M+1] 651.10.

5) Synthesis of Compound 33

5.24 g of Compound 33 was obtained (yield: 71%) in the same manner as in the synthesis of Compound 1, except that Intermediate 9 was used instead of Intermediate 5. The obtained compound was confirmed by $^1$H NMR and MS/FAB.

$C_{55}H_{33}NS$: calc. 739.23, found [M+1] 740.23.

$^1$H NMR (CDCl$_3$, 400 MHz) δ 8.27 (d, 1H), 8.10 (d, 1H), 8.03-8.01 (m, 2H), 7.86-7.82 (m, 2H), 7.73-7.68 (m, 3H), 7.56 (s, 1H), 7.49-7.42 (m, 4H), 7.38-7.35 (t, 1H), 7.24-7.20 (m, 2H), 7.17-6.94 (m, 11H), 6.66-6.63 (m, 2H), 6.28-6.24 (t, 1H), 6.18-6.16 (m, 2H)

Synthesis of Compound 34

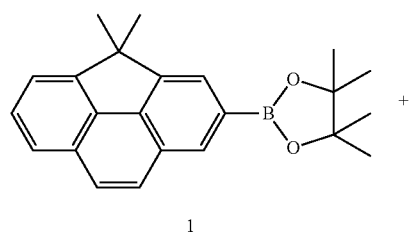

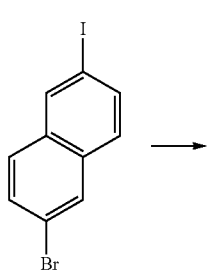

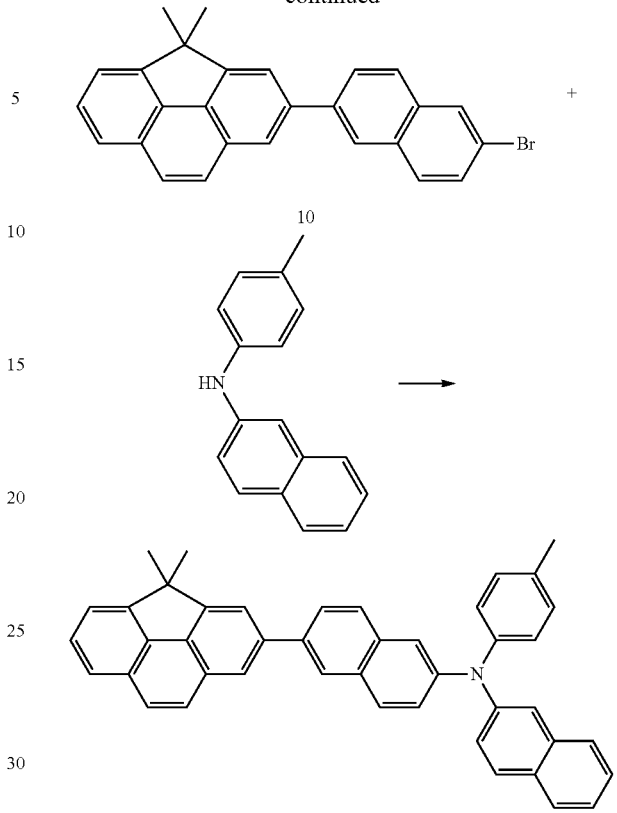

1) Synthesis of Intermediate 10

3.51 g of Intermediate 10 was obtained (yield: 83%) in the same manner as in the synthesis of Intermediate 5, except that 2-bromo-6-iodonaphthalene was used instead of 4-bromoiodobenzene. The obtained compound was confirmed by LC-MS.

$C_{27}H_{19}Br$: calc. 422.07, found [M+1] 423.07.

2) Synthesis of Compound 34

3.74 g of Compound 34 was obtained (yield: 65%) in the same manner as in the synthesis of Compound 1, except that Intermediate 10 was used instead of Intermediate 5 and N-p-tolylnaphthalene-2-amine was used instead of diphenylamine. The obtained compound was confirmed by $^1$H NMR and MS/FAB.

$C_{44}H_{33}N$: calc. 575.26, found [M+1] 576.26.

$^1$H NMR (CDCl$_3$, 400 MHz) δ 8.27 (d, 1H), 8.12 (d, 1H), 7.93-7.91 (dd, 1H), 7.86-7.84 (ss, 1H), 7.78-7.68 (m, 5H), 7.64-7.62 (dd, 1H), 7.57-7.53 (m, 6H), 7.41-7.40 (m, 1H), 7.33-7.29 (t, 1H), 7.20-7.17 (m, 1H), 7.11-7.09 (dd, 1H), 6.99-6.96 (m, 2H), 6.51-6.47 (m, 2H), 2.29 (s, 3H), 1.82 (s, 6H)

Synthesis of Compound 40

3.49 g of Compound 40 was obtained (yield: 59%) in the same manner as in the synthesis of Compound 1, except that Intermediate 10 was used instead of Intermediate 5 and N-phenyl(d5)biphenyl-4-amine was used instead of diphenylamine. The obtained compound was confirmed by $^1$H NMR and MS/FAB.

$C_{45}H_{28}D_5N$: calc. 592.29, found [M+1] 593.29.

$^1$H NMR (CDCl$_3$, 400 MHz) δ 8.27 (d, 1H), 8.12 (d, 1H), 7.93-7.91 (m, 1H), 7.82-7.80 (ss, 1H), 7.75-7.68 (m, 3H), 7.64-7.61 (m, 3H), 7.56 (s, 1H), 7.54-7.49 (m, 4H), 7.46-7.40 (m, 3H), 7.33-7.29 (t, 1H), 7.07-7.04 (m, 1H), 6.53-6.49 (m, 2H), 1.82 (s, 6H)

Synthesis of Compound 43

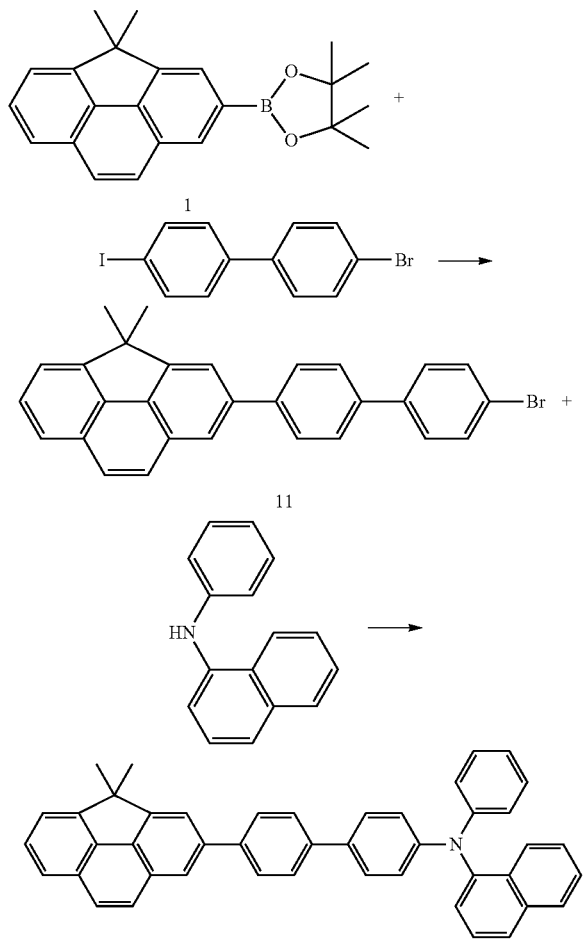

1) Synthesis of Intermediate 11

3.18 g of Intermediate 11 was obtained (yield: 71%) in the same manner as in the synthesis of Intermediate 5, except that 4-bromo-4'-iodobiphenyl was used instead of 4-bromoiodobenzene. The obtained compound was confirmed by LC-MS.

$C_{29}H_{21}Br$: calc. 448.08, found [M+1] 449.08.

2) Synthesis of Compound 43

4.35 g of Compound 43 was obtained (yield: 75%) in the same manner as in the synthesis of Compound 1, except that Intermediate 11 was used instead of Intermediate 5 and N-phenylnaphthalene-1-amine was used instead of diphenylamine. The obtained compound was confirmed by $^1$H NMR and MS/FAB.

$C_{45}H_{33}N$: calc. 587.26, found [M+1] 588.26.

$^1$H NMR (CDCl$_3$, 400 MHz) δ 8.17-8.15 (m, 2H), 7.87-7.85 (m, 1H), 7.75-7.62 (m, 7H), 7.51-7.37 (m, 8H), 7.33-7.29 (t, 2H), 7.25-7.21 (t, 1H), 6.86-6.82 (m, 3H), 6.75-6.73 (m, 1H), 6.65-6.62 (m, 2H), 1.82 (s, 6H)

Synthesis of Compound 46

4.81 g of Compound 46 was obtained (yield: 66%) in the same manner as in the synthesis of Compound 43, except that biphenyl-4-yl-(9,9-dimethyl-9H-fluoren-2-yl)-amine was used instead of N-phenylnaphthalene-1-amine. The obtained compound was confirmed by $^1$H NMR and MS/FAB.

$C_{56}H_{43}N$: calc. 729.34, found [M+1] 730.34.

$^1$H NMR (CDCl$_3$, 400 MHz) δ 8.17 (d, 1H), 7.78-7.61 (m, 10H), 7.56-7.29 (m, 12H), 7.14-7.08 (m, 2H), 6.71-6.69 (dd, 1H), 6.57-6.49 (m, 4H), 6.42-6.42 (d, 1H), 1.82 (s, 6H), 1.61 (s, 6H)

Synthesis of Compound 48

4.9 g of Compound 48 was obtained (yield: 80%) in the same manner as in the synthesis of Compound 6, except that diphenylamine was used instead of N-phenylbiphenyl-4-amine. The obtained compound was confirmed by LC-MS.

$C_{47}H_{35}N$: calc. 613.28, found [M+1] 614.28.

$^1$H NMR (CDCl$_3$, 400 MHz) δ 8.21-8.19 (m, 2H), 7.72-7.68 (m, 6H), 7.62 (s, 2H), 7.51-7.41 (m, 7H), 7.08-7.03 (m, 4H), 6.86-6.82 (m, 2H), 6.66-6.63 (m, 2H), 6.16-6.13 (m, 4H), 1.83 (s, 6H)

Synthesis of Compound 52

4.73 g of Compound 52 was obtained (yield: 70%) in the same manner as in the synthesis of Compound 43, except that N-(naphthalene-2-yl)dibenzo[b,d]-furan-3-amine was used instead of N-phenylnaphthalene-1-amine. The obtained compound was confirmed by $^1$H NMR and MS/FAB.

$C_{52}H_{35}NO$: calc. 677.27, found [M+1] 678.27.

$^1$H NMR (CDCl$_3$, 400 MHz) δ 8.17 (d, 1H), 7.79-7.62 (m, 13H), 7.58-7.37 (m, 9H), 7.33-7.29 (t, 1H), 7.01-6.97 (m, 2H), 6.90-6.87 (dd, 1H), 6.77-6.73 (m, 2H), 1.82 (s, 6H)

Synthesis of Compound 53

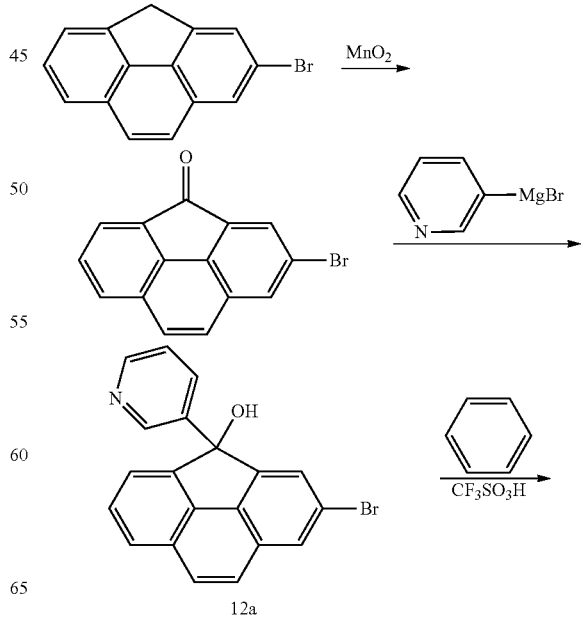

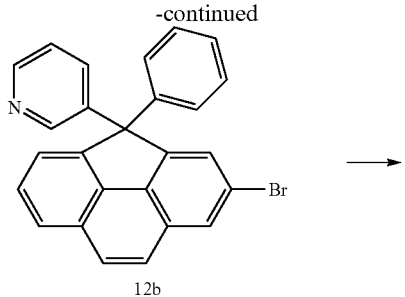

12b

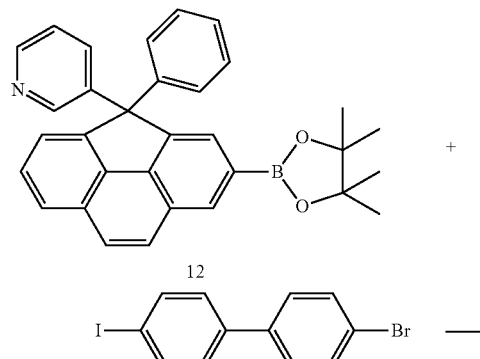

12

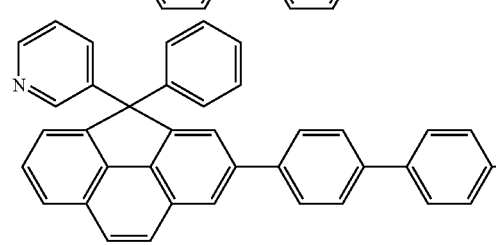

12

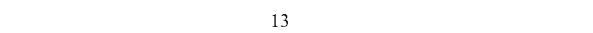

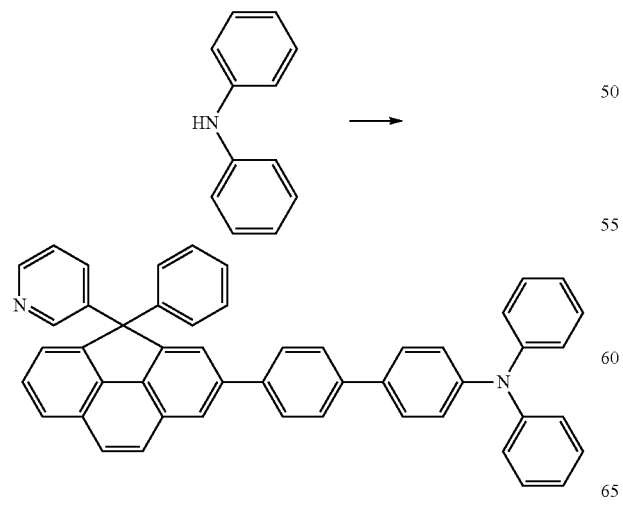

13

1) Synthesis of Intermediate 12a 2.49 g of Intermediate 12a was obtained (yield: 69%) in the same manner as in the synthesis of Intermediate 4a, except that pyridine-3-yl-magnesium bromide was used instead of (4-(diphenylamino)-phenyl)-magnesium bromide. The obtained compound was confirmed by LC-MS.

$C_{20}H_{12}BrNO$: calc. 361.01, found [M+1] 362.00.

2) Synthesis of Intermediate 12b 3.16 g of Intermediate 12b was obtained (yield: 75%) in the same manner as in the synthesis of Intermediate 4b, except that Intermediate 12a was used instead of Intermediate 4a. The obtained compound was confirmed by LC-MS.

$C_{26}H_{16}BrN$: calc. 421.05, found [M+1] 422.05.

3) Synthesis of Intermediate 12

3.61 g of Intermediate 12 was obtained (yield: 77%) in the same manner as in the synthesis of Intermediate 1, except that Intermediate 12b was used instead of Intermediate 1b. The obtained compound was confirmed by LC-MS.

$C_{32}H_{28}BNO_2$: calc. 469.22, found 470.22.

4) Synthesis of Intermediate 13

3.44 g of Intermediate 13 was obtained (yield: 60%) in the same manner as in the synthesis of Compound 5, except that Intermediate 12 was used instead of Intermediate 1 and 4-bromo-4'-iodobiphenyl was used instead of 4-bromoiodobenzene. The obtained compound was confirmed by LC-MS.

$C_{38}H_{24}BrN$: calc. 573.11, found [M+1] 574.11.

5) Synthesis of Compound 53

5.03 g of Compound 53 was obtained (yield: 76%) in the same manner as in the synthesis of Compound 1, except that Intermediate 12 was used instead of Intermediate 5. The obtained compound was confirmed by $^1$H NMR and MS/FAB.

$C_{50}H_{34}N_2$: calc. 662.27, found [M+1] 663.27.

$^1$H NMR (CDCl$_3$, 400 MHz) δ 8.47 (m, 1H), 8.34-8.32 (dd, 1H), 8.19 (S, 1H), 7.80-7.76 (m, 2H), 7.76 (S, 1H), 7.68-7.65 (m, 2H), 7.56 (S, 1H), 7.53-7.40 (m, 6H), 7.40 (S, 1H), 7.29-7.27 (dd, 1H), 7.17-7.13 (m, 4H), 7.06-7.03 (m, 4H), 6.86-6.82 (m, 2H), 6.66-6.63 (m, 2H), 6.32-6.28 (t, 1H), 6.16-6.13 (m, 4H)

Synthesis of Compound 54

1

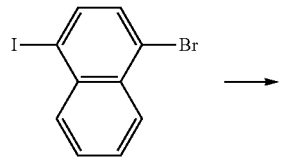

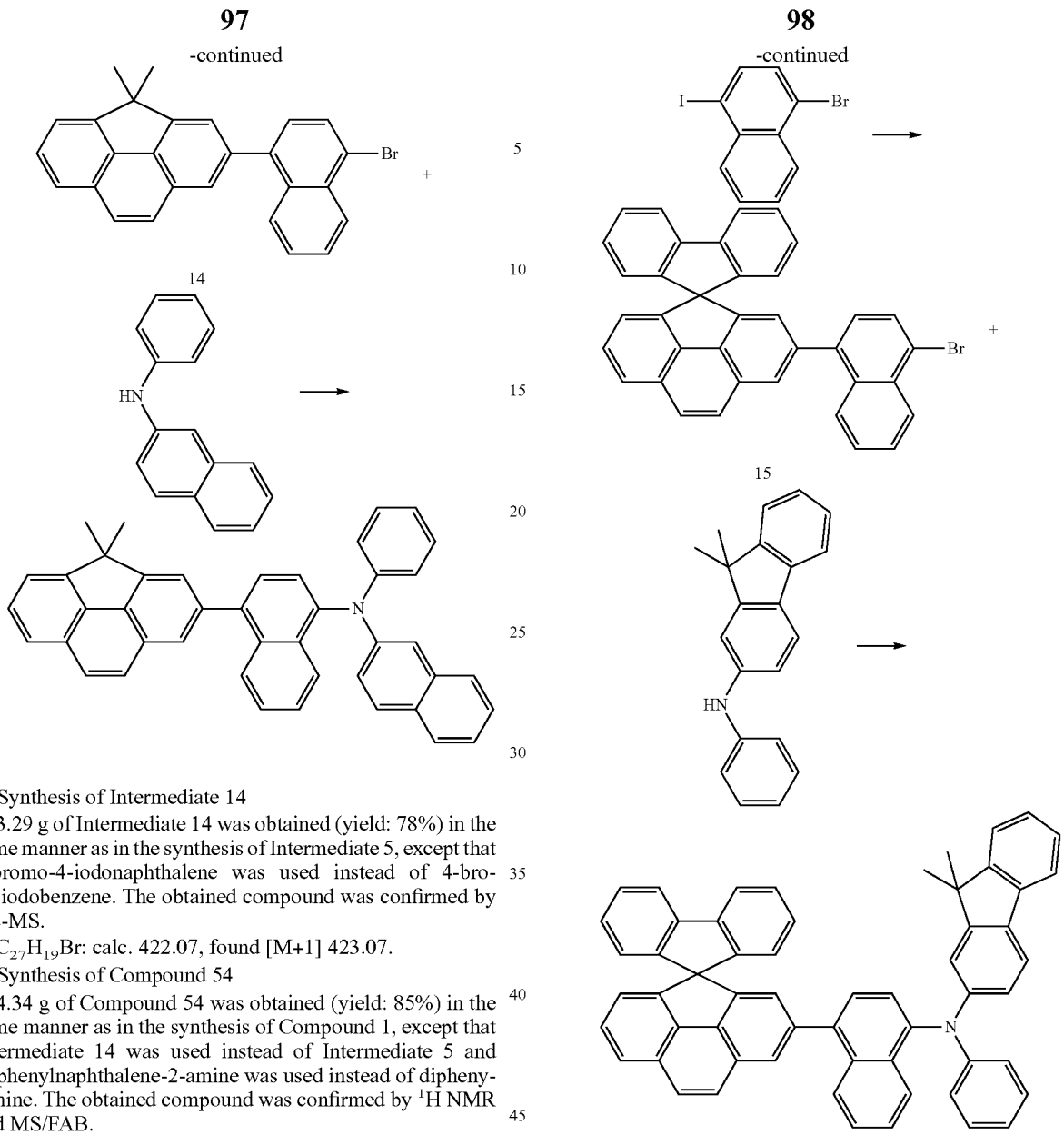

1) Synthesis of Intermediate 14

3.29 g of Intermediate 14 was obtained (yield: 78%) in the same manner as in the synthesis of Intermediate 5, except that 1-bromo-4-iodonaphthalene was used instead of 4-bromoiodobenzene. The obtained compound was confirmed by LC-MS.

$C_{27}H_{19}Br$: calc. 422.07, found [M+1] 423.07.

2) Synthesis of Compound 54

4.34 g of Compound 54 was obtained (yield: 85%) in the same manner as in the synthesis of Compound 1, except that Intermediate 14 was used instead of Intermediate 5 and N-phenylnaphthalene-2-amine was used instead of diphenylamine. The obtained compound was confirmed by $^1$H NMR and MS/FAB.

$C_{43}H_{31}N$: calc. 561.25, found [M+1] 562.25.

$^1$H NMR (CDCl$_3$, 400 MHz) δ 8.12 (d, 1H), 8.07-8.05 (m, 1H), 7.79-7.76 (m, 2H), 7.73-7.71 (m, 1H), 7.66-7.62 (m, 3H), 7.55-7.39 (m, 8H), 7.33-7.29 (t, 1H), 7.17-7.13 (m, 1H), 7.07-7.02 (m, 3H), 6.94-6.92 (ss, 1H), 6.64-6.61 (m, 1H), 6.12-6.09 (m, 2H), 1.89 (s, 6H)

Synthesis of Compound 60

1) Synthesis of Intermediate 15

3.81 g of Intermediate 15 was obtained (yield: 70%) in the same manner as in the synthesis of Intermediate 6, except that 1-bromo-4-iodonaphthalene was used instead of 4-bromoiodobenzene. The obtained compound was confirmed by LC-MS.

$C_{37}H_2Br$: calc. 544.08, found [M+1] 545.08.

2) Synthesis of Compound 60

5.76 g of Compound 60 was obtained (yield: 77%) in the same manner as in the synthesis of Compound 1, except that Intermediate 15 was used instead of Intermediate 5 and 9,9-dimethyl-N-phenyl-9H-fluorene-2-amine was used instead of diphenylamine. The obtained compound was confirmed by $^1$H NMR and MS/FAB.

$C_{58}H_{39}N$: calc. 749.31, found [M+1] 750.31.

$^1$H NMR (CDCl$_3$, 400 MHz) δ 8.12 (d, 1H), 8.07-8.05 (m, 1H), 7.78-7.76 (m, 1H), 7.71-7.68 (dd, 1H), 7.60 (ss, 1H), 7.51-7.46 (m, 2H), 7.45-7.36 (m, 3H), 7.35-7.31 (m, 2H), 7.27-7.24 (m, 4H), 7.17-7.02 (m, 12H), 6.66-6.59 (m, 3H), 6.37-6.36 (dd, 1H), 6.28-6.24 (t, 1H), 6.12-6.09 (m, 2H), 1.62 (s, 6H)

Synthesis of Compound 67

4.6 g of Compound 67 was obtained (yield: 75%) in the same manner as in the synthesis of Compound 6, except that N-phenyl-4-(pyridine-3-yl)amine was used instead of N-phenylbiphenyl-4-amine. The obtained compound was confirmed by $^1$H NMR and MS/FAB.

$C_{46}H_{34}N_2$: calc. 614.27, found [M+1] 615.27.

$^1$H NMR (CDCl$_3$, 400 MHz) δ 8.90 (m, 1H), 8.60-8.58 (m, 1H), 8.19 (s, 1H), 8.12 (d, 1H), 7.93-7.91 (m, 1H), 7.69-7.68 (m, 2H), 7.82 (s, 2H), 7.51-7.40 (m, 8H), 7.28-7.24 (m, 2H), 7.08-7.04 (m, 2H), 6.94-6.90 (m, 2H), 6.80-6.77 (m, 2H), 6.66-6.63 (m, 1H), 6.22-6.20 (m, 2H), 1.83 (s, 6H)

Synthesis of Compound 77

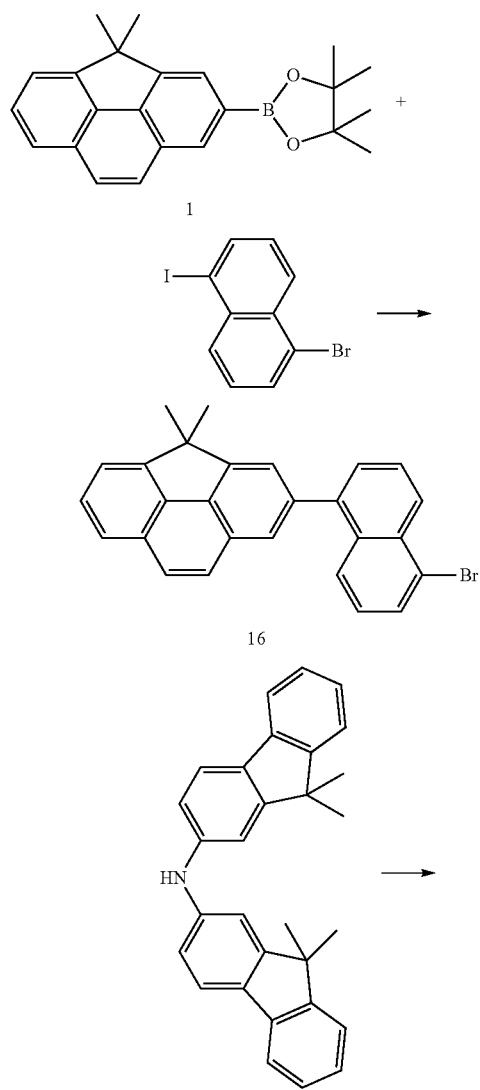

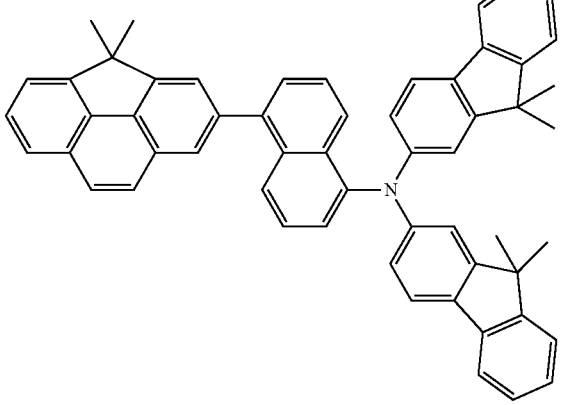

1) Synthesis of Intermediate 16

3.29 g of Intermediate 16 was obtained (yield: 78%) in the same manner as in the synthesis of Intermediate 5, except that 1-bromo-5-iodonaphthalene was used instead of 4-bromoiodobenzene. The obtained compound was confirmed by LC-MS.

$C_{27}H_{19}Br$: calc. 422.07, found [M+1] 423.07.

2) Synthesis of Compound 77

4.82 g of Compound 77 was obtained (yield: 65%) in the same manner as in the synthesis of Compound 1, except that Intermediate 16 was used instead of Intermediate 5 and bis(9,9-dimethyl-9H-fluorene-2-yl)amine was used instead of diphenylamine. The obtained compound was confirmed by $^1$H NMR and MS/FAB.

$C_{57}H_{45}N$: calc. 743.36, found [M+1] 744.36.

$^1$H NMR (CDCl$_3$, 400 MHz) δ 8.12 (d, 1H), 8.04-8.02 (m, 1H), 7.79-7.76 (m, 3H), 7.71 (m, 1H), 7.64 (d, 1H), 7.62 (d, 1H), 7.55-7.54 (m, 2H), 7.52 (s, 1H), 7.36-7.30 (m, 5H), 7.19-7.17 (m, 1H), 7.11-7.08 (m, 4H), 7.01-6.97 (t, 1H), 6.76-6.74 (m, 1H), 6.66-6.64 (dd, 2H), 6.41-6.40 (d, 2H), 1.86 (s, 6H), 1.61 (s, 12H)

Synthesis of Compound 80

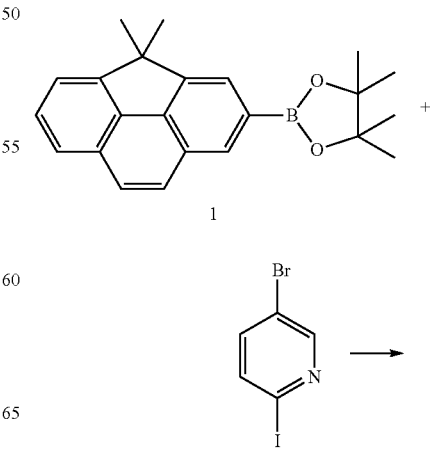

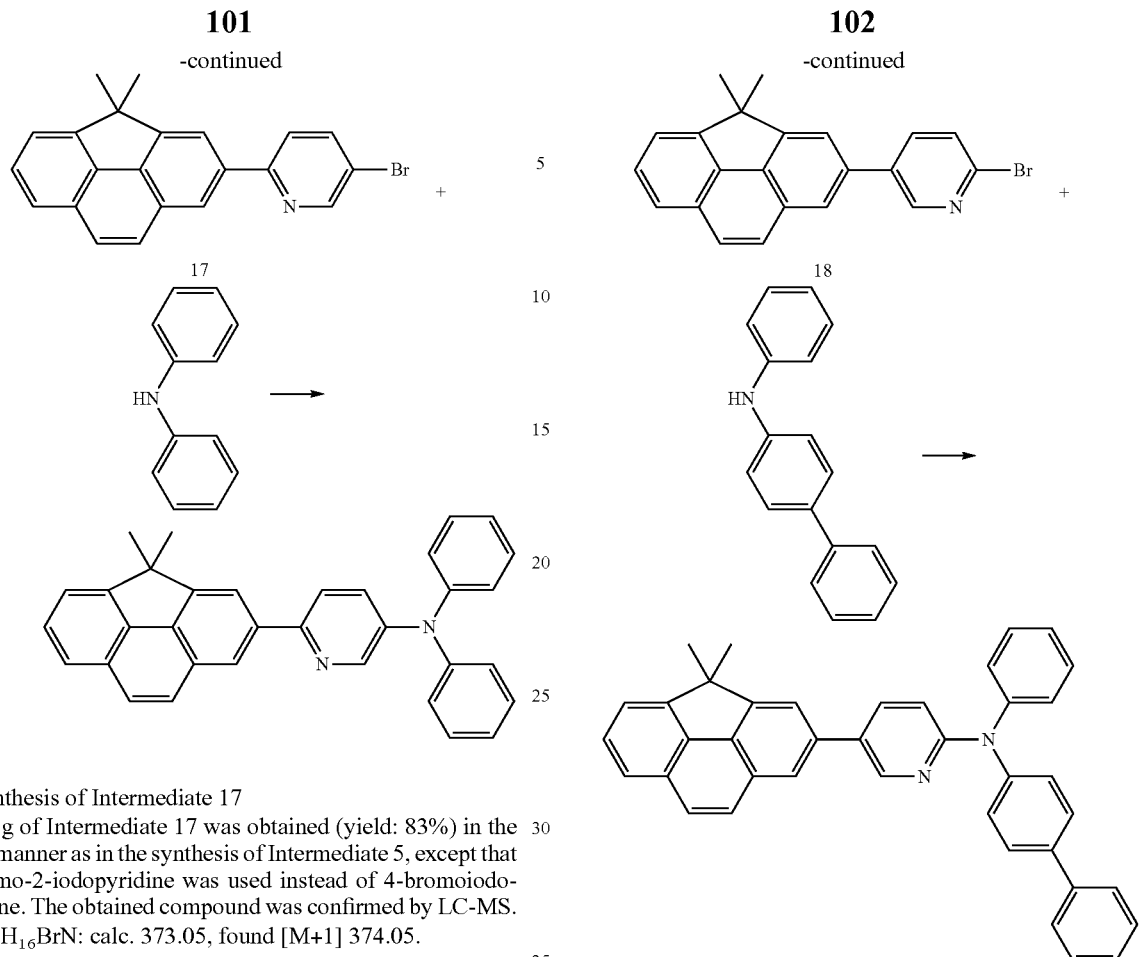

1) Synthesis of Intermediate 17

3.1 g of Intermediate 17 was obtained (yield: 83%) in the same manner as in the synthesis of Intermediate 5, except that 5-bromo-2-iodopyridine was used instead of 4-bromoiodobenzene. The obtained compound was confirmed by LC-MS.

$C_{22}H_{16}BrN$: calc. 373.05, found [M+1] 374.05.

2) Synthesis of Compound 80

4.82 g of Compound 80 was obtained (yield: 65%) in the same manner as in the synthesis of Compound 1, except that Intermediate 17 was used instead of Intermediate 5. The obtained compound was confirmed by $^1$H NMR and MS/FAB.

$C_{34}H_{26}N_2$: calc. 462.21, found [M+1] 463.21.

$^1$H NMR (CDCl$_3$, 400 MHz) δ 8.85 (s, 1H), 8.05 (d, 1H), 7.86 (d, 1H), 7.81 (m, 2H), 7.77 (s, 1H), 7.71 (m, 1H), 7.64-7.62 (dd, 1H), 7.33-7.29 (t, 1H), 7.12-7.09 (m, 4H), 6.92-6.89 (dd, 1H), 6.66-6.63 (m, 2H), 6.33-6.31 (m, 4H), 1.88 (s, 6H)

Synthesis of Compound 84

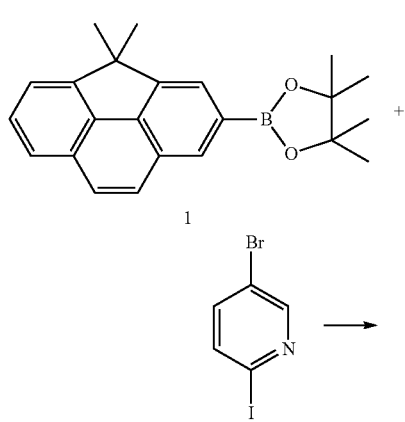

1) Synthesis of Intermediate 18

2.99 g of Intermediate 18 was obtained (yield: 80%) in the same manner as in the synthesis of Intermediate 5, except that 2-bromo-5-iodopyridine was used instead of 4-bromoiodobenzene. The obtained compound was confirmed by LC-MS.

$C_{22}H_{16}BrN$: calc. 373.05, found [M+1] 374.05.

2) Synthesis of Compound 84

4.25 g of Compound 84 was obtained (yield: 79%) in the same manner as in the synthesis of Compound 1, except that Intermediate 17 was used instead of Intermediate 5 and N-phenylbiphenyl-4-amine was used instead of diphenylamine. The obtained compound was confirmed by $^1$H NMR and MS/FAB.

$C_{40}H_{30}N_2$: calc. 538.24, found [M+1] 539.24.

$^1$H NMR (CDCl$_3$, 400 MHz) δ 8.39-8.38 (m, 1H), 8.08-8.05 (dd, 1H), 8.01 (m, 1H), 7.75-7.72 (m, 2H), 7.64-7.62 (m, 3H), 7.58 (s, 1H), 7.55-7.53 (m, 4H), 7.42-7.38 (m, 1H), 7.34-7.33 (d, 1H), 7.31-7.29 (ss, 1H), 7.25-7.20 (m, 2H), 6.95-6.90 (m, 1H), 6.71-6.69 (ss, 1H), 6.67-6.62 (m, 4H), 1.82 (s, 6H)

Synthesis of Compound 85

5.72 g of Compound 85 was obtained (yield: 83%) in the same manner as in the synthesis of Compound 43, except that dibiphenyl-4-yl-amine was used instead of N-phenylnaphthalene-1-amine. The obtained compound was confirmed by $^1$H NMR and MS/FAB.

$C_{53}H_{39}N$: calc. 689.31, found [M+1] 690.31.

$^1$H NMR (CDCl$_3$, 400 MHz) δ 8.17 (m, 1H), 7.75-7.61 (m, 11H), 7.52-7.49 (m, 6H), 7.46-7.38 (m, 8H), 7.33-7.29 (t, 1H), 6.86-6.82 (m, 4H), 6.61-6.57 (m, 2H), 1.82 (s, 6H)

Synthesis of Compound 87

5.84 g of Compound 87 was obtained (yield: 75%) in the same manner as in the synthesis of Compound 1, except that N-(4-(9-phenyl-9H-carbazole-3-yl)phenyl)biphenyl-4-amine was used instead of diphenylamine. The obtained compound was confirmed by $^1$H NMR and MS/FAB.

C$_{59}$H$_{42}$N$_2$: calc. 778.33, found [M+1] 779.33.

$^1$H NMR (CDCl$_3$, 400 MHz) δ 8.24-8.22 (m, 1H), 8.15 (d, 1H), 8.09 (d, 1H), 7.76-7.72 (m, 3H), 7.67-7.66 (d, 1H), 7.62 (m, 3H), 7.57-7.49 (m, 10H), 7.45-7.27 (m, 9H), 7.21-7.19 (m, 1H), 6.86-6.82 (m, 2H), 6.64-6.61 (m, 2H), 6.53-6.50 (m, 2H), 1.82 (s, 6H)

Synthesis of Compound 88

7.22 g of Compound 88 was obtained (yield: 80%) in the same manner as in the synthesis of Compound 16, except that N-(4-(9-phenyl-9H-carbazole-3-yl)phenyl)biphenyl-4-amine was used instead of 4-fluoro-N-phenylaniline. The obtained compound was confirmed by $^1$H NMR and MS/FAB.

C$_{69}$H$_{46}$N$_2$: calc. 902.37, found [M+1] 903.37.

$^1$H NMR (CDCl$_3$, 400 MHz) δ 8.24-8.22 (m, 1H), 8.15-8.13 (m, 2H), 7.76-7.73 (m, 1H), 7.71 (m, 1H), 7.67-7.62 (m, 3H), 7.56-7.50 (m, 10H), 7.45-7.35 (m, 8H), 7.31-7.25 (m, 6H), 7.21-7.19 (m, 1H), 7.15-7.07 (m, 8H), 6.86-6.82 (m, 1H), 6.64-6.61 (m, 2H), 6.53-6.50 (m, 2H), 6.28-6.24 (t, 1H)

Example 1

To prepare an anode, a 15 Ω/cm$^2$ (1200 Å) Corning ITO glass substrate was cut to a size of 50 mm×50 mm×0.7 mm, washed with ultrasonic waves in isopropyl alcohol and pure water for 5 minutes each, and then cleaned with UV and ozone for 30 minutes. The ITO glass substrate was mounted on a vacuum depositor.

2-TNATA was vacuum deposited on the ITO glass substrate to form a HIL having a thickness of 600 Å, and Compound 1 was vacuum deposited on the HIL to form a HTL having a thickness of 300 Å.

Next, 9,10-di-naphthalene-2-yl-anthracene (DNA) as a known blue fluorescent host and 1,4-bis-(2,2-diphenylvinyl)biphenyl (DPVBi) as a known blue fluorescent dopant were co-deposited on the HTL at a weight ratio of 98:2 to form an EML having a thickness of 300 Å.

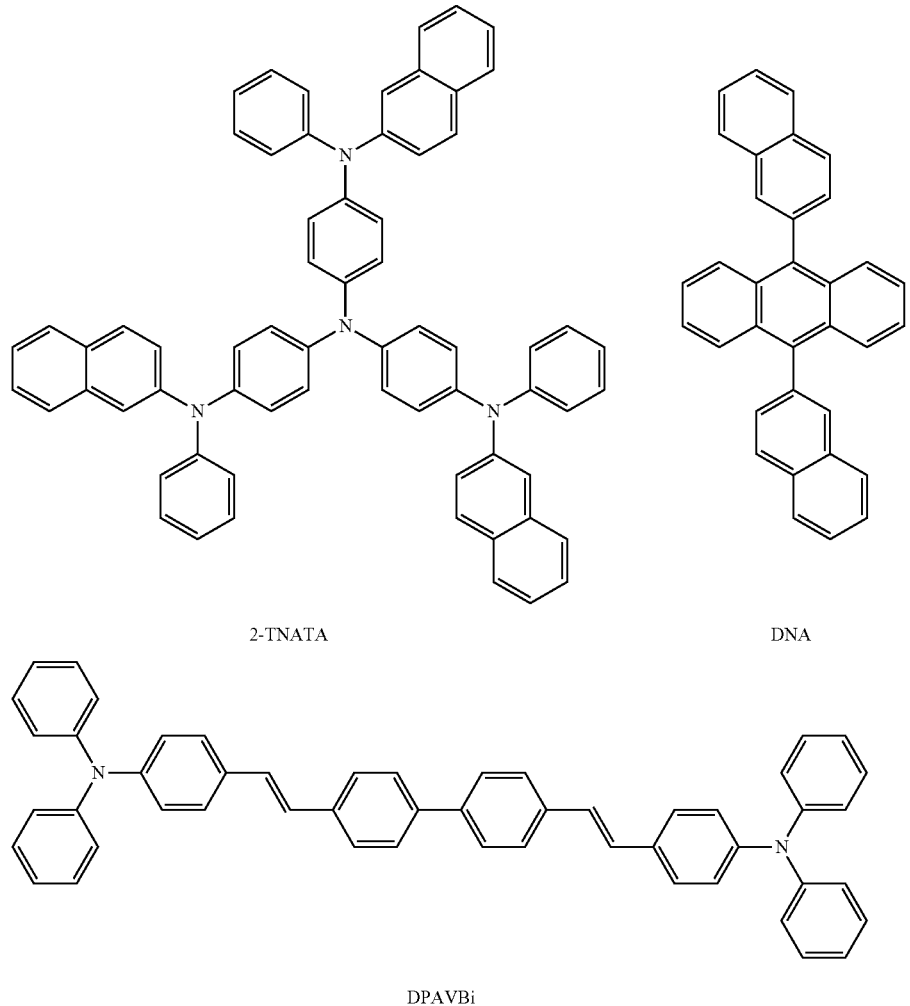

Subsequently, Alq$_3$ was deposited on the EML to form an ETL having a thickness of 300 Å, LiF (which is a halogenated alkali metal) was deposited on the ETL to form an EIL having a thickness of 10 Å, and Al was deposited on the EIL to form a LiF/Al electrode (cathode) having a thickness of 3,000 Å, thereby completing the manufacture of an OLED.

The OLED had a driving voltage of 6.63 V at a current density of 50 mA/cm$^2$, a brightness of 2,540 cd/m$^2$, a luminous efficiency of 5.08 cd/A, and a half-lifetime (hr @100 mA/cm$^2$) of 314 hours.

Example 2

An OLED was manufactured in the same manner as in Example 1, except that Compound 6 was used to form the HTL instead of Compound 1.

The OLED had a driving voltage of 6.77 V at a current density of 50 mA/cm$^2$, a brightness of 2,225 cd/m$^2$, a luminous efficiency of 4.45 cd/A, and a half-lifetime (hr @100 mA/cm$^2$) of 292 hours.

Example 3

An OLED was manufactured in the same manner as in Example 1, except that Compound 13 was used to form the HTL instead of Compound 1.

The OLED had a driving voltage of 7.05 V at a current density of 50 mA/cm$^2$, a brightness of 2,264 cd/m$^2$, a luminous efficiency of 4.52 cd/A, and a half-lifetime (hr @100 mA/cm$^2$) of 326 hours.

Example 4

An OLED was manufactured in the same manner as in Example 1, except that Compound 40 was used to form the HTL instead of Compound 1.

The OLED had a driving voltage of 6.96 V at a current density of 50 mA/cm$^2$, a brightness of 2,461 cd/m$^2$, a luminous efficiency of 4.92 cd/A, and a half-lifetime (hr @100 mA/cm$^2$) of 347 hours.

Example 5

An OLED was manufactured in the same manner as in Example 1, except that Compound 53 was used to form the HTL instead of Compound 1.

The OLED had a driving voltage of 6.72 V at a current density of 50 mA/cm$^2$, a brightness of 2,580 cd/m$^2$, a luminous efficiency of 5.16 cd/A, and a half-lifetime (hr @100 mA/cm$^2$) of 312 hours.

Example 6

An OLED was manufactured in the same manner as in Example 1, except that Compound 77 was used to form the HTL instead of Compound 1.

The OLED had a driving voltage of 6.58 V at a current density of 50 mA/cm$^2$, a brightness of 2,495 cd/m$^2$, a luminous efficiency of 4.99 cd/A, and a half-lifetime (hr @100 mA/cm$^2$) of 226 hours.

Example 7

An OLED was manufactured in the same manner as in Example 1, except that Compound 80 was used to form the HTL instead of Compound 1.

The OLED had a driving voltage of 6.39 V at a current density of 50 mA/cm$^2$, a brightness of 2,339 cd/m$^2$, a luminous efficiency of 4.67 cd/A, and a half-lifetime (hr @100 mA/cm$^2$) of 297 hours.

Example 8

An OLED was manufactured in the same manner as in Example 1, except that Compound 87 was used to form the HTL instead of Compound 1.

The OLED had a driving voltage of 6.55 V at a current density of 50 mA/cm$^2$, a brightness of 2,695 cd/m$^2$, a luminous efficiency of 5.39 cd/A, and a half-lifetime (hr @100 mA/cm$^2$) of 332 hours.

Comparative Example 1

An OLED was manufactured in the same manner as in Example 1, except that NPB was used to form the HTL instead of Compound 1.

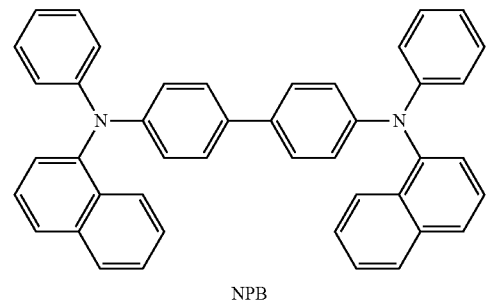

NPB

The OLED had a driving voltage of 7.35 V at a current density of 50 mA/cm$^2$, a brightness of 2,065 cd/m$^2$, a luminous efficiency of 4.13 cd/A, and a half-lifetime (hr @100 mA/cm$^2$) of 145 hours.

Comparative Example 2

An OLED was manufactured in the same manner as in Example 1, except that the following compound was used to form the HTL instead of Compound 1.

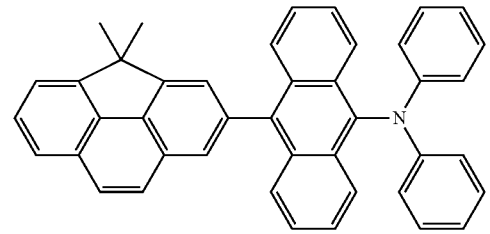 [SMILES: CC1(C)c2cccc3ccc4cc(-c5c6ccccc6c(N(c6ccccc6)c6ccccc6)c6ccccc56)cc1c4c23]

The OLED had a driving voltage of 6.99 V at a current density of 50 mA/cm$^2$, a brightness of 2,022 cd/m$^2$, a luminous efficiency of 4.04 cd/A, and a half-lifetime (hr @100 mA/cm$^2$) of 308 hours.

The characteristics and lifetimes of the OLEDs of Examples 1 to 8 and Comparative Examples 1 and 2 are shown in Table 1 below.

TABLE 1

| | Hole transporting material | Driving voltage (V) | Current density (mA/cm$^2$) | Brightness (cd/m$^2$) | Efficiency (cd/A) | Emission color | Half-lifetime (hr @100 mA/cm$^2$) |
|---|---|---|---|---|---|---|---|
| Example 1 | Compound 1 | 6.63 | 50 | 2,540 | 5.08 | blue | 314 hr |
| Example 2 | Compound 6 | 6.77 | 50 | 2,225 | 4.45 | blue | 292 hr |
| Example 3 | Compound 13 | 7.05 | 50 | 2,264 | 4.52 | blue | 326 hr |
| Example 4 | Compound 40 | 6.96 | 50 | 2,461 | 4.92 | blue | 347 hr |
| Example 5 | Compound 53 | 6.72 | 50 | 2,580 | 5.16 | blue | 312 hr |
| Example 6 | Compound 77 | 6.58 | 50 | 2,495 | 4.99 | blue | 226 hr |
| Example 7 | Compound 80 | 6.39 | 50 | 2,339 | 4.67 | blue | 297 hr |
| Example 8 | Compound 87 | 6.55 | 50 | 2,695 | 5.39 | blue | 332 hr |
| Comp. Example 1 | NPB | 7.35 | 50 | 2,065 | 4.13 | blue | 145 hr |
| Comp. Example 2 | Comp. Compound | 6.99 | 50 | 2,022 | 4.04 | blue | 308 hr |

From the results shown in Table 1, it was confirmed that when the compounds of Formula 1 were used as a hole transporting material, the OLEDs including the compounds of Formula 1 exhibited good current-voltage-luminance (I-V-L) characteristics, i.e., a significantly improved driving voltage and high efficiency, and in particular, exhibited a significantly improved lifetime, as compared to the OLED including NPB or a compound in which a linking group that links cyclopentaphenathrene and arylamine is an anthracene group.

As described above, according to one or more embodiments of the present invention, novel compounds represented by Formula 1 have good charge transporting abilities, and thus, may be suitable for use as hole injection materials or hole transporting materials in fluorescent and phosphorescent devices of all colors, such as red, green, blue, white, and the like. Thus, OLEDs including the compounds of Formula 1 may have high efficiency, low voltage, high brightness, and long lifetimes.

While the present invention has been illustrated and described with reference to certain exemplary embodiments, those of ordinary skill in the art will recognize that various changes to the described embodiments may be made without departing from the spirit and scope of the present invention as defined by the following claims.

What is claimed is:

1. A compound having hole injection ability and/or hole transporting ability, the compound being represented by Formula 1:

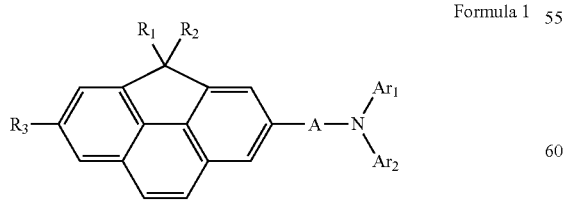

Formula 1 wherein:

$R_1$ and $R_2$ are each independently a halogen group, a cyano group, a substituted or unsubstituted $C_1$-$C_{60}$ alkyl group, a substituted or unsubstituted $C_6$-$C_{60}$ aryl group, a substituted or unsubstituted $C_3$-$C_{60}$ heteroaryl group, or a substituted or unsubstituted $C_6$-$C_{60}$ condensed polycyclic group;

$R_3$ is hydrogen, deuterium, a halogen group, a cyano group, an unsubstituted $C_6$-$C_{60}$ aryl group, a substituted or unsubstituted $C_3$-$C_{60}$ heteroaryl group, a substituted or unsubstituted $C_6$-$C_{60}$ condensed polycyclic group, or a $C_6$-$C_{60}$ aryl group substituted with a substituent selected from the group consisting of deuterium atoms, halogen atoms, hydroxyl groups, nitro groups, cyano groups, amidino groups, hydrazine groups, hydrazone groups, carboxyl groups and salts thereof, sulfonic acid groups and salts thereof, phosphoric acid groups and salts thereof, $C_1$-$C_{10}$ alkyl groups, $C_1$-$C_{10}$ alkoxy groups, $C_2$-$C_{10}$ alkenyl groups, $C_2$-$C_{10}$ alkynyl groups, $C_6$-$C_{16}$ aryl groups, and $C_4$-$C_{16}$ heteroaryl groups;

A is a linking group selected from any one of Formulae 4b through 4c or a linking group in which at least two compounds represented by Formulae 4b through 4c are linked:

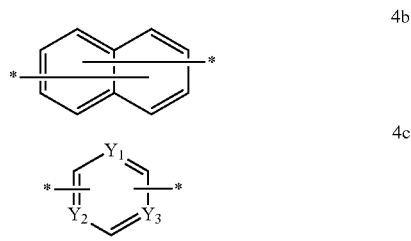

wherein:

$Y_1$, $Y_2$, and $Y_3$ are each independently a linking group represented by —N= or —C($R_{21}$)=, and at least one of $Y_1$, $Y_2$, and $Y_3$ is a linking group represented by —N=; and $R_{21}$ is a hydrogen atom, deuterium, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen group, or a cyano group; and $Ar_1$ and $Ar_2$ are each independently an unsubstituted $C_6$-$C_{60}$ aryl group, a substituted or unsubstituted $C_3$-$C_{60}$ heteroaryl group, a substituted or unsubstituted $C_6$-$C_{60}$ condensed polycyclic group, or a $C_6$-$C_{60}$ aryl group substituted with a substituent selected from the group consisting of deuterium atoms, halogen atoms, hydroxyl groups, nitro groups, cyano groups, amidino groups, hydrazine groups, hydrazone groups, carboxyl groups and salts thereof, sulfonic acid groups and salts thereof, phosphoric acid groups and salts thereof, $C_1$-$C_{10}$ alkyl groups, $C_1$-$C_{10}$ alkoxy groups, $C_2$-$C_{10}$ alkenyl groups, $C_2$-$C_{10}$ alkynyl groups, $C_6$-$C_{16}$ aryl groups, and $C_4$-$C_{16}$ heteroaryl groups.

2. The compound of claim 1, wherein:

$R_1$ and $R_2$ are each independently a halogen group, a cyano group, a substituted or unsubstituted $C_1$-$C_{30}$ alkyl group, a substituted or unsubstituted $C_6$-$C_{30}$ aryl group, a substituted or unsubstituted $C_3$-$C_{30}$ heteroaryl group, or a substituted or unsubstituted $C_6$-$C_{30}$ condensed polycyclic group;

$R_3$ is hydrogen, deuterium, a halogen group, a cyano group, an unsubstituted $C_6$-$C_{30}$ aryl group, a substituted or unsubstituted $C_3$-$C_{30}$ heteroaryl group, a substituted or unsubstituted $C_6$-$C_{30}$ condensed polycyclic group, or a $C_6$-$C_{60}$ aryl group substituted with a substituent selected from the group consisting of deuterium atoms, halogen atoms, hydroxyl groups, nitro groups, cyano groups, amidino groups, hydrazine groups, hydrazone groups, carboxyl groups and salts thereof, sulfonic acid groups and salts thereof, phosphoric acid groups and salts thereof, $C_1$-$C_{10}$ alkyl groups, $C_1$-$C_{10}$ alkoxy groups, $C_2$-$C_{10}$ alkenyl groups, $C_2$-$C_{10}$ alkynyl groups, $C_6$-$C_{16}$ aryl groups, and $C_4$-$C_{16}$ heteroaryl groups;

A is a linking group selected from any one of Formulae 4b through 4c or a linking group in which at least two compounds represented by Formulae 4b through 4c are linked; and $Ar_1$ and $Ar_2$ are each independently an unsubstituted $C_6$-$C_{30}$ aryl group, a substituted or unsubstituted $C_3$-$C_{30}$ heteroaryl group, a substituted or unsubstituted $C_6$-$C_{30}$ condensed polycyclic group, or a $C_6$-$C_{60}$ aryl group substituted with a substituent selected from the group consisting of deuterium atoms, halogen atoms, hydroxyl groups, nitro groups, cyano groups, amidino groups, hydrazine groups, hydrazone groups, carboxyl groups and salts thereof, sulfonic acid groups and salts thereof, phosphoric acid groups and salts thereof, $C_1$-$C_{10}$ alkyl groups, $C_1$-$C_{10}$ alkoxy groups, $C_2$-$C_{10}$ alkenyl groups, $C_2$-$C_{10}$ alkynyl groups, $C_6$-$C_{16}$ aryl groups, and $C_4$-$C_{16}$ heteroaryl groups.

3. The compound of claim 1, wherein $R_1$ and $R_2$ are each independently hydrogen, deuterium, a halogen group, a cyano group, a substituted or unsubstituted $C_1$-$C_{20}$ alkyl group, or any one of Formulae 2a to 2c below:

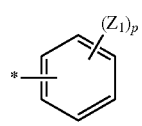
2a

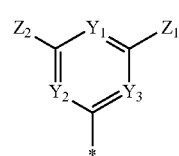
2b

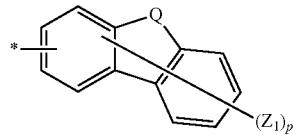
2c wherein:
$Y_1$, $Y_2$, and $Y_3$ are each independently a linking group represented by —N=, or —C($R_{21}$)=;
Q is a linking group represented by —C($R_{30}$)($R_{31}$)—, —N($R_{32}$)—, —S—, or —O—;
$Z_1$, $Z_2$, $R_{21}$, $R_{30}$, $R_{31}$, and $R_{32}$ are each independently a hydrogen atom, deuterium, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, an amino group substituted with a $C_6$-$C_{20}$ aryl group or a $C_3$-$C_{20}$ heteroaryl group, a halogen group, a cyano group, a nitro group, a hydroxyl group, or a carboxyl group;
p is an integer of 1 to 7; and
* is a binding site.

4. The compound of claim 1, wherein $R_3$ is hydrogen, deuterium, a halogen group, or at least one of Formulae 3A to 3d below:

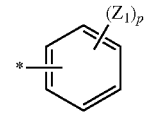
3a

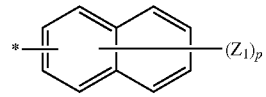
3b

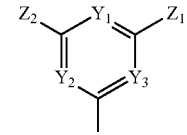
3c

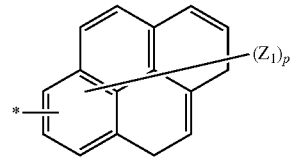
3d wherein:
$Y_1$, $Y_2$, and $Y_3$ are each independently a linking group represented by —N=, or —C($R_{21}$)=;
$Z_1$, $Z_2$, and $R_{21}$ are each independently a hydrogen atom, deuterium, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen group, a cyano group, a nitro group, a hydroxyl group, or a carboxyl group;
p is an integer of 1 to 9; and
* is a binding site.

5. The compound of claim 1, wherein $Ar_1$ and $Ar_2$ are each independently any one of Formulae 5a through 5e:

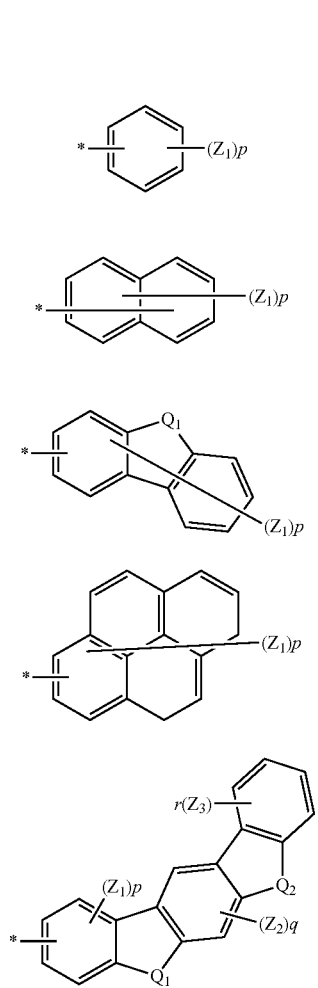

wherein:
$Q_1$ and $Q_2$ are each independently a linking group represented by —$C(R_{30})(R_{31})$—, —$N(R_{32})$—, —S—, or —O—;

$Z_1$, $Z_2$, $Z_3$, $R_{30}$, $R_{31}$, and $R_{32}$ are each independently a hydrogen atom, deuterium, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, an amino group substituted with a $C_6$-$C_{20}$ aryl group or a $C_3$-$C_{20}$ heteroaryl group, a halogen group, a cyano group, a nitro group, a hydroxyl group, or a carboxyl group;

p is an integer of 1 to 9;

q is 1 or 2;

r is an integer of 1 to 4; and

* is a binding site.

6. The compound of claim 1, wherein $R_1$ and $R_2$ combine to form a ring.

7. The compound of claim 1, wherein the compound of Formula 1 is any one of Compounds 40, 77 or 80:

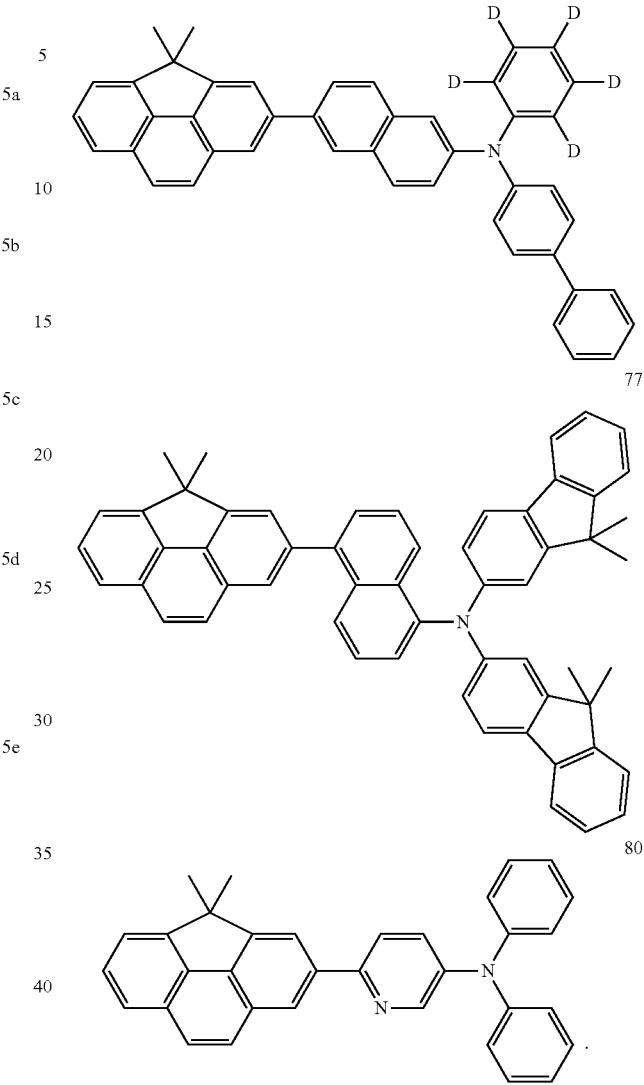

8. An organic light-emitting diode comprising:
a first electrode;
a second electrode; and
an organic layer between the first electrode and the second electrode,
wherein the organic layer comprises the compound according to claim 1.

9. The organic light-emitting diode of claim 8, wherein the organic layer is a hole injection layer, a hole transport layer, or a functional layer having both hole injection and hole transport abilities.

10. The organic light-emitting diode of claim 8, wherein the organic layer is a hole transport layer or a hole injection layer.

11. The organic light-emitting diode of claim 8, wherein the organic light-emitting diode comprises an emission layer, and at least one of a hole injection layer, a hole transport layer, or a functional layer having both hole injection and hole transport abilities, wherein one of the hole injection layer, the hole transport layer, or the functional layer comprises the compound according to claim 1, and the emission layer comprises an anthracene-based compound, an arylamine-based compound, or a styryl-based compound.

12. The organic light-emitting diode of claim 8, wherein the organic light-emitting diode comprises an emission layer, and at least one of a hole injection layer, a hole transport layer, or a functional layer having both hole injection and hole transport abilities, wherein one of the hole injection layer, the hole transport layer, or the functional layer comprises the compound according to claim 1, and any one of a red layer, a green layer, a blue layer, and a white layer of the emission layer comprises a phosphorescent compound.

13. The organic light-emitting diode of claim 12, wherein one of the hole injection layer, the hole transport layer, or the functional layer comprises a charge-generating material.

14. The organic light-emitting diode of claim 13, wherein the charge-generating material is a p-dopant selected from a quinone derivative, a metal oxide, or a cyano-containing compound.

15. The organic light-emitting diode of claim 8, wherein the organic layer comprises an electron transport layer comprising an electron transporting organic compound and a metal complex.

16. The organic light-emitting diode of claim 15, wherein the metal complex is a Li complex.

17. The organic light-emitting diode of claim 15, wherein the metal complex comprises lithium quinolate (LiQ) or Compound 203:

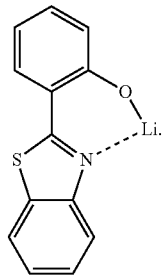

Compound 203

18. The organic light-emitting diode of claim 8, wherein the organic layer is formed using the compound according to claim 1 using a wet process.

19. A flat panel display device comprising the organic light-emitting diode of claim 8, wherein the first electrode of the organic light-emitting diode is electrically connected to a source electrode or a drain electrode of a thin film transistor.

* * * * *